(12) United States Patent
Yuyama et al.

(10) Patent No.: US 6,324,253 B1
(45) Date of Patent: Nov. 27, 2001

(54) TABLET INSPECTION APPARATUS

(75) Inventors: Shoji Yuyama; Hiroyasu Hamada, both of Osaka-fu (JP)

(73) Assignee: Yuyama Mfg. Co., Ltd., Toyonaka (JP)

( * ) Notice: Subject to any disclaimer, the term of this patent is extended or adjusted under 35 U.S.C. 154(b) by 0 days.

(21) Appl. No.: 09/383,020

(22) Filed: Aug. 25, 1999

(30) Foreign Application Priority Data

Aug. 26, 1998 (JP) .................................................. 10-240348

(51) Int. Cl.[7] .................................................. G01B 15/06
(52) U.S. Cl. .................................. 378/57; 209/589; 53/501
(58) Field of Search ................................ 378/57, 51, 58, 378/86; 209/589; 53/501

(56) References Cited

U.S. PATENT DOCUMENTS

| 5,125,017 | * | 6/1992 | Lempriere | ................................ | 378/86 |
| 5,638,657 | * | 6/1997 | Archer et al. | ........................... | 53/253 |

FOREIGN PATENT DOCUMENTS

| 63-294307 | 12/1988 | (JP) . |
| 4-17666 | 3/1992 | (JP) . |
| 5-337168 | 12/1993 | (JP) . |
| 8-168727 | 7/1996 | (JP) . |
| 7-200770 | * | 8/1995 | (JP) | .............................. | G06M/11/00 |

* cited by examiner

*Primary Examiner*—Robert H. Kim
*Assistant Examiner*—Pamela R. Hobden
(74) *Attorney, Agent, or Firm*—Wenderoth, Lind & Ponack, L.L.P.

(57) ABSTRACT

In the present invention, penetrating radiation (X-rays) is projected by penetrating radiation (X-ray) generating means 14 onto a tablet package 12a. The penetrating radiation (X-rays) is detected by penetrating radiation (X-ray) detecting means 16. Tablet count determining means 18 determines the number of tablets packaged in the tablet package 12a, based on the detection result supplied from the penetrating radiation (X-ray) detecting means 16. Comparing and verifying means 18 extracts from prescription data tablet count data associated with the tablets supposed to be packaged in the tablet package 12a, and verifies whether the tablets are packaged as directed by the prescription data, by comparing the tablet count data with the number of tablets determined by the tablet count determining means 18.

26 Claims, 52 Drawing Sheets

Continuous X-ray Generating Circuit

Pulsed X-ray Generating Circuit

Photon Spectrum

Photon Spectrum

Photon Spectrum

Tube Voltage Waveform

Upper:
 Ionization Chamber Output Waveform
 Interelectrode Gap ; 1mm
 Charged Gas Pressure ; 7 atm
 Applied Voltage ; 1200 V Lower : X-ray Waveform Pulse Response Characteristics
of Ionization Chamber X-ray Exposure Point     Exposure Pitch     0.76 mm Pitch Transmission Amount Transmission Amount p 2-1

Transmission Amount p 2-2

Transmission Amount p 2-3

X-ray Attenuation Characteristics (A)

(a)

(B)

(b)

Transmission Slice Surface z-a
z-b
z-c

Conveying Direction of Package

High X-ray Level

Low X-ray Level (A)

3599 0000 Coordinate 14
25
Wire
Tablet
12a
Tablet Fragment
41
26
16
1800

(B)

Guide Roller  Wire  Tablet  Tablet  Tablet Fragment

Transmissivity 100%

Z-coordinate ; 0.075 mm
X Tube Angle ; 5 degree 2170                                              1370

(A)

(B)

Z-coordinate ; 0.15 mm
X Tube Angle ; 10 degree

| Reference Data<br>Medication Name | Data corresponding to Fig. 10 | Data corresponding to Fig. 37 |
|---|---|---|
| EBUTOL |   |   |
| TOFRANIL |   |   |
| ALFAROL |   |   |
| PROMID |   |   |
| FLUITRAN |   |   |
| ANADROL |   |   |

(a)

| | | Difference | | |
|---|---|---|---|---|
| A | 2.5 | 2.5 | 5 | 4 | −1 |
| B | 2.5 | 2.5 | 5 | 6 | 1 |

(b)

C  D

| 2.5 | 2.5 |
|---|---|
| −0.5 | −0.5 |
| 2.5 | 2.5 |
| +0.5 | +0.5 |

| 5 | 5 |
|---|---|
| 3 | 7 |

Difference   −2    2

(c)

| 2 | 2 |
|---|---|
| −1 | +1 |
| 3 | 3 |
| −1 | +1 |

| 1 | 3 |
|---|---|
| 2 | 4 |

0 = 4 8 0
1 = 4 8 0

(a) a Linear Function
(b) b Inverse Function
(c) c Sectionally Linear Function
(d) d Quasi-contour Line Function (a)

e Threshold Processing (b)

f Band Processing (c)

g Contour Line Indication (a)

(b)

Bobbin Type Distortion

Barrel Type Distortion

Skew Distortion

Projective Distortion (A)
Stored Data (B)

Defect Portion (C)
Measured Data    Stored Data

TABLET INSPECTION APPARATUS

FIELD OF THE INVENTION

The present invention relates to a tablet inspection apparatus for automatically inspecting packaged tablets to verify whether they are packaged as directed by a prescription.

BACKGROUND OF THE INVENTION

Traditionally, inspection to verify whether tablets packaged by a tablet packaging machine are packaged as directed by a prescription has been performed visually by pharmacists. Apparatus for assisting such visual inspection by pharmacists are disclosed, for example, in Japanese Laid-open Patent Publication No. 63-294307 and Japanese Patent Publication No. 4-17666. These apparatus are designed to inspect tablet type and tablet count by capturing an image of packaged tablets with a camera.

However, since the image of the tablets packaged in a packaging sheet is captured in two dimensions, when more than one tablet is packed in a package the above inspection apparatus have often been unable to recognize the overlapping or contacting condition of the tablets, erroneously judging the condition as a packaging defect. Furthermore, when letters are printed with white paint in a stripe pattern on the packaging sheet, it is not possible to recognize the tablets concealed behind the stripe.

These problems will not be solved even if the images are captured from both sides of the packaging sheet. In view of this, apparatus for inspecting tablets by capturing their images as they are apart from each other just before packaging are disclosed in Japanese Laid-open Patent Publication Nos. 5-337168 and 8-168727. However, the processing speed of these apparatus is slow because the tablets must be separated from one another. Furthermore, since these apparatus inspect tablets just before packaging, not after packaging, if a tablet to be packed in a packaging sheet is erroneously put in an another packaging sheet before or after it, such wrong packaging cannot be detected, and reliability of the inspection apparatus is therefore low. For example, when the type of tablets to be taken in the morning is different from the type of tablets to be taken in the afternoon, if a tablet for the afternoon is put in the packaging sheet containing the tablets for the morning, then the package will be delivered as it is to the patient. As a result, he will take the tablet at the wrong time, defeating the purpose of medication. Furthermore, if a machine part such as a screw or spring or other foreign matter such as an insect or dust gets mixed when packaging, there is a danger that the package may be delivered as it is to the patient who then may erroneously swallow it with the tablets.

SUMMARY OF THE INVENTION

The present invention has been devised in view of the above problems, and an object of the invention is to provide a tablet inspection apparatus that has high reliability and high processing speed, and that can monitor inspection data after tablets are delivered to the patient, enabling to alleviate the inspection labor of pharmacists.

As a first means to solve the aforementioned problems, the present invention provides a tablet inspection apparatus for inspecting tablets packaged in a tablet package based on prescription data, comprising: penetrating radiation generating means for generating penetrating radiation and projecting the same onto the tablet package; penetrating radiation detecting means for detecting the penetrating radiation generated by the penetrating radiation generating means; tablet count determining means for determining the number of tablets packaged in the tablet package, based on a detection result supplied from the penetrating radiation detecting means; and comparing and verifying means for verifying whether the tablets are packaged as directed by the prescription data, by extracting from the prescription data tablet count data associated with the tablets supposed to be packaged in the tablet package and by comparing the tablet count data with the number of tablets determined by the tablet count determining means. The term "tablet package" used herein refers not only to a packaging sheet but also to a vial bottle or a cylindrical bottle fitted with a cap. Also, the term "penetrating radiation" refers not only to X-rays but also to radioactive rays and light rays, such as infrared rays, capable of penetrating objects.

According to the invention as the first means, the number of tablets packaged in the tablet package is determined based on the detection result supplied from the penetrating radiation detecting means, and whether the tablets are packaged as directed by the prescription data is verified by comparing the number of tablets thus determined with the tablet count data associated with the tablets supposed to be packaged in the tablet package. Accordingly, the inspection of the packaged tablets can be done in a simple manner and at high speed and, at the same time, the reliability can be enhanced.

As a second means to solve the aforementioned problems, the present invention provides a tablet inspection apparatus for inspecting tablets packaged in a tablet package based on prescription data, comprising: penetrating radiation generating means for generating penetrating radiation and projecting the same onto the tablet package; penetrating radiation detecting means for detecting the penetrating radiation generated by the penetrating radiation generating means; tablet shape identifying means for identifying the shape of each of the tablets packaged in the tablet package, based on a detection result supplied from the penetrating radiation detecting means; storage means for storing tablet shape data for each tablet type; and comparing and verifying means for verifying whether the tablets are packaged as directed by the prescription data, by extracting from the prescription data the tablet type of the tablets supposed to be packaged in the tablet package, by retrieving the tablet shape data corresponding to the tablet type from the storage means, and by comparing the tablet shape data with the tablet shape identified by the tablet shape identifying means.

According to the invention as the second means, the shape of each of the tablets packaged in the tablet package is identified based on the detection result supplied from the penetrating radiation detecting means, and whether the tablets are packaged as directed by the prescription data is verified by comparing the thus identified tablet shape with the tablet shape data associated with the tablets supposed to be packaged in the tablet package. Accordingly, as in the first means, the inspection of the packaged tablets can be done in a simple manner and at high speed and, at the same time, the reliability can be enhanced.

As a third means to solve the aforementioned problems, the present invention provides a tablet inspection apparatus for inspecting tablets packaged in a tablet package based on prescription data, comprising: penetrating radiation generating means for generating penetrating radiation and projecting the same onto the tablet package; penetrating radiation detecting means for detecting the penetrating radiation generated by the penetrating radiation generating means; tablet shape identifying means for identifying the shape of each of the tablets packaged in the tablet package, based on a detection result supplied from the penetrating radiation detecting means; storage means for storing tablet shape data for each tablet type; tablet count determining means for determining the number of tablets packaged in the tablet package, by extracting from the prescription data the tablet type of the tablets supposed to be packaged in the tablet package, by retrieving the tablet shape data corresponding to the tablet type from the storage means, and by matching the tablet shape data against the tablet shape identified by the tablet shape identifying means; and comparing and verifying means for verifying whether the tablets are packaged as directed by the prescription data, by extracting from the prescription data the tablet type and tablet count data associated with the tablets supposed to be packaged in the tablet package and by comparing the tablet count data with the number of tablets determined by the tablet count determining means.

According to the invention as the third means, the number of tablets packaged in the tablet package is determined based on the detection result supplied from the penetrating radiation detecting means, and whether the tablets are packaged as directed by the prescription data is verified by comparing the number of tablets thus determined with the tablet count data associated with the tablets supposed to be packaged in the tablet package. Accordingly, as in the first invention, the inspection of the packaged tablets can be done in a simple manner and at high speed and, at the same time, the reliability can be enhanced.

The tablet count determining means may be configured to render the tablet package defective when the data detected by the penetrating radiation detecting means contains data not countable as a tablet or when the data detected by the penetrating radiation detecting means contains data from which the shape cannot be recognized. This further enhances the reliability. Marking means may be provided which appends a mark to the tablet package when the tablet package is judged to be defective. By so doing, defective packages can be easily recognized.

The penetrating radiation detecting means may defect the amount of penetrating radiation transmitted through the tablet package or may defect a tablet shadow.

As a fourth means to solve the aforementioned problems, the present invention provides a-tablet inspection apparatus for inspecting tablets packaged in a tablet package based on prescription data, comprising: penetrating radiation generating means for generating penetrating radiation and projecting the same onto the tablet package; penetrating radiation detecting means for detecting the penetrating radiation generated by the penetrating radiation generating means; storage means for storing tablet image data for each tablet type; tablet identifying means for identifying the tablet type of each of the tablets packaged in the tablet package by capturing the tablet shape thereof from a detection result supplied from the penetrating radiation detecting means; and video data creating means for creating video data by retrieving the tablet image data corresponding to the tablet type from the storage means and by superimposing the image data on the data detected by the penetrating radiation detecting means.

According to the invention as the fourth means, the tablet type is identified based on the detection result supplied from the penetrating radiation detecting means, and the video data is created by superimposing the tablet image data corresponding to the tablet type onto the penetrating radiation detection data. In this way, since the packaged tablets can be presented for viewing as video data, the tablets can be inspected easily.

The tablet inspection apparatus may include display means for displaying the video data or storage means for storing the video data by associating the same with prescription data. This further simplifies the tablet inspection procedures and shortens the inspection time.

In the invention as the first to fourth means, a plurality of the penetrating radiation generating means and a plurality of the penetrating radiation detecting means may be located in different radiation directions and reproducing means for reproducing the detection data from the penetrating radiation detecting means in three-dimensional perspective may be provided. Further, the penetrating radiation generating means may be mounted rotatably around the tablet package so as to enable the direction of radiation to be changed and producing means for reproducing the detection data from the penetrating radiation detecting means in three-dimensional perspective may also be provided. With the provision of such means, if the tablets are packaged one overlapping another, each individual tablet can be identified reliably, further improving the inspection reliability.

DESCRIPTION OF THE PREFERRED EMBODIMENTS

Embodiments of the present invention will be described below with reference to the accompanying drawings.

Embodiment 1

Figure 1:
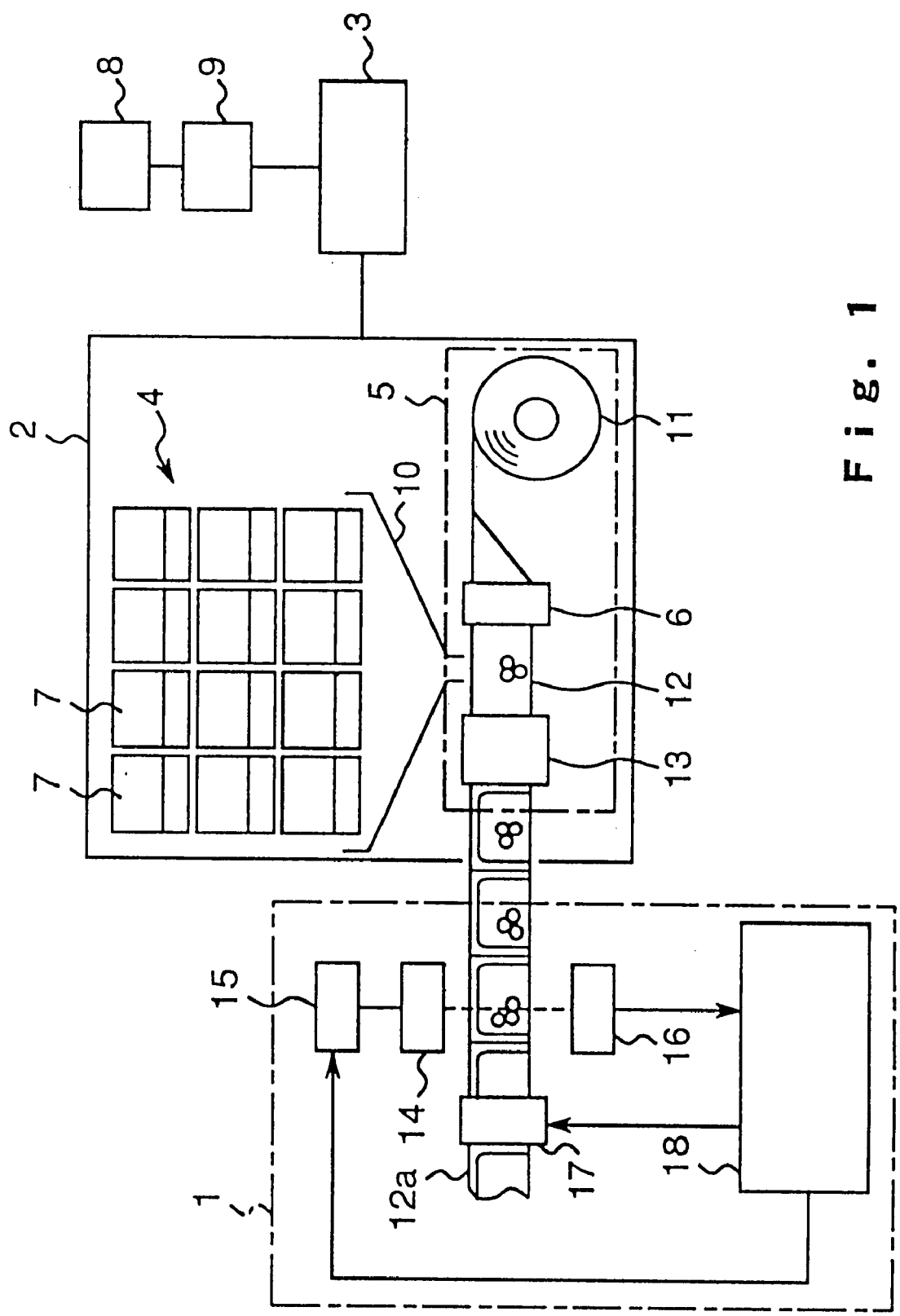
FIG. 1 is a simplified schematic diagram showing the configuration of a tablet packaging machine equipped with a tablet inspection apparatus according to a first embodiment of the present invention.

FIG. 1 shows a tablet packaging machine 2 equipped with a tablet inspection apparatus 1 according to the present invention. The tablet packaging machine 2 comprises a tablet feeder 4, a packaging device 5, and a printer 6 which are controlled by a controller 3. The tablet feeder 4 comprises a large number of cassettes 7 for accommodating tablets by the type. The tablet feeder 4 feeds tablets from the cassette 7 concerned in accordance with prescription data received from a host computer 8 via a personal computer 9. The tablets fed from the tablet feeder 4 are introduced through a hopper 10 into the packaging device 5. In the packaging device 5, a packaging sheet 12 being fed by a predetermined amount at a time from a roll 11 is folded in two along the longitudinal direction thereof. When a dose of tablets is put in, the packaging sheet 12 is sealed by a heater roller 13 for packaging. The feed amount of the packaging sheet 12 is detected by an encoder not shown. The printer 6 prints the dosing time, the patient's name, etc. on the packaging sheet 12. The tablets packaged in the packaging sheet 12 are inspected by the tablet inspection apparatus 1 described below.

The tablet inspection apparatus 1 comprises an X-ray tube as a penetrating radiation generator, a controller 15 for the X-ray tube 14, a line sensor 16 as a penetrating radiation detector, a mark appender 17, and a controller 18.

Figure 2:
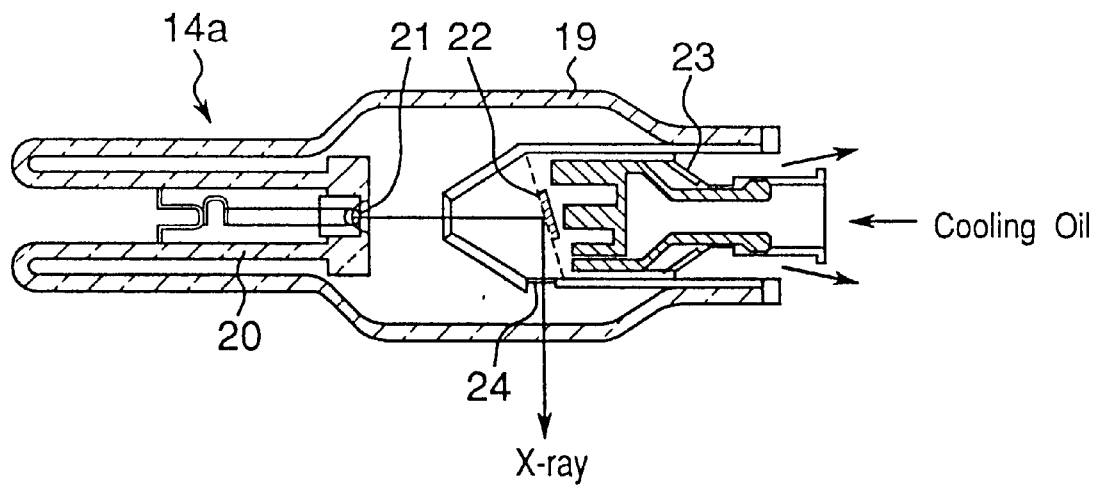
FIG. 2 is a sectional view of a fixed target X-ray tube.
Figure 3:
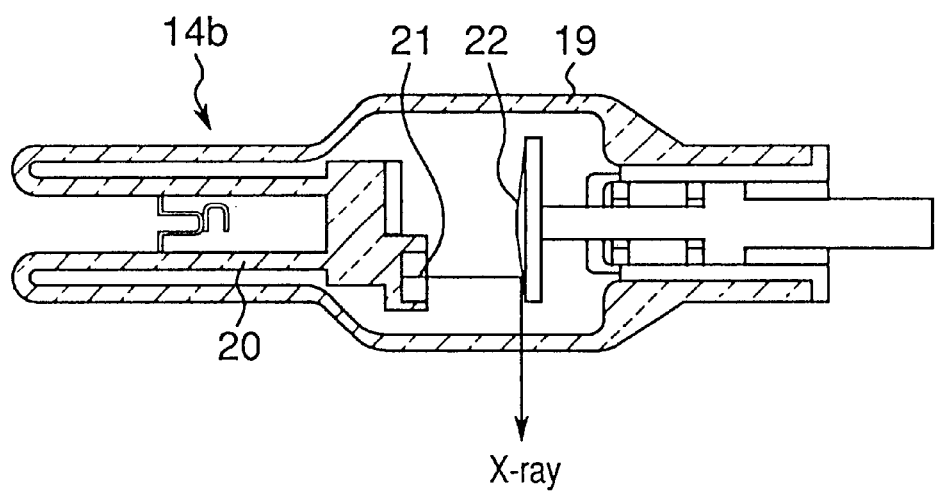
FIG. 3 is a sectional view of a rotating target X-ray tube.

A fixed target X-ray tube 14a shown in FIG. 2 or a rotating target X-ray tube 14b shown in FIG. 3 can be used as the X-ray tube 14.

Figure 4:
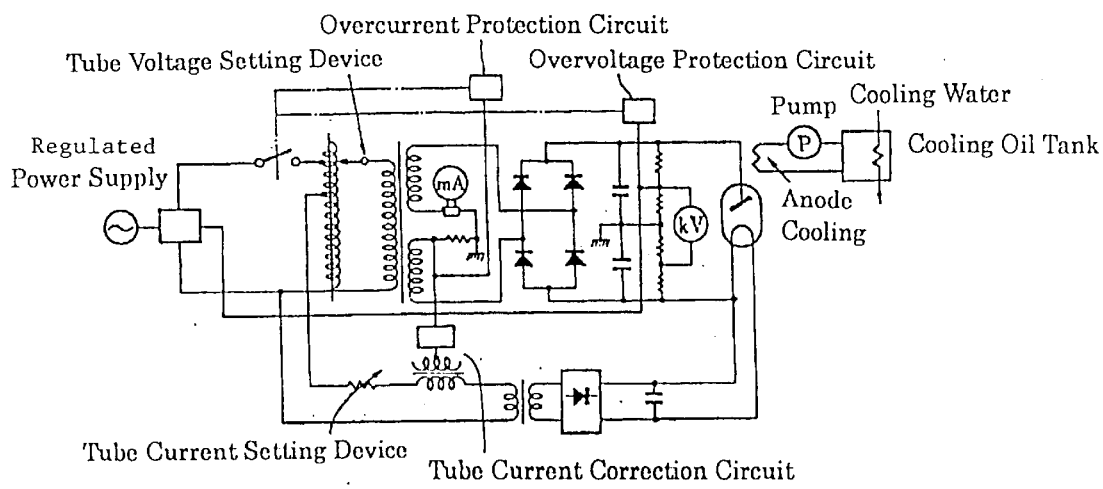
FIG. 4 is a circuit diagram of a continuous X-ray generating circuit.

The fixed target X-ray tube 14a shown in FIG. 2 comprises a glass envelope 19 containing a cathode 21 formed from a filament shrouded by a cover 20 and a target 22 made from a heavy metal, such as tungsten or molybdenum, and tilted about 2° to 20° with respect to the cathode 21. The cathode 21 and the target 22 are connected to power supply terminals. Rearwardly of the target 22 is disposed a cooling nozzle 23 which ejects cooling oil to control the surface temperature of the target 22. When a voltage is applied between the power supply terminals by an electronic circuit shown in FIG. 4 or 5, electrons move from the filament 21 toward the target 22, and X-rays emitted from the target 22 are radiated through a beryllium window 24.

The rotating target X-ray tube 14b shown in FIG. 3 is fundamentally the same as the fixed target X-ray tube 14a shown in FIG. 2, and corresponding parts are designated by same numerals. The rotating target X-ray tube 14b is constructed so that the target 22 rotates at high speed. Since the same portion of the target 22 is not always bombarded with electrons, the temperature rise of the target 22 can be suppressed. Therefore, the oil cooling device is not provided, and the tilting angle of the target 22 is set at 25° to 50°. The surface of the target 22 is formed from two kinds of metals which are disposed alternately, so that when the target 22 is rotated, the two kinds of metals are alternately bombarded with the electrons emitted from the filament 21.

Figure 6:
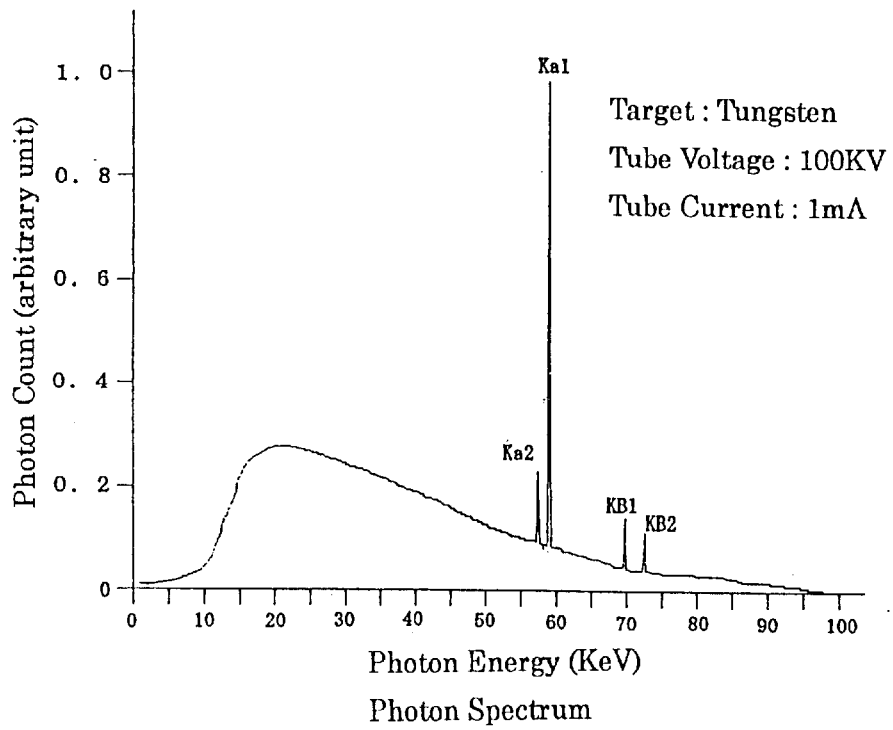
FIG. 6 is a photon spectrum diagram for a tungsten target.
Figure 7:
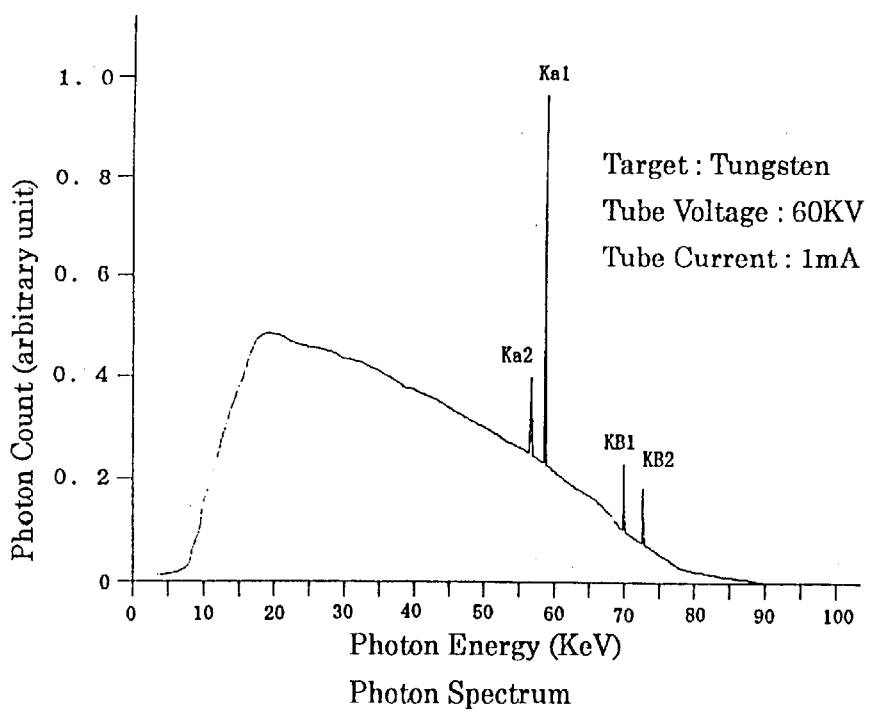
FIG. 7 is a photon spectrum diagram for a tungsten target.
Figure 8:
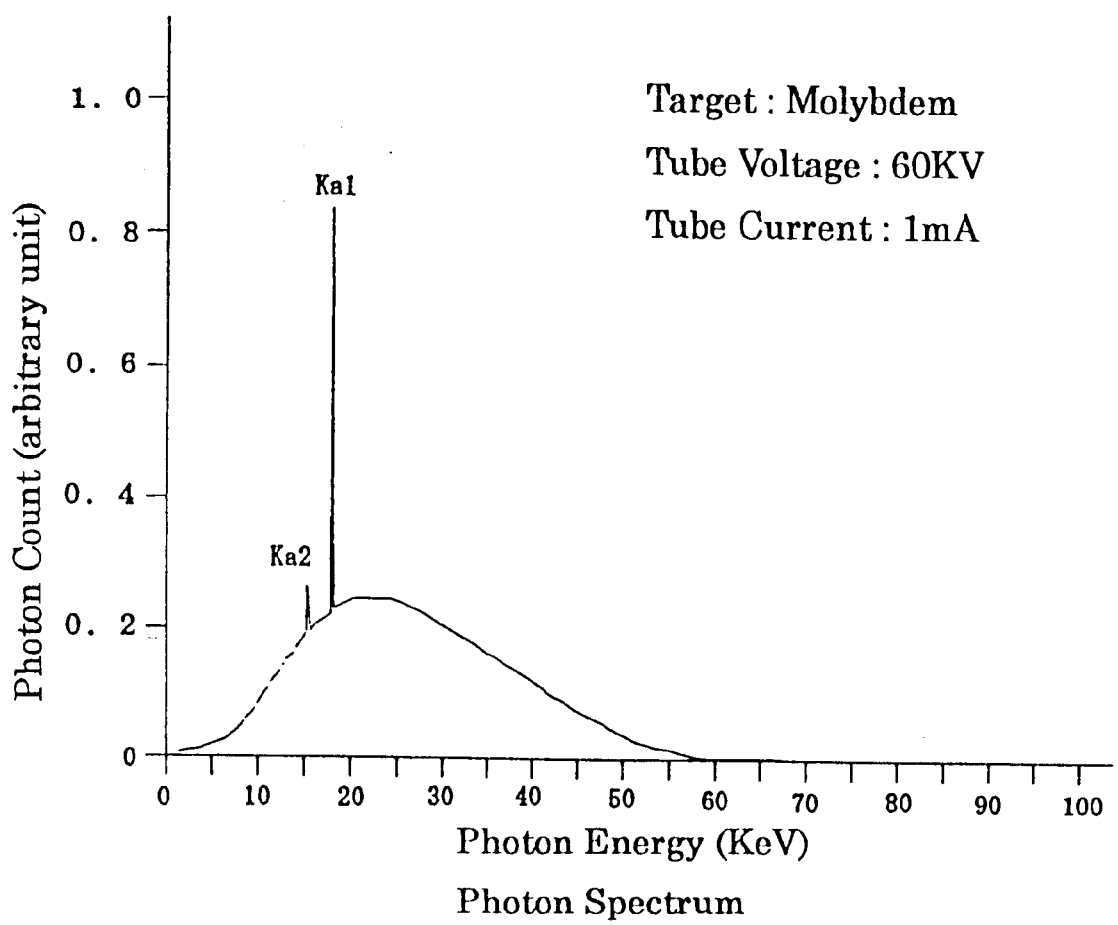
FIG. 8 is a photon spectrum diagram for a molybdenum target.

The material of the target 22 in the X-ray tube 14 greatly affects the intensity characteristics of X-rays. For the tablet inspection apparatus 1 of the present invention, it is preferable to use molybdenum. The reason is that the X-ray intensity needs to be made as weak as possible because the objects to be inspected, i.e., the packaging sheet and tablets, are thin. Further, compared with tungsten, molybdenum has the properties that the absorptance of objects is high, and that the number of photons is large in regions where the photon energy is low, as shown in FIGS. 6 to 8.

Figure 5:
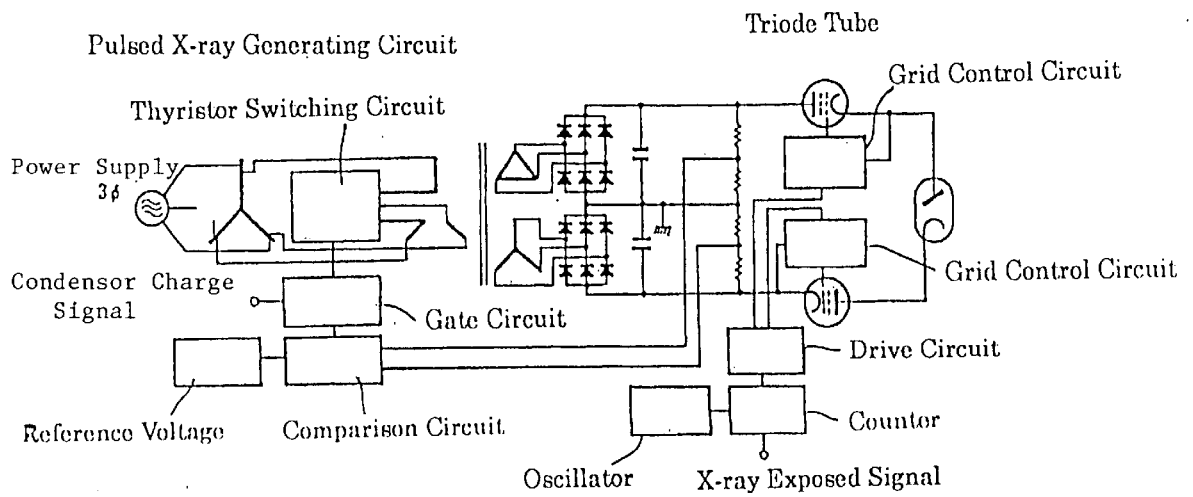
FIG. 5 is a circuit diagram of a pulsed X-ray generating circuit.
Figure 9:
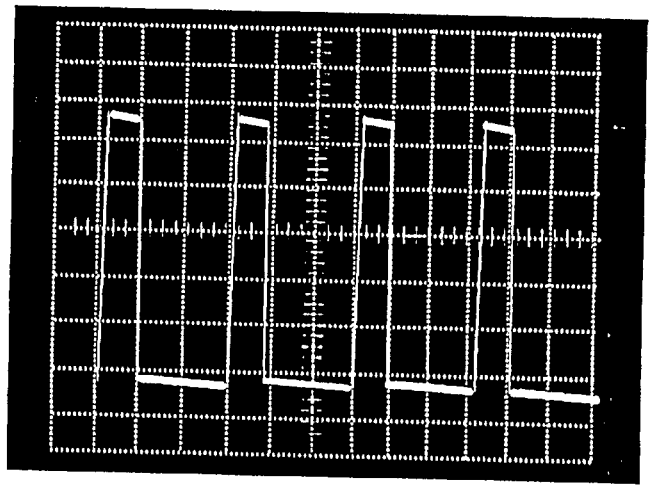
FIG. 9 is a tube voltage waveform diagram.

FIG. 9 shows the tube voltage waveform when X-rays are actually generated from the X-ray tube 14 by using the circuit of FIG. 5. Capacitor terminal voltage during X-ray radiation drops with time due to discharging. The voltage drop $\Delta V(V)$ is $\Delta V(V)=iT/C$, and the tube voltage waveform is thus a sawtooth waveform. To reduce $\Delta V$, the capacitor capacitance should be increased.

If tungsten is used as the material for the target 22, the X-ray intensity can be reduced by lowering the applied voltage. However, in order that detection can be made when the X-ray transmission cannot be confirmed because of foreign matter mixed in the objects to be inspected, X-rays with high photon energy may be applied for a short time in a pulsed manner. In this case, the rotating target X-ray tube 14b shown in FIG. 3 is preferred for use as the X-ray tube. By using two kinds of materials for the target 22, the photon energy can be generated with two different intensities. Specifically, when the tube voltage is lowered by using the tungsten target 22, the photon count increases in a region having a photon energy of 10 KeV to 40 KeV, increasing noise, while the peak of Ka1 decreases, as shown in FIG. 6 and 7. As a result, when the photon energy outside that region reaches a line sensor 16 hereinafter described through an aluminum filter 25 hereinafter described, image blurring occurs.

Figure 10:
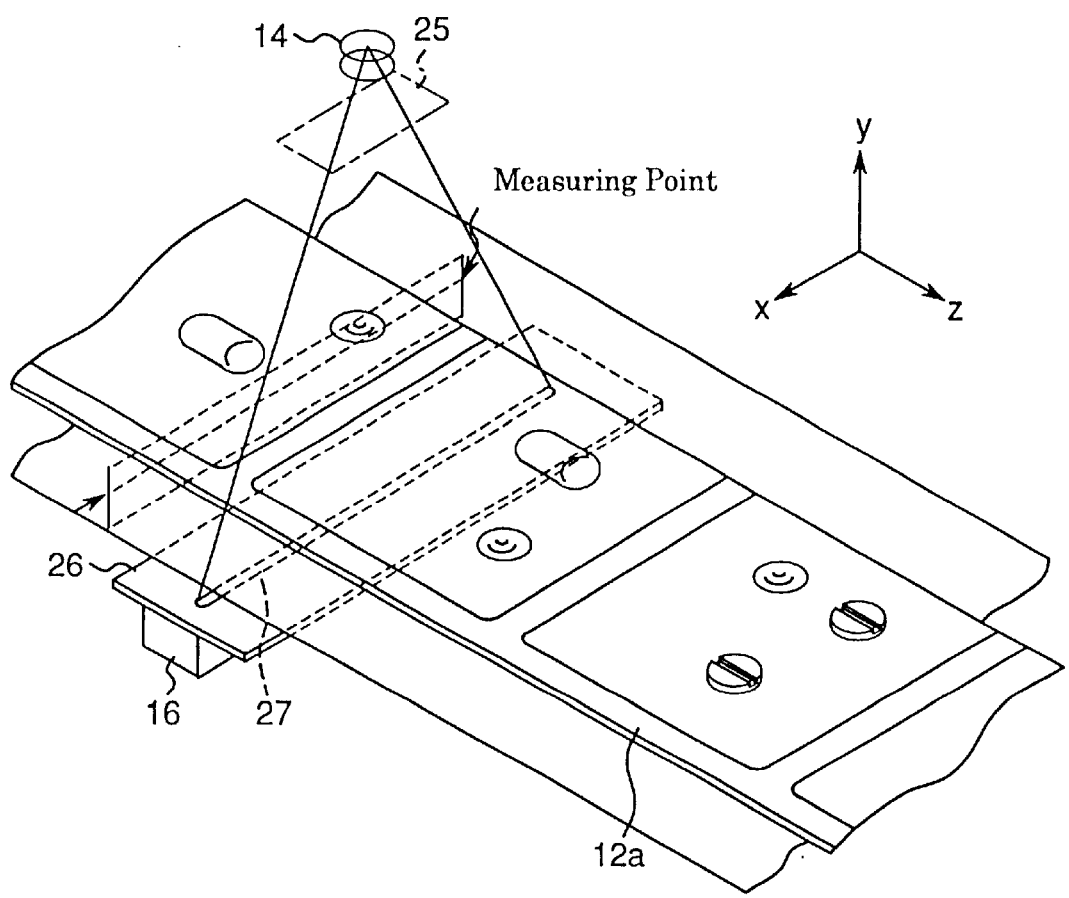
FIG. 10 is a perspective view of the tablet inspection apparatus of FIG. 1.

As shown in FIG. 10, the X-rays emitted from the X-ray tube 14 are radiated through the aluminum filter 25 onto the object to be inspected. The aluminum filter 25 is about 1 mm in thickness, and acts to remove the region of the photon count fluctuation so that the X-rays are radiated in regions where the photon energy is stable. When using a collimator wedge filter, one that matches the shape of the object to be inspected can be used to prevent blurring of tablet edges.

The X-rays radiated on the object to be inspected are sliced by a mask 26 and enter the line sensor 16. As shown in FIG. 10, the mask 26 has a slit 27 extending perpendicular to a conveying direction of the package 12a. The width of the slit 27 is usually about 2 mm. X-rays reaching the portions of the mask 26 other than the slit 27 are blocked, and only the X-rays passed through the slit 27 enter into the line sensor 16.

Figure 11:
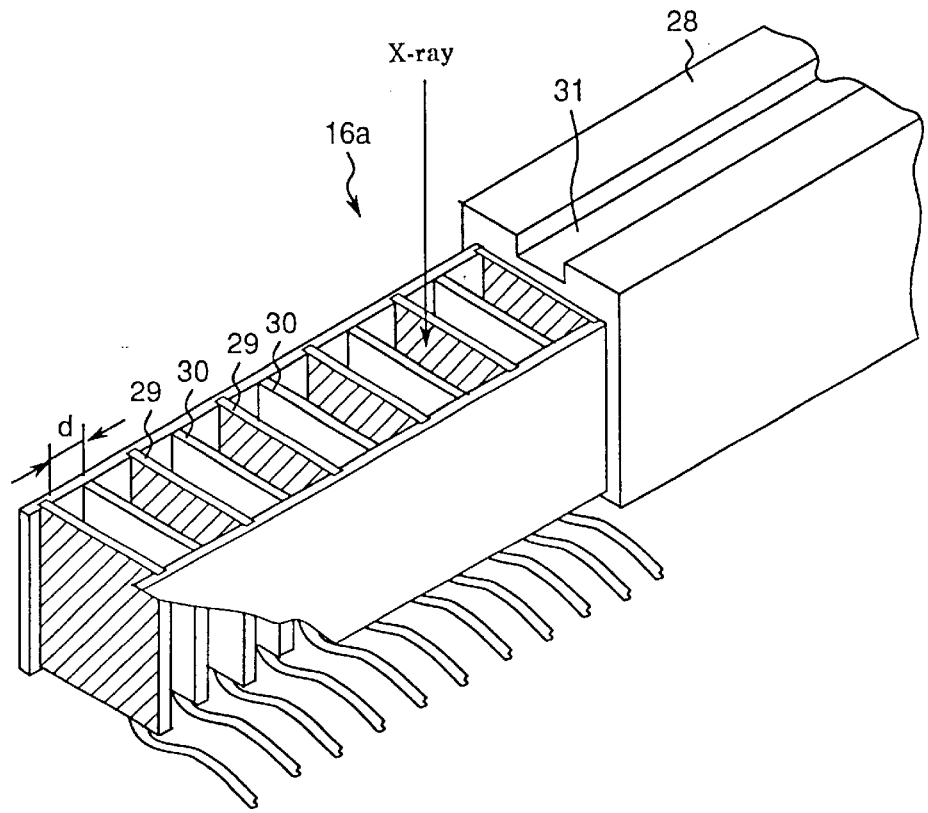
FIG. 11 is an exploded perspective view of a line sensor (ionization chamber detection device)

An ionization chamber detection device 16a or a semiconductor detection device 16b is used as the line sensor 16. As shown in FIG. 11, the ionization chamber detection device 16a comprises plate-like bias electrodes 29 and signal electrodes 30 alternately spaced apart from one another by a distance d in a container 28. Xenon gas is filled in the space between the respective electrodes 29 and 30 at a pressure of 10 p (atm). With a voltage applied between the bias electrodes 29 and the signal electrodes 30, when the X-rays enter through a recess 31 formed in the upper surface of the container 28 and the gas is ionized, a minute current flows between the electrodes 29 and 30. This current is detected in numerical form.

Characteristic conditions of the line sensor 16 are obtained in the following manner.

Assuming that ionization occurs uniformly in the parallel-plate ionization chamber by the X-rays, we consider the limit of ion pair collection where the electric field in the ionization chamber becomes zero because of the effects of space charge. When ions occur in quantities of $n_0/cc/s$, the ion charge density at point x is given by the following equation.

$$\rho_+ = n_+ e = \frac{n_0(d-x)e}{w_+} \qquad \text{[Equation 1]}$$

Here, $w_+$ is the ion flowing speed. When the electric field is denoted by E, the gas pressure by P, and the ion moving speed by $\mu_+$, the ion flowing speed $w_+$ is given by the following equation 2. Poisson's equation expressing the electric field is shown as in the equation 3.

$$w_+ = \frac{\mu_+}{P} E \qquad \text{[Equation 2]}$$

$$\nabla \cdot E = 4\pi\rho \qquad \text{[Equation 3]}$$

$\mu_+$ is an inherent value in gas, and is 0.58 for Xe (xenon). By substituting the equation 2 into the equation 1 and giving the boundary conditions that yield E=0 for x=d by the effects of space charge, we have the following equation.

$$E = \left(\frac{4\pi P n_0 e}{\mu_+}\right)^{\frac{1}{2}} (d-x) \qquad \text{[Equation 4]}$$

Potential difference V between the electrodes is obtained by integrating the equation 4 in the range of x=0 to x=d.

$$V_s = \int_0^d E\,dx = \frac{1}{2}\left(\frac{4\pi Pn_0 e}{\mu_+}\right)^{\frac{1}{2}} d^2 \quad \text{[Equation 5]}$$

That is, assuming that ionization occurs uniformly in the parallel-plate ionization chamber when subjected to the radiation of X-rays, the potential difference Vs necessary to collect a charge of $n_0 e$ is limited by the space charge if the potential difference is smaller than the Vs defined by the equation 5.

Although the equation 5 is expressed in the CGS system, if $\mu_+$[cm²/V/s] and d[cm], we have the following equation using rationalized unit, where I is the output current (A) of the ionization chamber, and D is the effective volume (cm) of the ionization chamber.

$$v_s = 1.67 \times 10^6 \left(\frac{PI}{\mu_+ D}\right)^{\frac{1}{2}} d^2 \quad \text{[Equation 6]}$$

The more the output current I increases, the higher the potential difference Vs becomes. Therefore, the applied voltage must be set so that saturation is reached at the largest output current. Especially, when the gas pressure is high, since the charge density becomes higher in areas within the ionization chamber near the X-ray entrance window, a higher potential than the potential Vs calculated using the average charge density is necessary. When radiating X-rays in a pulsed manner, not only the saturation characteristic as the static characteristic is required, but the fast step response characteristic is also required. Recent tablet packaging machines, such as the tablet packaging machine 2 of the present invention, are capable of packaging 90 doses per minute. In that case, a range of 114 mm must be inspected in one minute. To achieve this requirement, the X-rays must be emitted at intervals of 5 ms. This will not be a problem since the rising time of X-rays is about 0.1 to 0.2 ms. It should, however, be noted that the rising characteristic of the line sensor 16 is determined by the ion flowing speed.

Here, we consider the rising characteristic of the output current I at the collector electrode when ion pairs are produced uniformly in the ionization chamber of electrode spacing d at a rate of $n_0$cc/s for $t \geq 0$. The rate of change of the ion density in the entire ionization chamber at time t is given by the following equation.

$$\frac{dN_+}{dt} = N_0 - n_+ w_+ S \quad \text{[Equation 7]}$$

Here, the first term on the right-hand side represents ion production and the second term the amount of ions reaching the collector electrode. $N_o$ represents $n_0 d \cdot S$, where S is the electrode plate area. $n_+$ represents the density of ions reaching the collector electrode, which increases at an ion producing rate per second until the ions produced at x=0 at the time t=0 reach the collector electrode, but thereafter it levels off, as shown in the following equation,.

$$\frac{dn_+}{dt} = \begin{cases} n_0 & 0 \leq t \leq \frac{d}{w_+} \\ 0 & \frac{d}{w_+} < t \end{cases} \quad \text{[Equation 8]}$$

Solving the equation 8 and substituting the boundary conditions yield the following equation.

$$n_+ = n_0 t \quad 0 \leq t \leq \frac{d}{w_+} \quad \text{[Equation 9]}$$
$$n_+ = \frac{n_0 d}{w_+} \quad \frac{d}{w_+} < t$$

Substituting the equation 9 into the equation 7, $N_+$ is obtained as shown in the following equation.

$$N_+ = N_0\left(t - \frac{w_+}{2d}t^2\right) \quad 0 \leq t \leq \frac{d}{w_+} \quad \text{[Equation 10]}$$
$$N_+ = \frac{N_0 d}{2w_+} \quad \frac{d}{w_+} < t$$

The same equations as given above hold for electrons. However, since the electron flowing speed $w_-$ is much faster than that of ions, when the rising characteristic due to the ion moving time is considered, there is no objection to defining $N_-$ as follows.

$$N_- = \frac{N_0 d}{2w_-} \quad \text{[Equation 11]}$$

The output current I is given by $$I = \frac{N_+ e w_+}{d} + \frac{N_- e w_-}{d} \quad \text{[Equation 12]}$$

Substituting the equations 10 and 11 into the above equation yields the following equation.

$$I = \frac{N_+ e w_+}{d}\left(t - \frac{w_+}{2d}t^2\right) + \frac{N_0 e}{2} \quad 0 \leq t \leq \frac{d}{w_+} \quad \text{[Equation 13]}$$
$$I = N_0 e \quad \frac{d}{w_+} < t$$

Figure 12:
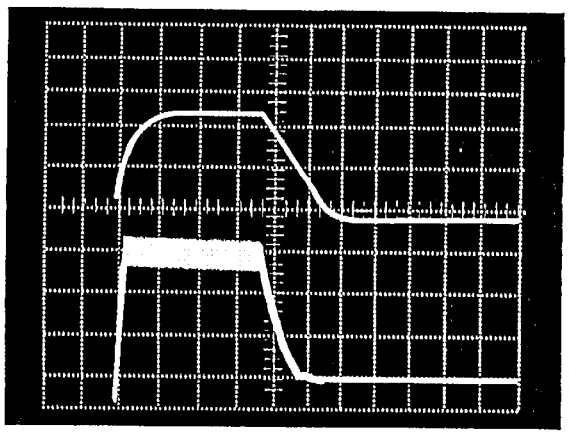
FIG. 12 is a waveform diagram showing the response characteristics of the ionization chamber.

Thus, it can be seen that the rising time of the output current of the line sensor 16 is expressed by the interelectrodes moving time $d/w_+$ of the ions. The actually measured results are shown in FIG. 12. The applied voltage V that makes the output current rising time $d/w_+$ equal to the X-ray rising time to is represented by the following equation, and it is proportional to the pressure p and the square of the electrode spacing d.

$$V = \frac{pd^2}{\mu_+ t_0} \quad \text{[Equation 14]}$$

Figure 13:
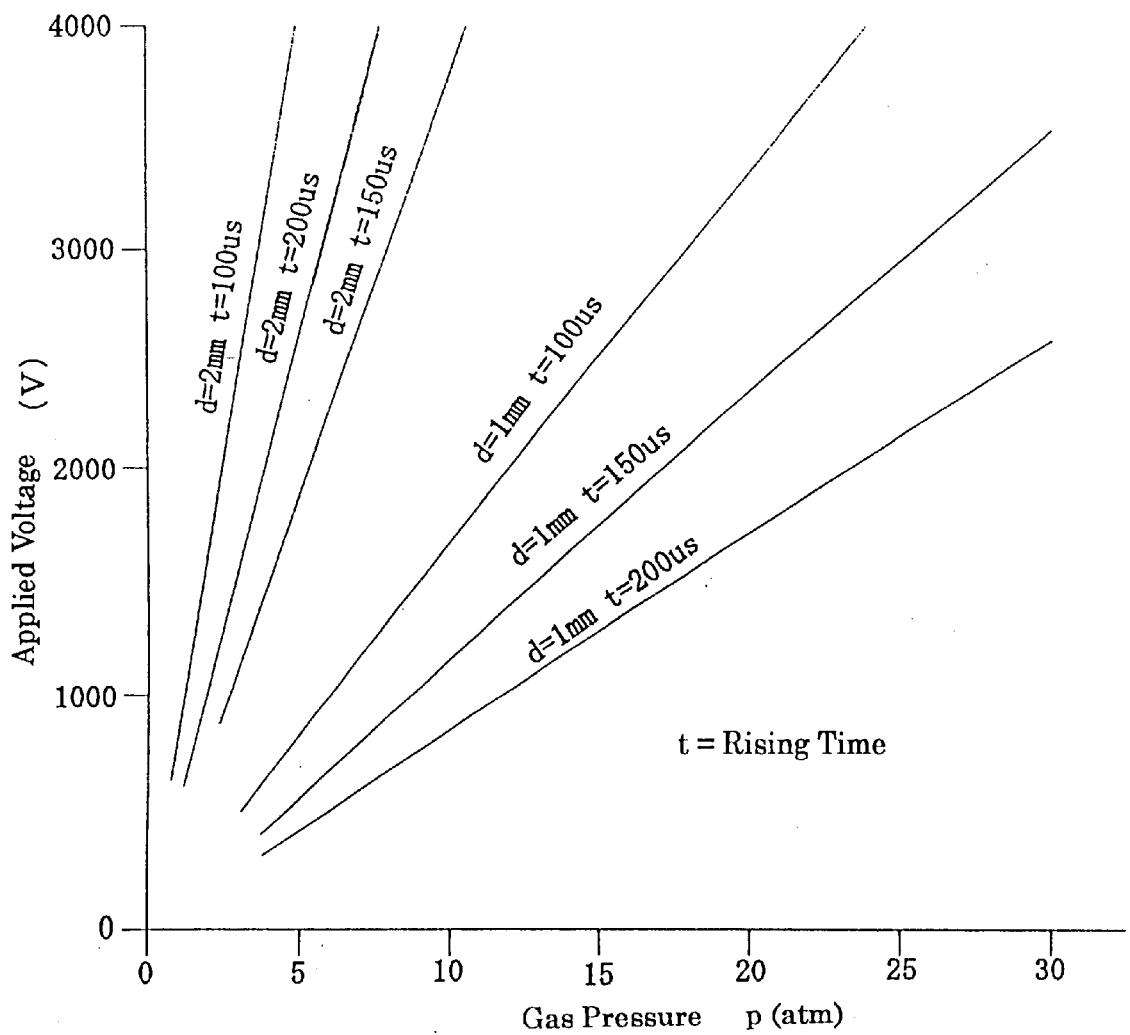
FIG. 13 is a graph showing the relationship between gas pressure and applied voltage in the ionization chamber.

These relations are shown in FIG. 13. For a faster detection speed at a low voltage, for example, the electrode spacing d is set at 1 mm, the gas pressure p at 10 atm, and the applied voltage V at 1500 V. This achieves a rising time t of 100 µs.

Figure 14:
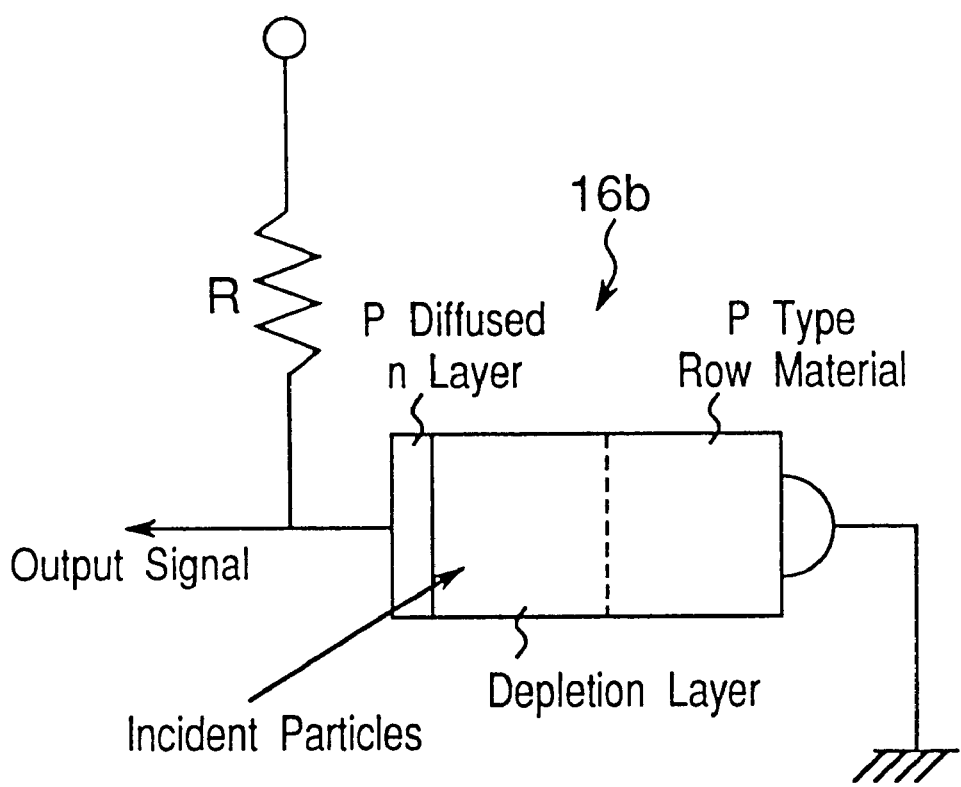
FIG. 14 is a simplified schematic diagram of a line sensor (semiconductor radiation detecting device)

For the semiconductor radiation detection device 16b, the p-n junction type shown in FIG. 14 can be used. When X-rays are incident between the junctions of the device, an output signal consisting of electric current pulses is produced. Besides the p-n junction type, the p-i-n junction type can also be used. When such semiconductor radiation detection device 16b is used, a compact, multi-channel detector with good output linearity can be constructed.

The principle of the detection by the line sensor 16 will be described below. The objects to be detected include spatially nonuniform capsules and spatially substantially uniform tablets. To reproduce a plane within a certain range by transmitting X-rays through the package 12a containing such objects, generally imaging data taken from all directions passing through every point contained in the plane becomes necessary. However, from discretely finite imaging data also, a reproduced image can be obtained within the permissible range. Of course, in this case, there occurs a difference in the accuracy of the reproduced image between the spatially uniform tablets and the spatially nonuniform capsules. In the case of objects such as tablets except the case of doughnut-shaped troches, since their outer shape is relatively simple, X-rays from a certain direction are not transmitted more than once through the object being inspected. The image can therefore be reproduced by considering the absorptance when the X-rays pass through the tablet.

Figure 15:
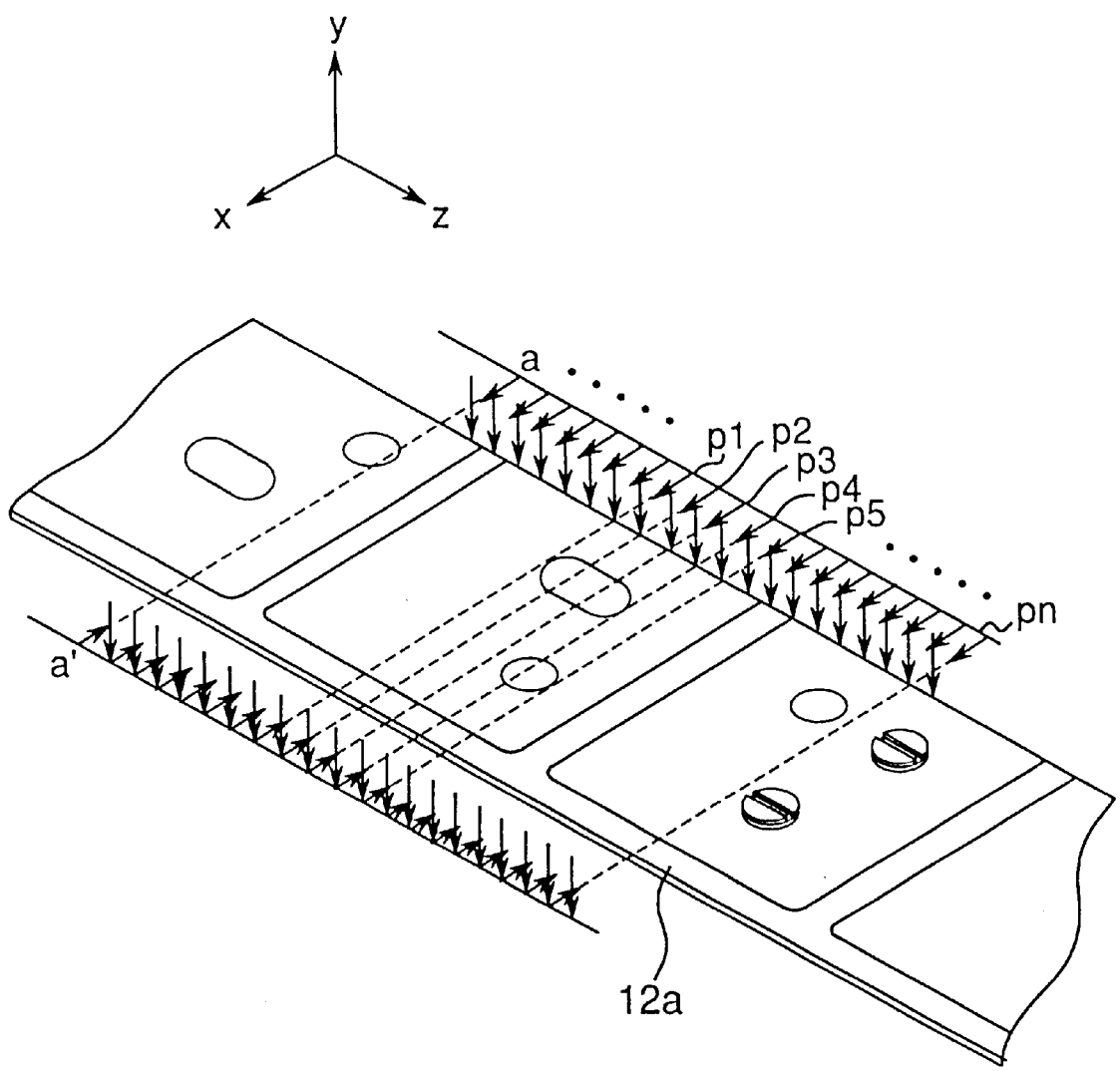
FIG. 15 is a perspective view of a packaging sheet for explaining measurement points.
Figure 16:
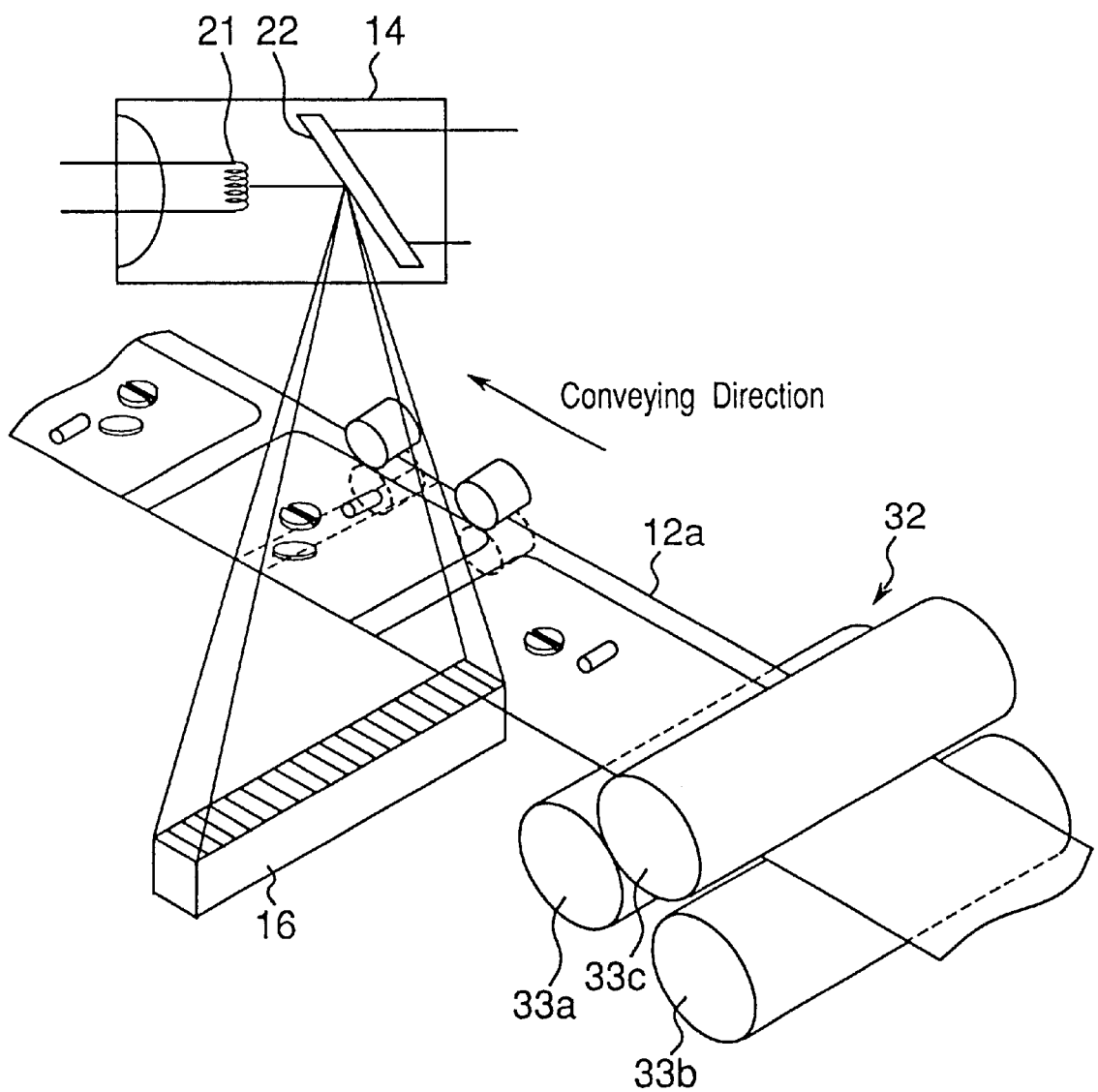
FIG. 16 is a perspective view of a tablet detection apparatus in FIG. 10 equipped with a separating device.

Assuming that the package 12a is transported in a z(-) direction in a horizontal plane x-z in a three-dimensional space defined by three axes (x, y, z), as shown in FIG. 15, the line sensor 16 is disposed along a line a–a' extending parallel to the x-axis direction. If one tablet overlaps another in the package 12a, it is difficult to determine tablet count and tablet shape. It is, therefore, desirable that a separating device 32 for separating the tablets contained in the package 12a is provided at a position before the radiation exposure position, as shown in FIG. 16. The separating device 32 comprises two sponge rollers 33a and 33b disposed side by side below the package 12a and a sponge roller 33c disposed above the package 12a. The separating device 32 is constructed to separate overlapping tablets by passing the package 12a in undulating fashion between the upper and lower rollers. The component members of the separating device 32 are not limited to the three sponge rollers 33a, 33b, and 33c, but more than three sponge rollers may be used.

As the package 12a is transported, the line sensor 16 detects the amount of transmission through the package 12a at each of X-ray radiation exposure points p1, p2, p3, . . . , pn. In the present embodiment, the pitch of the X-ray radiation exposure points p1, p2, p3, . . . , pn is 0.76 mm, as shown in FIG. 17.

Figure 17:
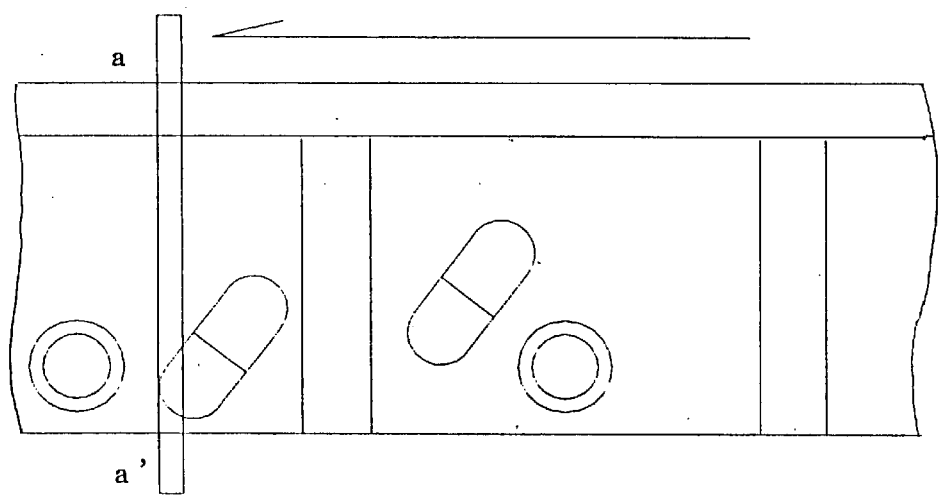
FIG. 17 is a plan view for explaining the pitch of radiation exposure points.
Figure 17:
Figure 18:
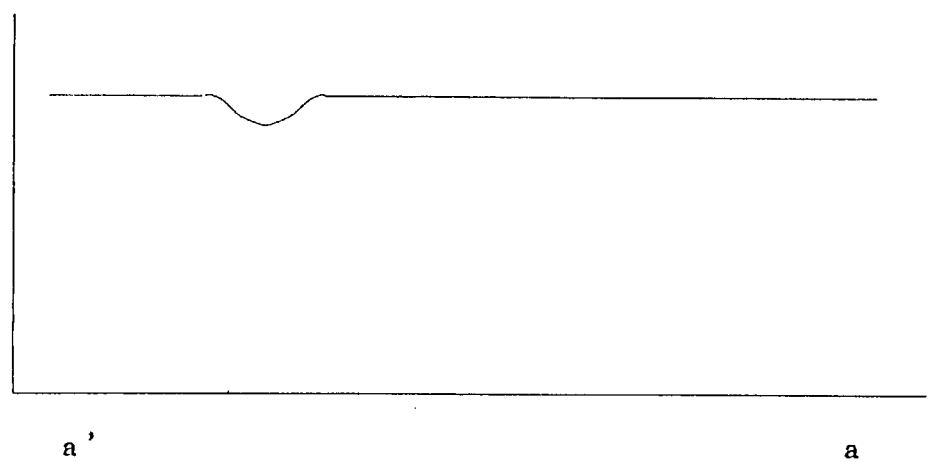
FIG. 18 is a graph showing the transmission amount output data of the line sensor.
Figure 19:
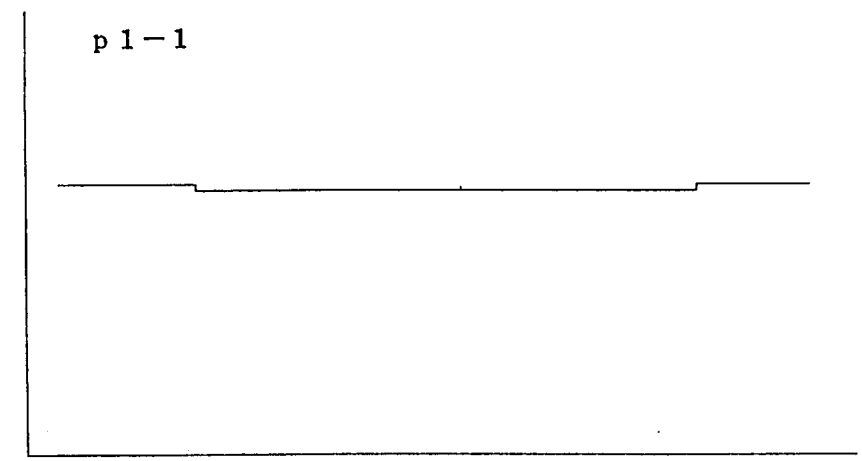
FIG. 19 is a graph showing the transmission amount output data of the line sensor.
Figure 19:
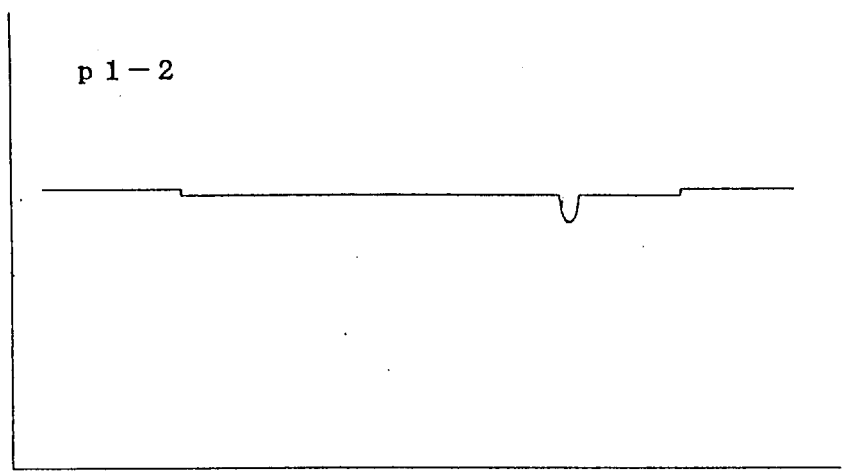
Figure 19:
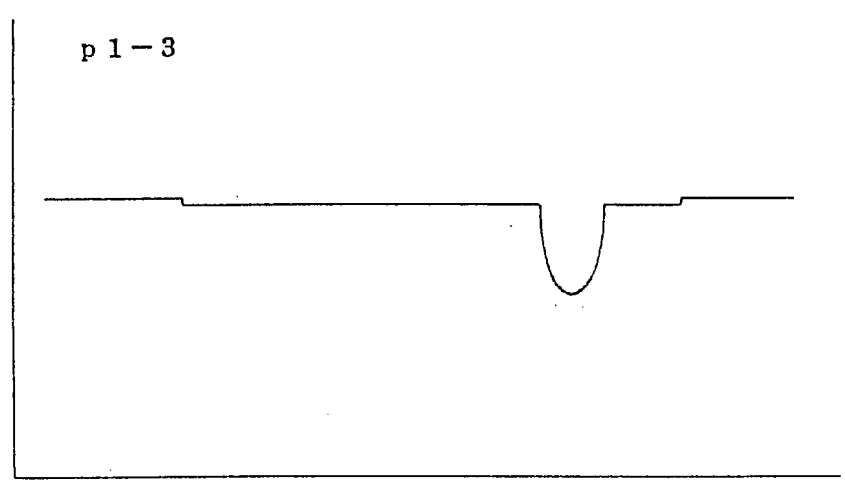
Figure 20:
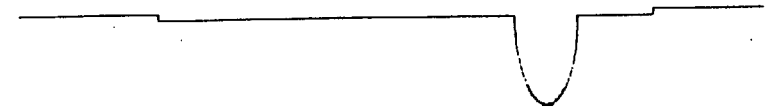
FIG. 20 is a graph showing the transmission amount output data of the line sensor.
Figure 20:
Figure 20:
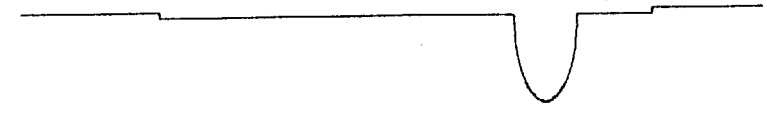
Figure 21:
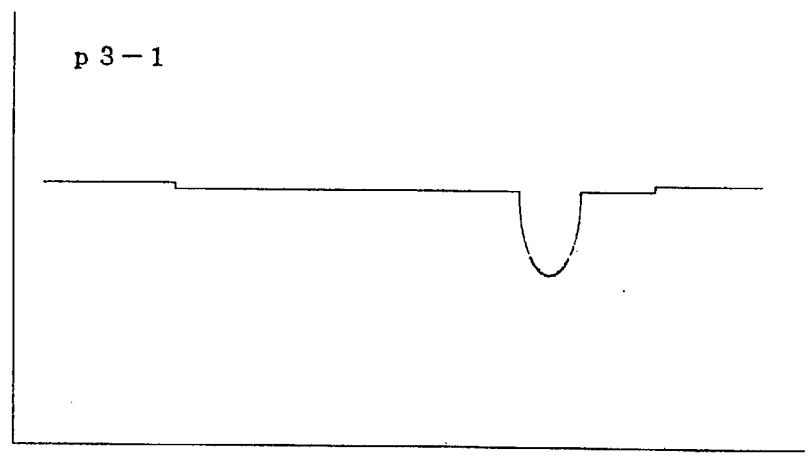
FIG. 21 is a graph showing the transmission amount output data of the line sensor.
Figure 21:
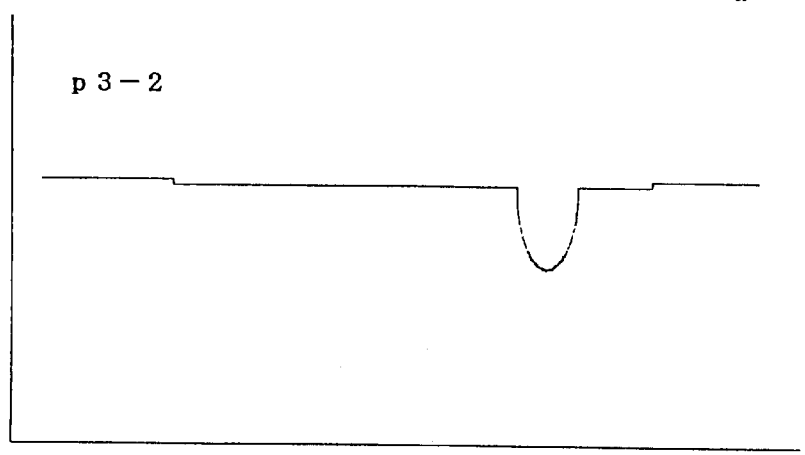
Figure 21:
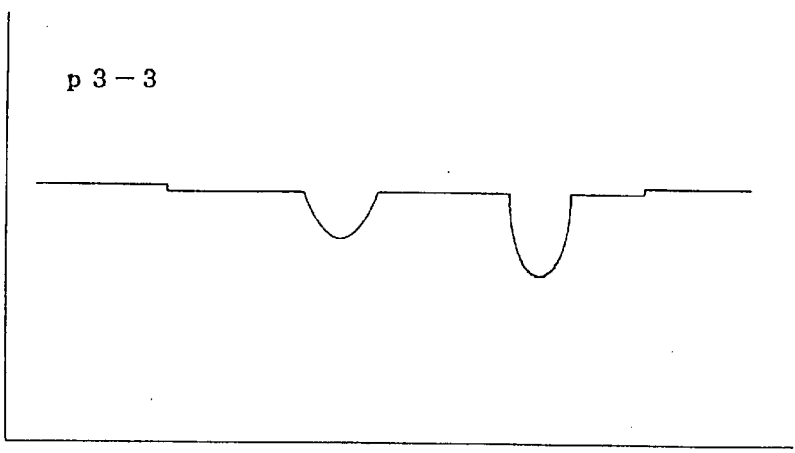
Figure 22:
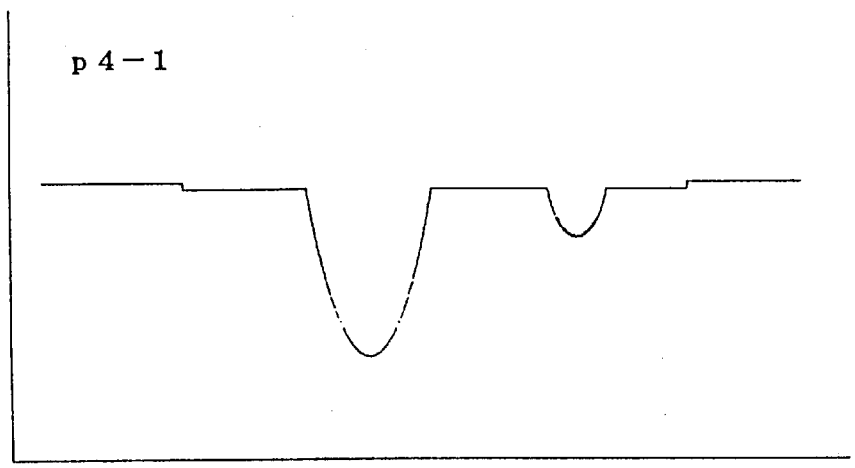
FIG. 22 is a graph showing the transmission amount output data of the line sensor.
Figure 22:
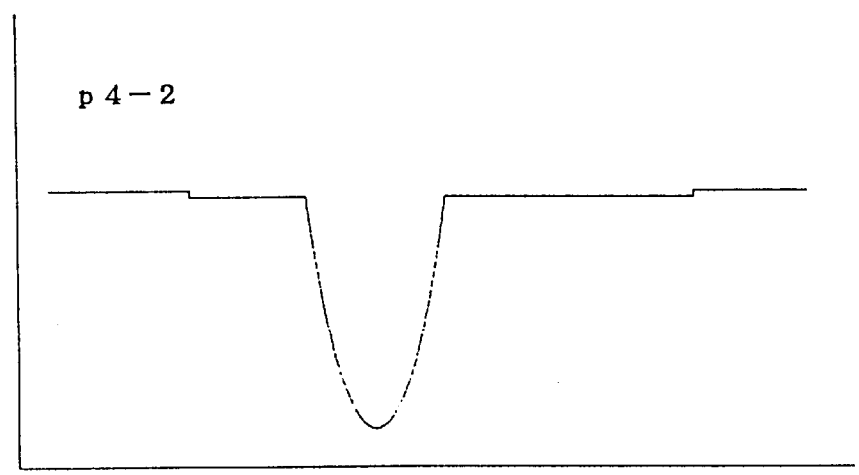
Figure 22:
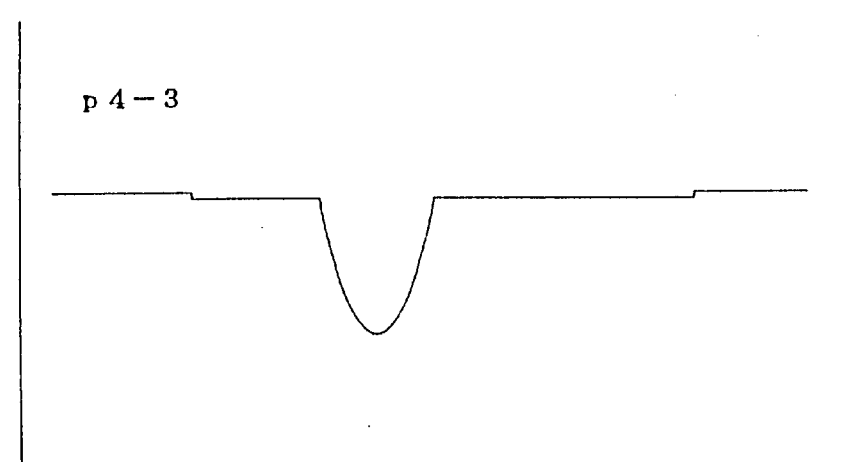
Figure 23:
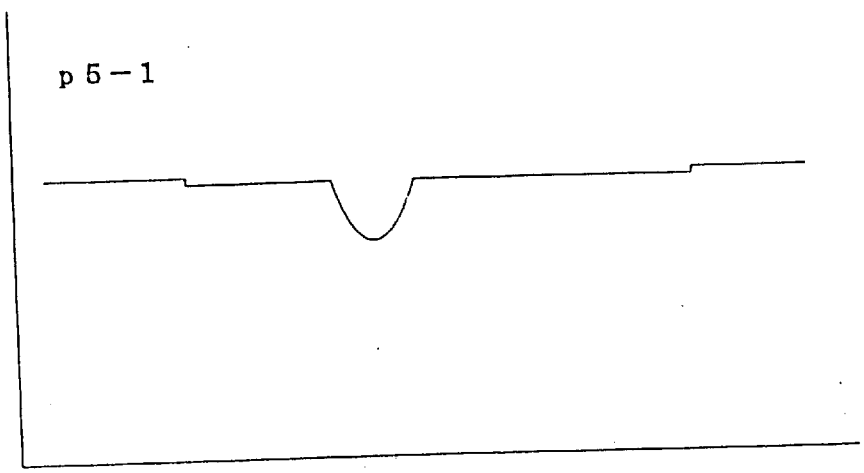
FIG. 23 is a graph showing the transmission amount output data of the line sensor.
Figure 23:
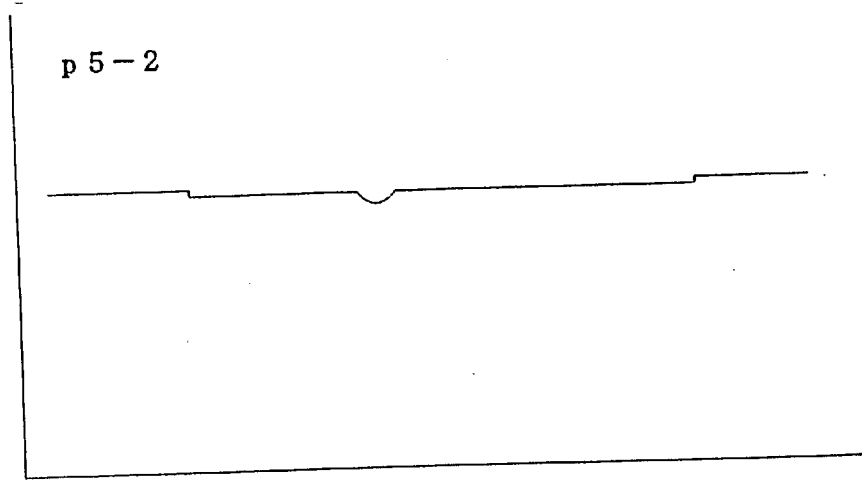
Figure 23:
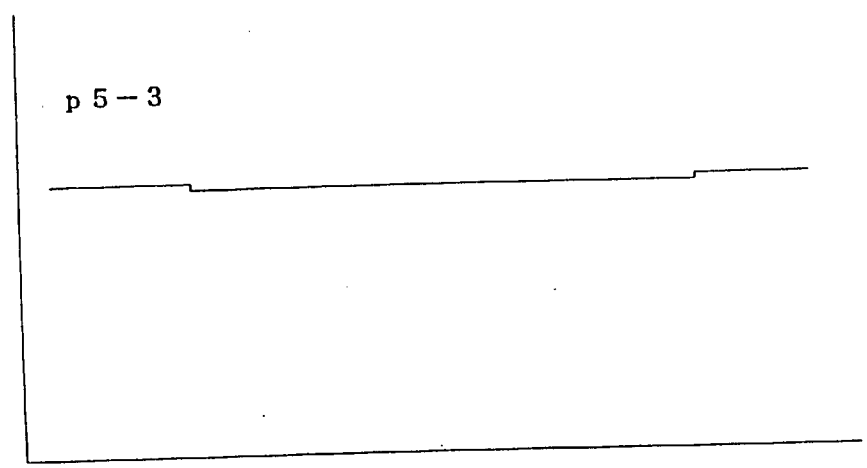

When a capsule is located at a radiation detection point of the line sensor 16, as shown in FIG. 17, the X-ray transmission amount detected by the line sensor 16 is as shown in the graph of FIG. 18.

Figure 24:
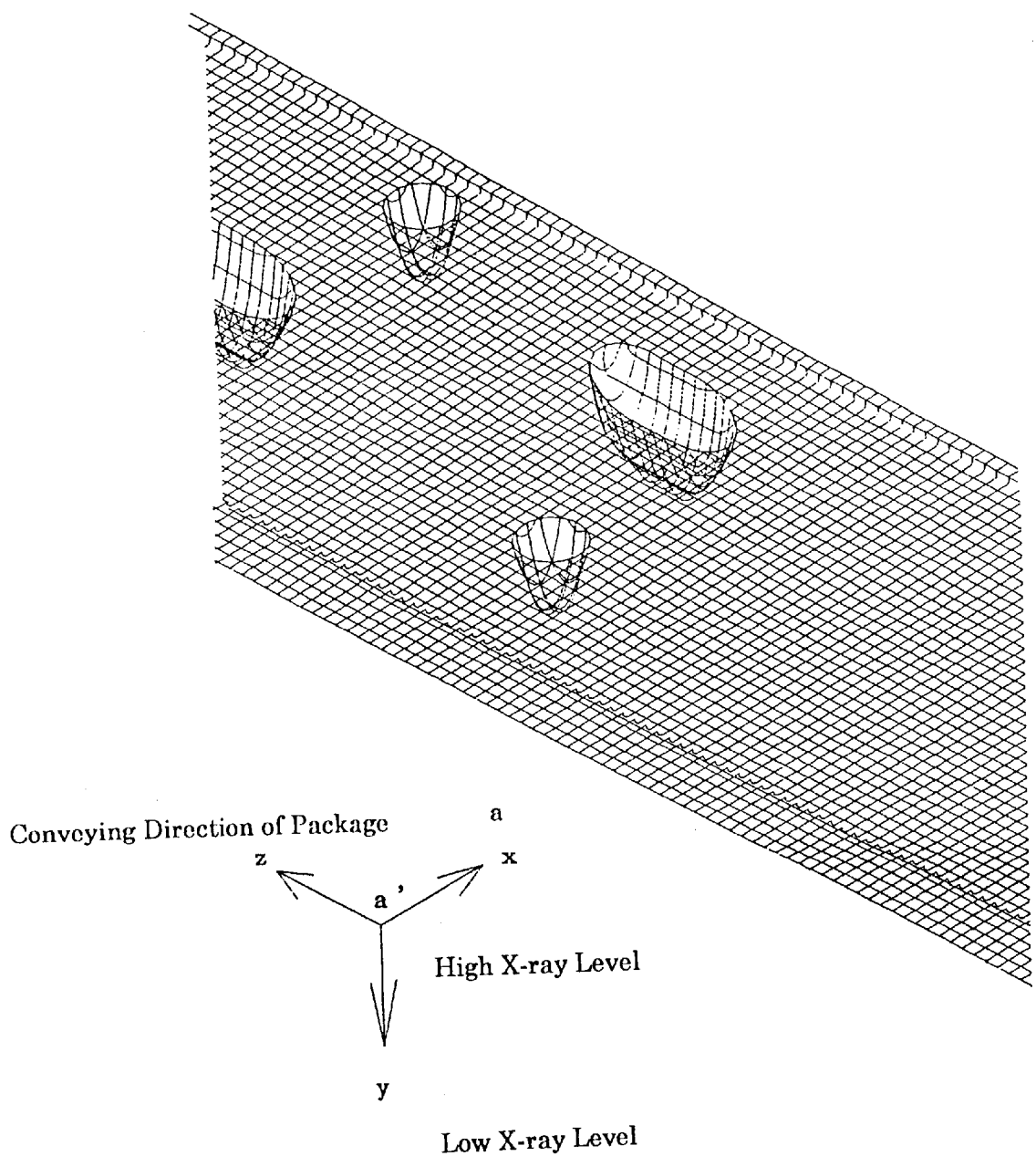
FIG. 24 is a three-dimensional graph showing X-ray attenuation characteristics.

FIGS. 19 to 23 show graphs of X-ray transmission amounts at the radiation exposure points p1, p2, p3, p4, and p5 in the case of the package 12a containing a capsule and a tablet, as shown in FIG. 15. For simplicity, each point is shown for every two points. In FIGS. 19 to 23, at point p1-1, the attenuation of the X-ray transmission amount due to the package 12a alone is detected; at point p1-2, the attenuated portion of the X-ray transmission amount due to the edge of the capsule is beginning to appear; and at points p1-3 to p3-2, a large attenuation due to the center portion of the capsule is observed. At point 3-3, the attenuated portion of the X-ray transmission amount due to the tablet is beginning to appear, and at point p4-1, the attenuation of the X-ray transmission amount due to the capsule decreases. At points p4-2 to p5-2, only the tablet contributes to the attenuation of the X-ray transmission amount, and at point 5-3, the attenuation of the X-ray transmission amount due to the package 12a alone is detected. A three-dimensional representation of the attenuation data shown in FIGS. 19 to 23 is given in the graph of FIG. 24.

Figure 25:
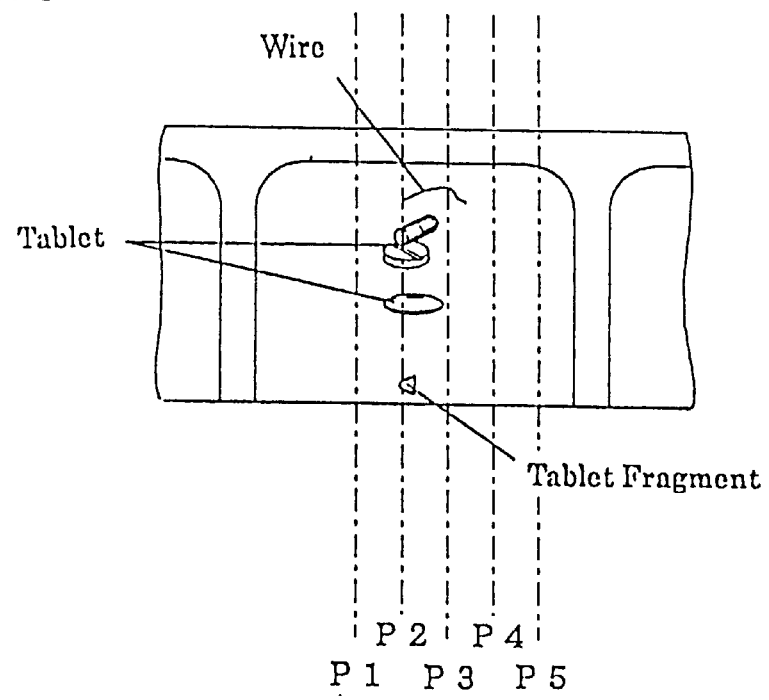
FIG. 25 is a plan view showing measurement points in the case of a defective package.
Figure 26:
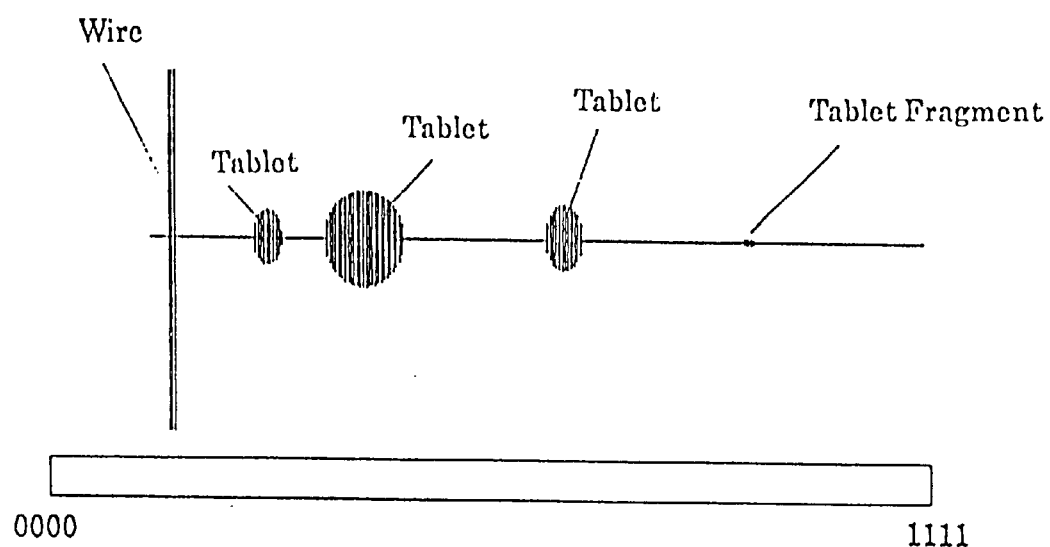
FIG. 26 is a graph showing attenuation widths of the transmission amount output data of the line sensor.
Figure 27:
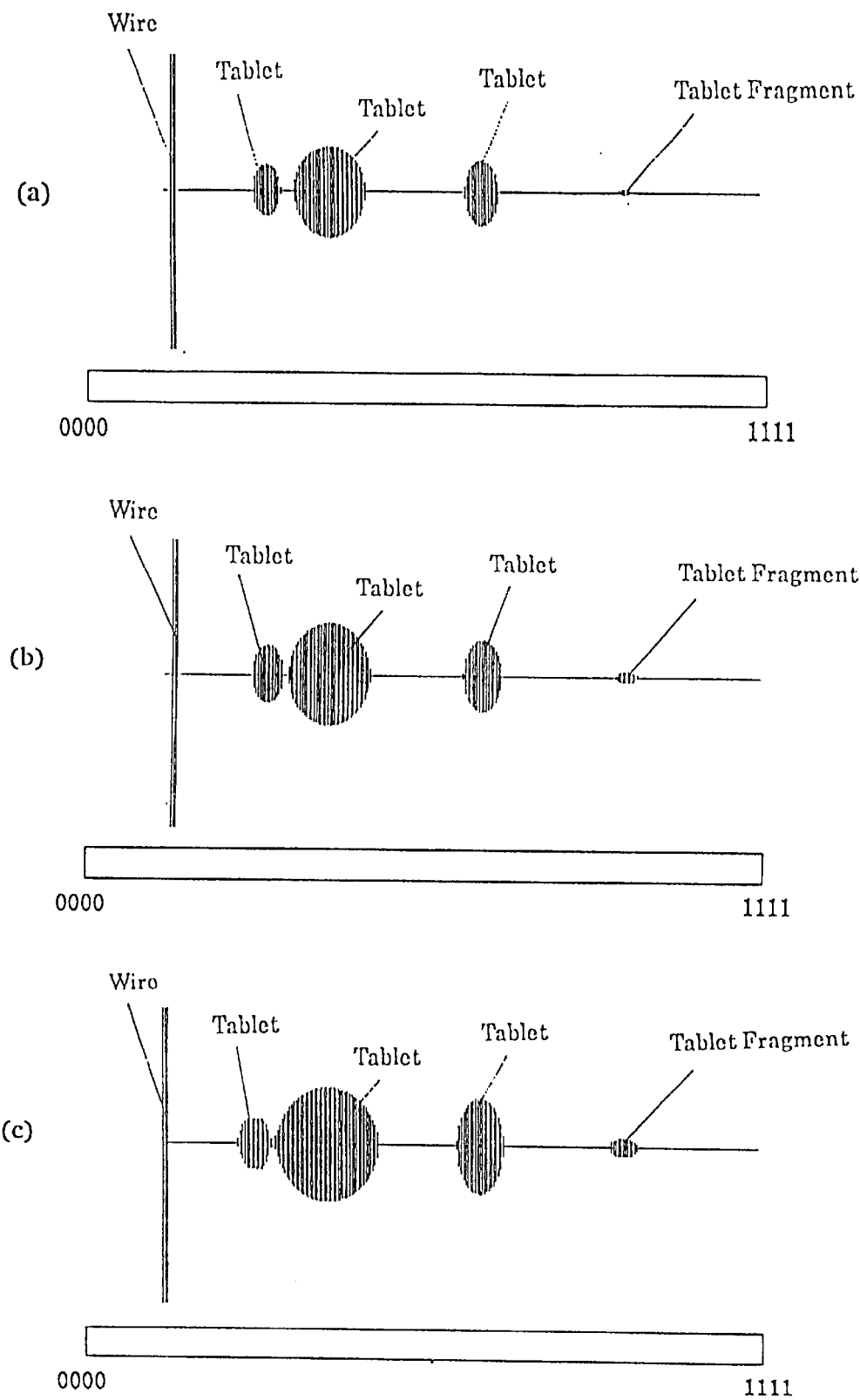
FIGS. 27(a–c) show graphs of attenuation widths of the transmission amount output data of the line sensor.

FIG. 25 shows another case where a wire and a tablet fragment, which constitute factors of packing defects, are contained in the package 12a. In this case also, X-ray transmission amounts are likewise detected, and attenuation widths are obtained tom the attenuation data. When the centers of the attenuation widths are aligned along an axis, the graphs shown in FIGS. 26 and 27 (a–c) are obtained. In the graphs, the abscissas 0000 to 1111 are coordinate positions where detections are made by the line sensor 16, and the ordinates represent the attenuation width.

Figure 28:
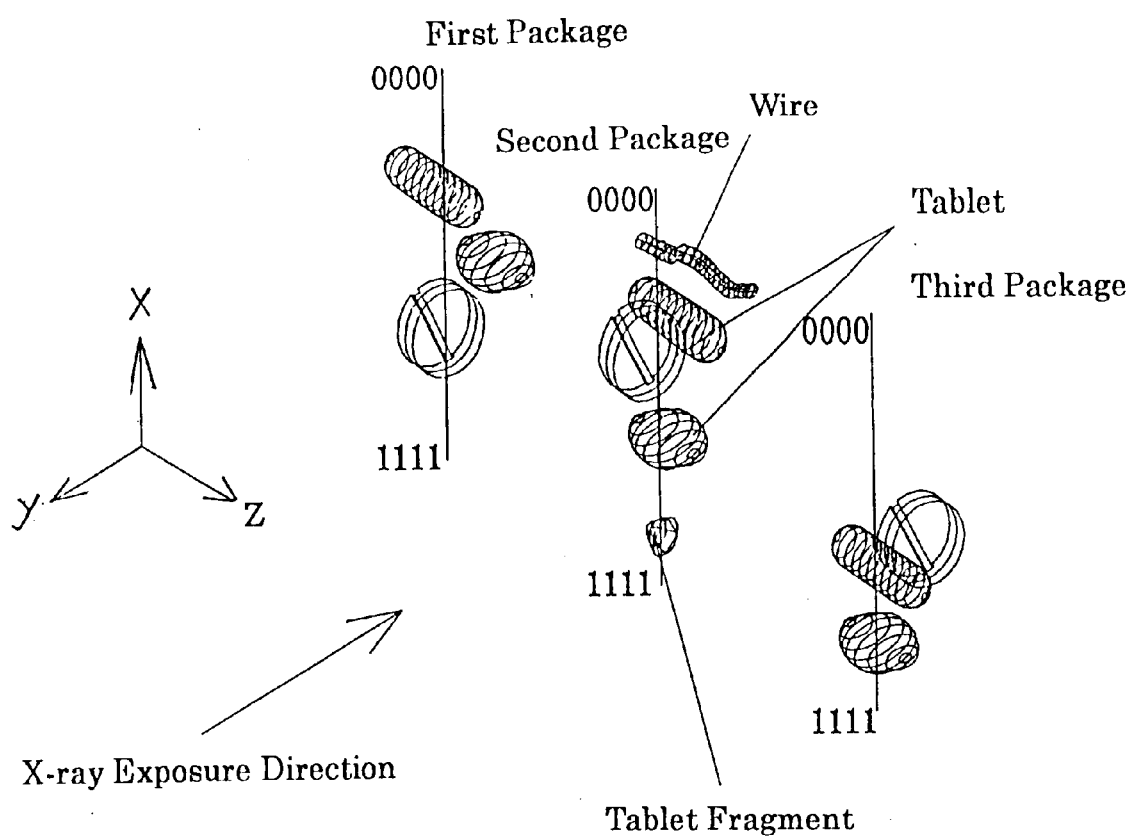
FIG. 28 is a diagram showing three-dimensional image data.

Next, the amount of attenuation due to the package 12a is subtracted from the attenuation data of the X-ray transmission amount. After processing for noise elimination, edge enhancement, and the detection of attenuation amount center values is performed, the data are reordered by aligning the centers of the attenuation amounts. As a result, the graphic image shown in FIG. 28 is obtained. In the present embodiment, since the attenuation of the X-ray transmission amount can only be detected in the thickness direction, i.e., in the y direction, if an image of overlapping tablets is reproduced, the reproduced image represents the overall shape of the overlapping tablets.

The graphic image of FIG. 28 is shown by simply assuming that the X-ray absorptance of each tablet is ½. Actually, the image contains distortion in the y-axis direction because the X-ray absorptance of the tablet differs from type to type. This distortion can be corrected by multiplying with a distortion factor after identifying the tablet type.

Distortion in the y-axis direction is not so serious problem as to render the identification of the tablet impossible. The reason is as follows. Since the type of the packaged medicine is known in advance from the prescription data, shape data can be created by reading from a storage device the X-ray absorptance data for the medicine supposed to have been packaged, and by correcting the detection data of the X-ray transmission amount based on the absorptance data. It is then only necessary to verify whether the thus created shape data matches the shape data of the packaged tablet. If they do not match, there is high possibility that the packaged medicine is wrong.

Figure 29:
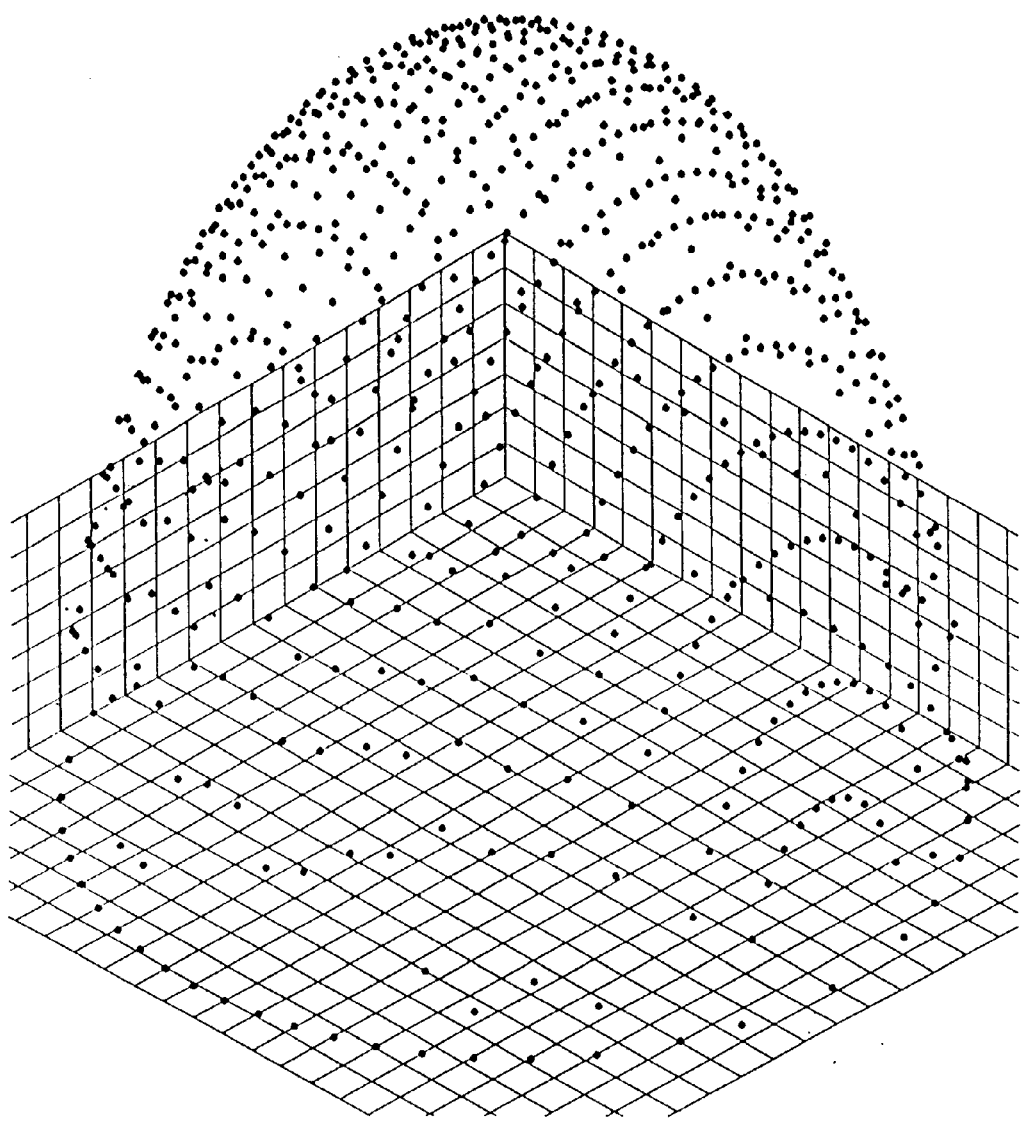
FIG. 29 is a three-dimensional graph showing one example of verification criteria data.
Figure 30:
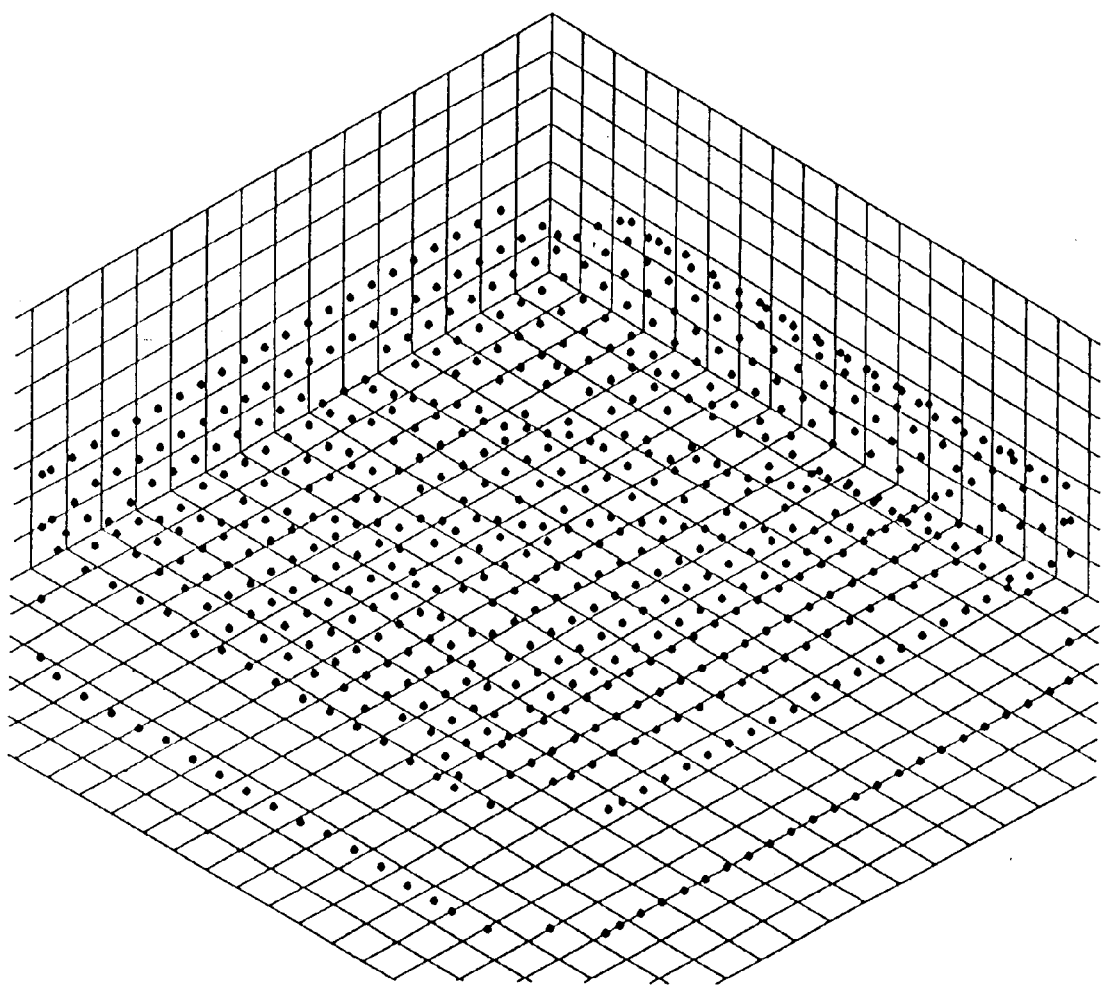
FIG. 30 is a three-dimensional graph showing one example of verification criteria data.

At this time, if measured data such as those shown in FIGS. 29 and 30 are stored in advance as verification criteria data, comparing the detection data of the detected object with the verification criteria data yields a better accuracy than performing verification against prestored three-dimensional data. The reason is that when converting the image containing distortion in the y-axis direction into three-dimensional data, the data is highly likely to depart from the true value. Here, FIG. 29 shows the measured data from one direction for a circular tablet EBUTOL shown in FIG. 47, while FIG. 30 shows the measured data from one direction for ANADROL shown in FIG. 47, a rectangular tablet with letter "A" engraved on the surface.

Figure 31:
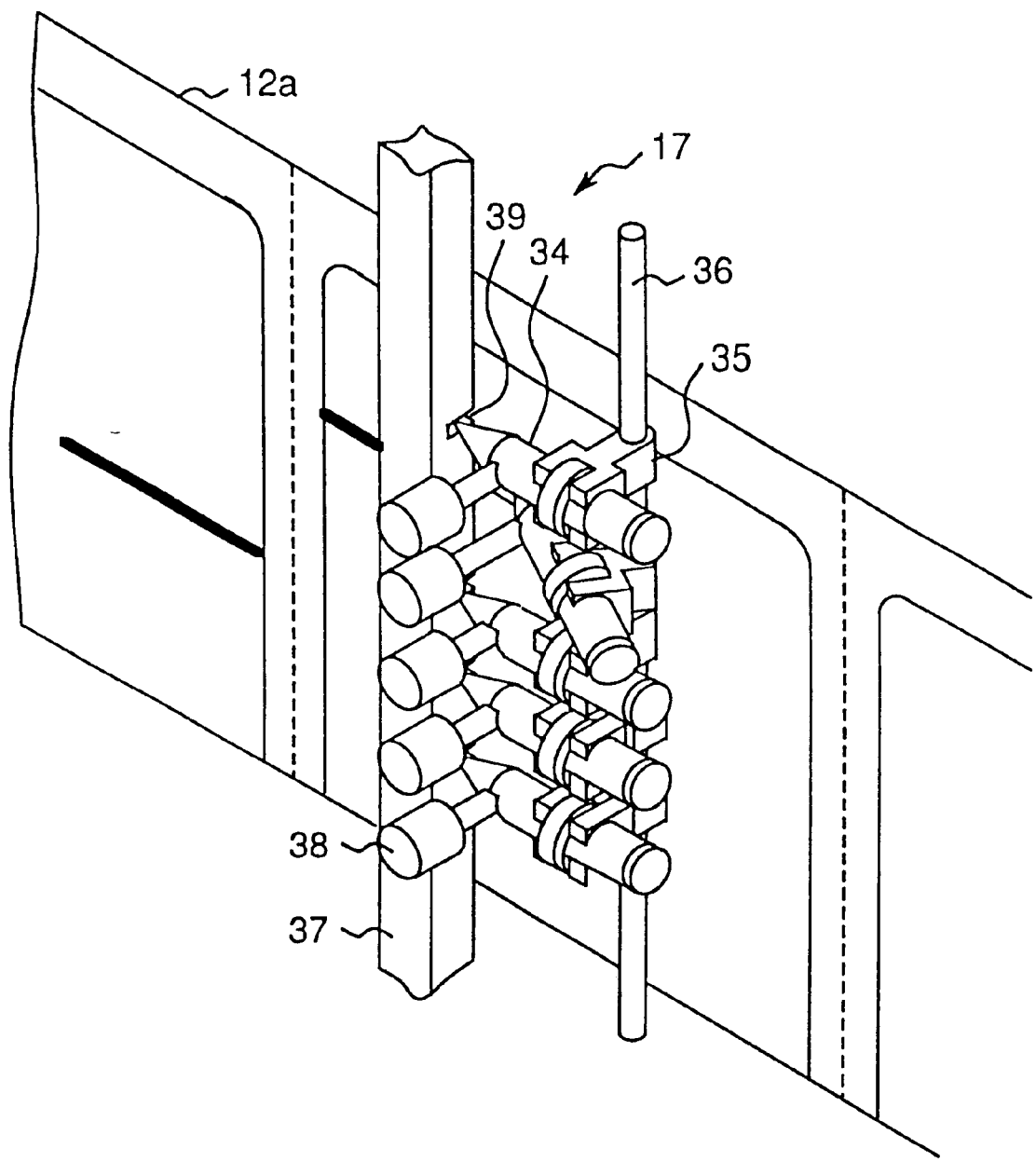
FIG. 31 is a perspective view of a mark appender.

The mark appender 17 is shown in FIG. 31. The mark appender 17 comprises a plurality of pens 34 of different colors for the different defect items, a supporting shaft 36 for supporting each pen 34 via a holder 35, and solenoids 38 mounted on a frame 37, each for pressing the tip of the associated pen 34 against the package 12a. Each pen 34 is urged by a spring (not shown) so as to be placed away from the package 12a when the solenoid 38 is not operated. The pen point is put in a slot 39 formed in the frame 37 to prevent drying. The mark appender 17 is disposed backward from a position where the medicine in the package pass through the line sensor 16 by a distance corresponding to the time necessary for the controller 18 to execute the number or shape identification process.

The controller 18 constitutes, as shown in FIG. 1, storage means, the tablet count determining means or the shape identifying means, and the comparing means according to the present invention, and may be a personal computer. The controller 18 may comprise three set. The first set of the controller 18 writes the data from the line sensor 16 in the storage means in time series and sends the data to the second set of the controller. The second set of the controller identifies the number and shape of the medicine in the package and stores the data. The third set of the controller compares the data processed by the second set of the controller with the prescription data corresponding to the package concerned, decides fail or pass of the package, and operates the mark appender 17 based on the decision. Thus, with the plural sets of the controller connected for separating the process, it is possible to promptly decide fail or pass of the package, allowing the inspection process to conduct without reducing the packing speed.

The measuring and data processing operations of the controller 18 will be described later. Before that, other embodiments of the tablet inspection apparatus 1 will be described. In the embodiments hereinafter described, parts that are essentially the same as those in the first embodiment will be designated by the same reference numerals and will not be discussed herein in detail.

Embodiment 2

Figure 32:
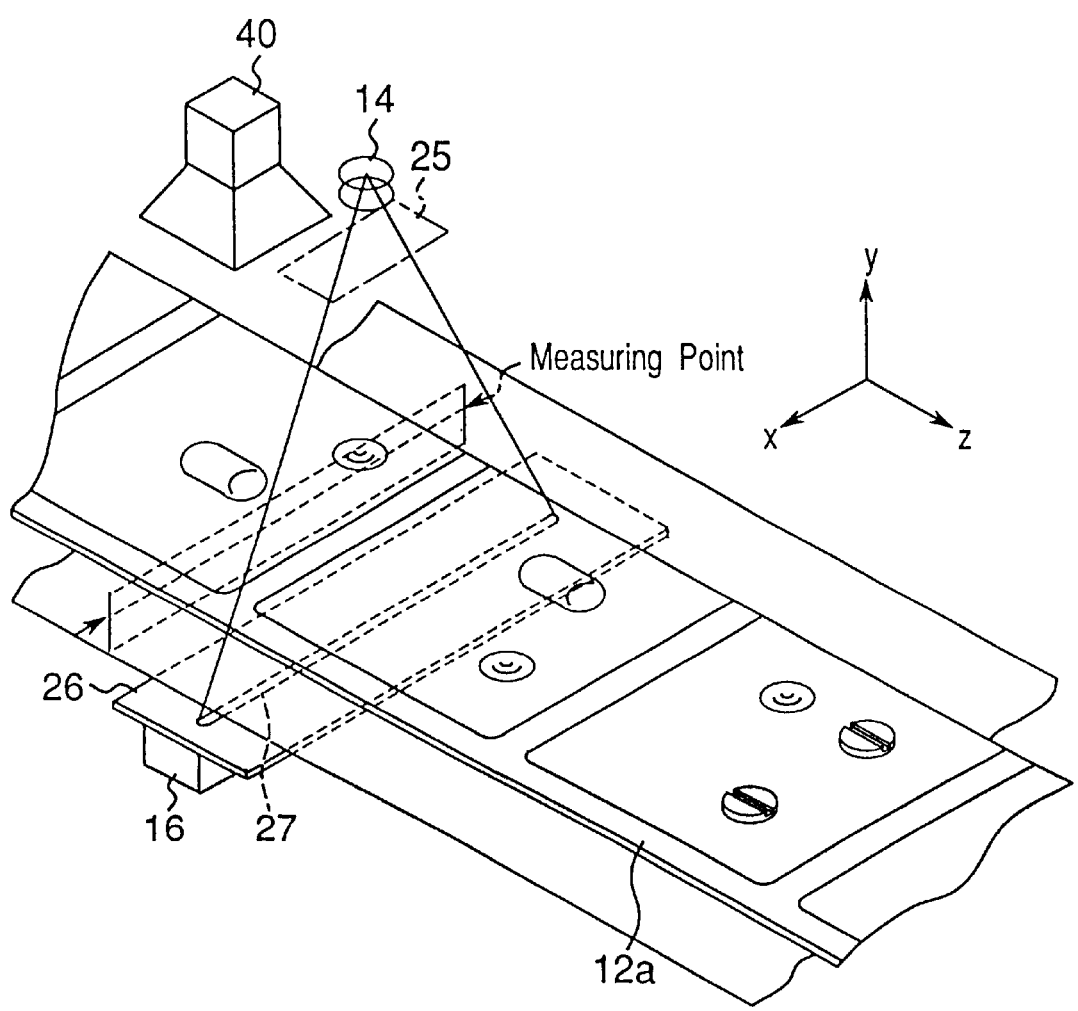
FIG. 32 is a perspective view of a tablet inspection apparatus according to a second embodiment of the present invention.

FIG. 32 shows the tablet inspection apparatus according to a second embodiment of the present invention. This tablet inspection apparatus includes the X-ray tube 14 and line sensor 16 in the same manner as the tablet inspection apparatus of the first embodiment shown in FIG. 10. In addition, a CCD camera 40 which captures an image of medicine contained in the package 12a from the y-axis direction is disposed upwardly of the package 12a.

Figure 33:
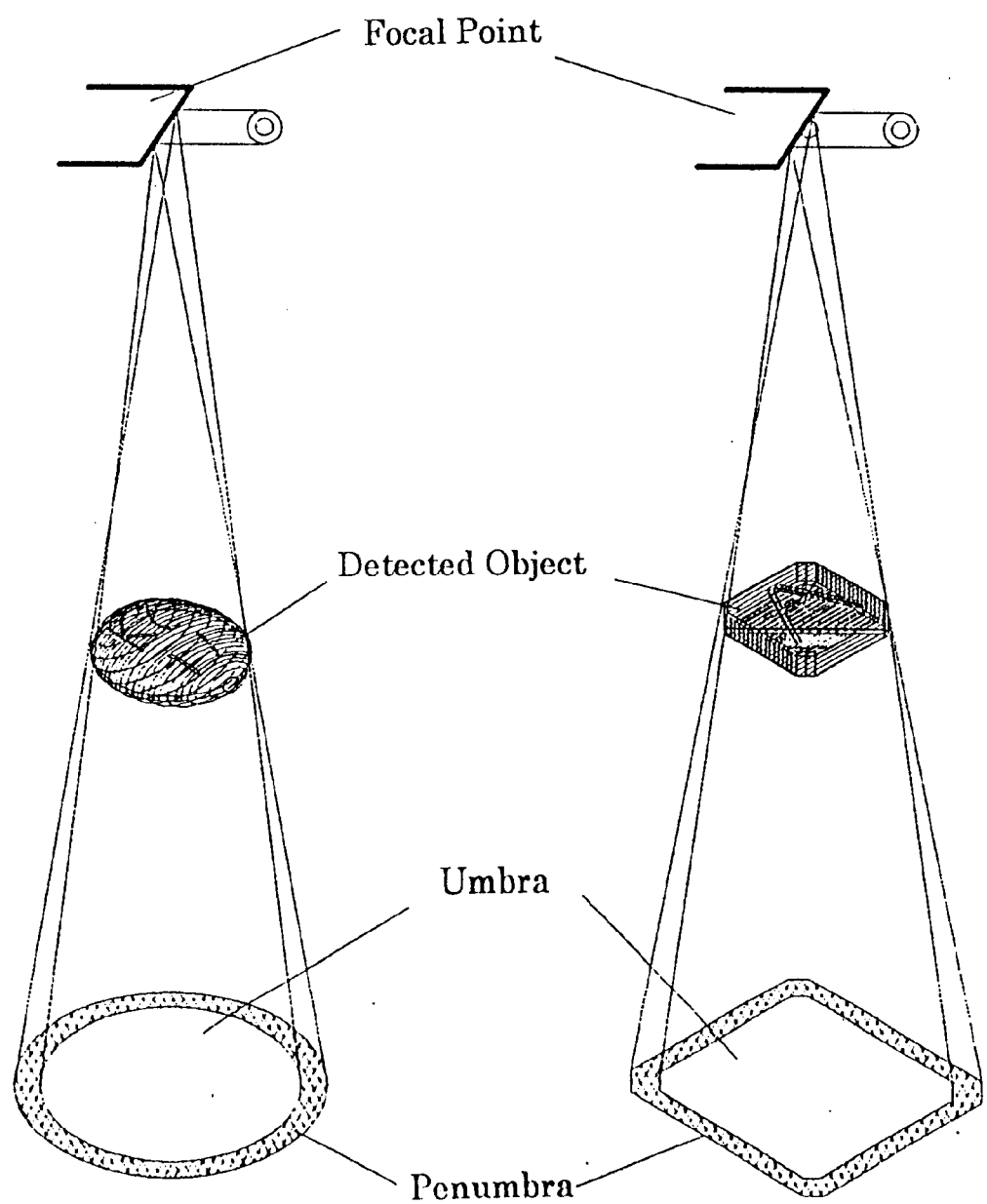
FIG. 33 is a perspective view for explaining how shadows are formed by X-rays.

Using the CCD camera 40, color data and outer dimensional data of tablets can be acquired. By acquiring color data by the CCD camera 40, not only tablet overlapping can be recognized to a certain extent, but the tablet type can also be identified with higher accuracy. In the case of X-ray data, the detection accuracy of the tablet dimensions degrades because of the presence of a penumbra such as shown in FIG. 33. This can be corrected by using the outer dimensional data acquired by the CCD camera 40. In such case, if a plural sets of controllers are independently provided, it is possible to conduct the whole process without affecting the packing speed.

Embodiment 3

Figure 34:
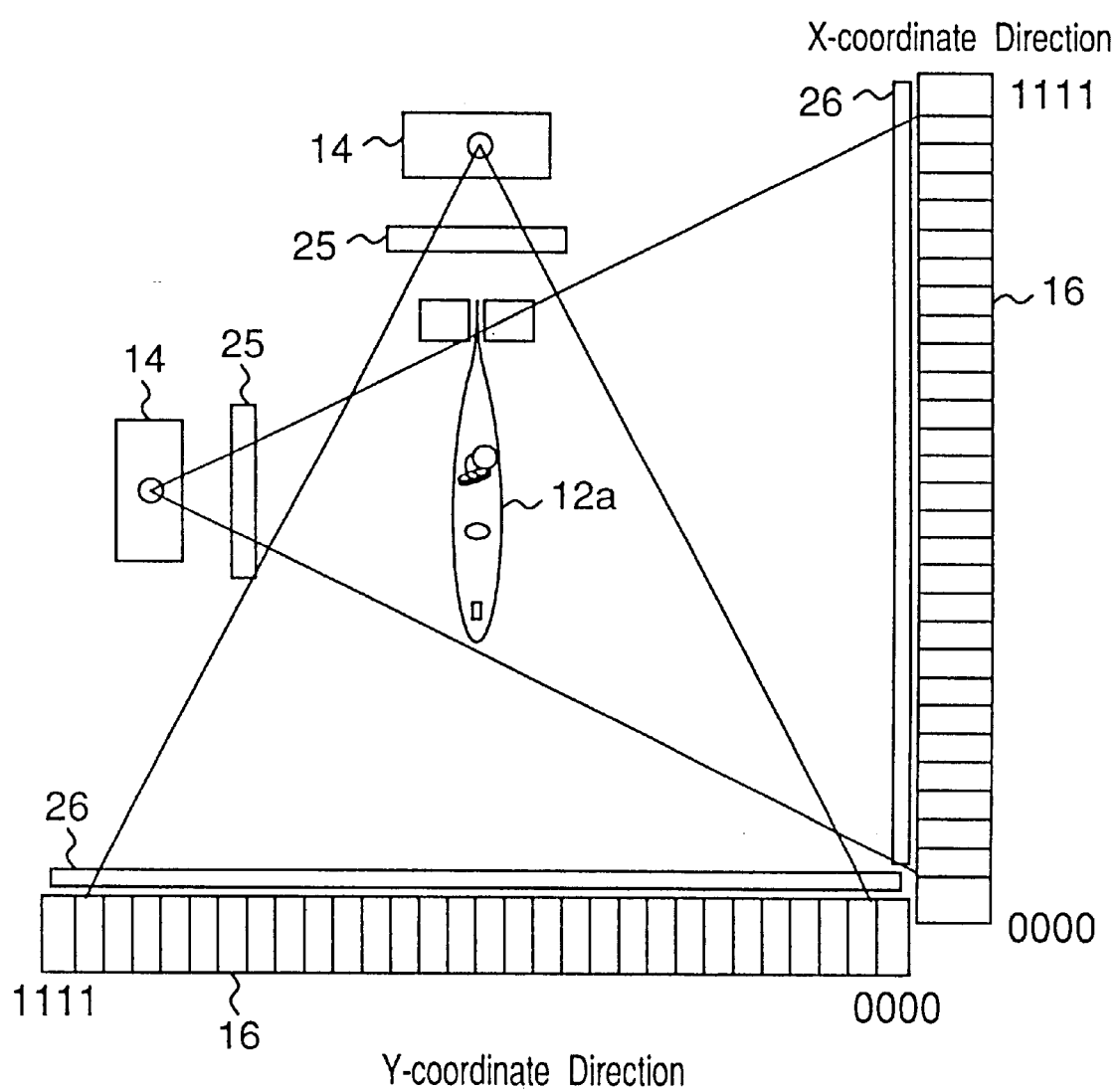
FIG. 34 is a side view of a tablet inspection apparatus according to a third embodiment of the present invention.
Figure 35:
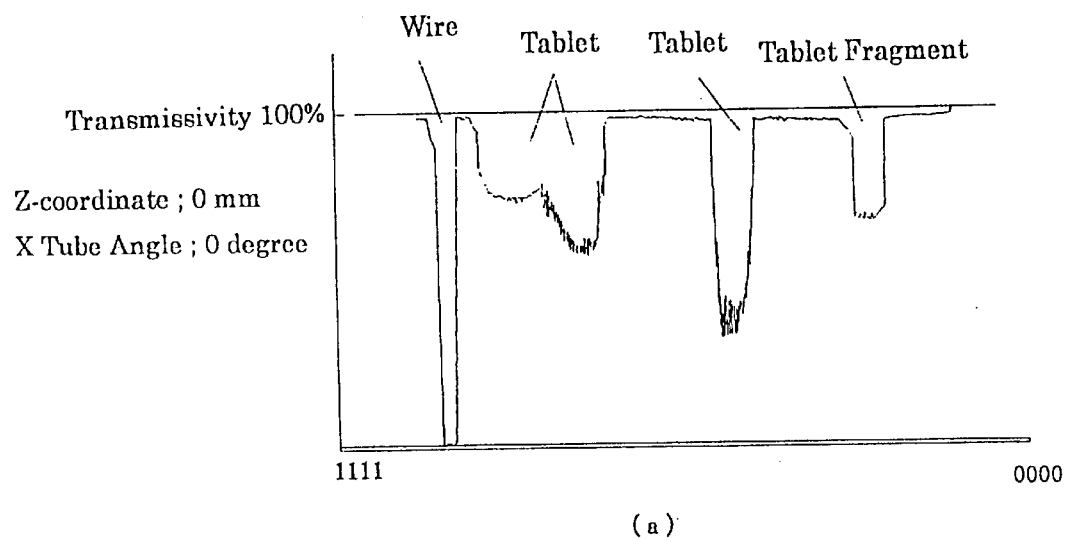
FIGS. 35(a and b) are graphs showing the transmission amount output data of line sensors X and Y directions.
Figure 35:
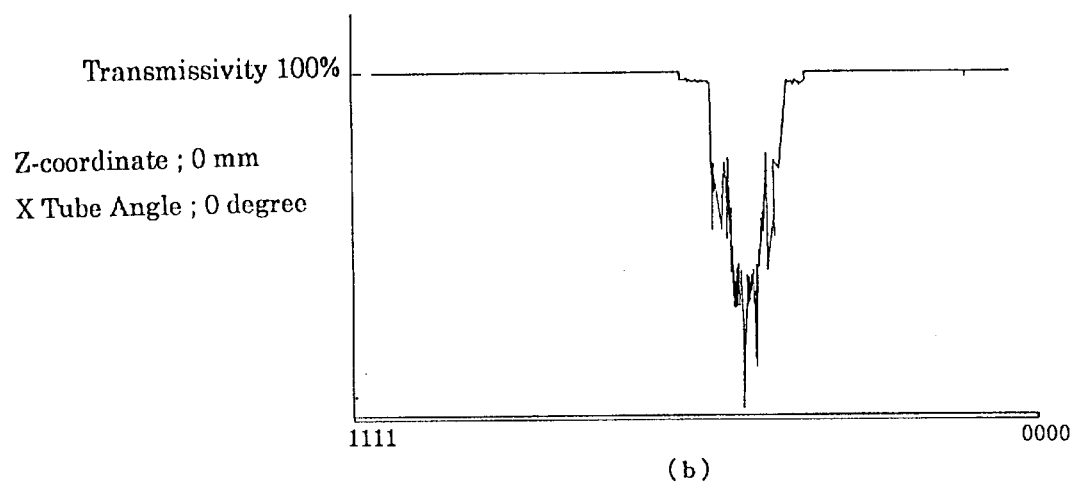
Figure 36:
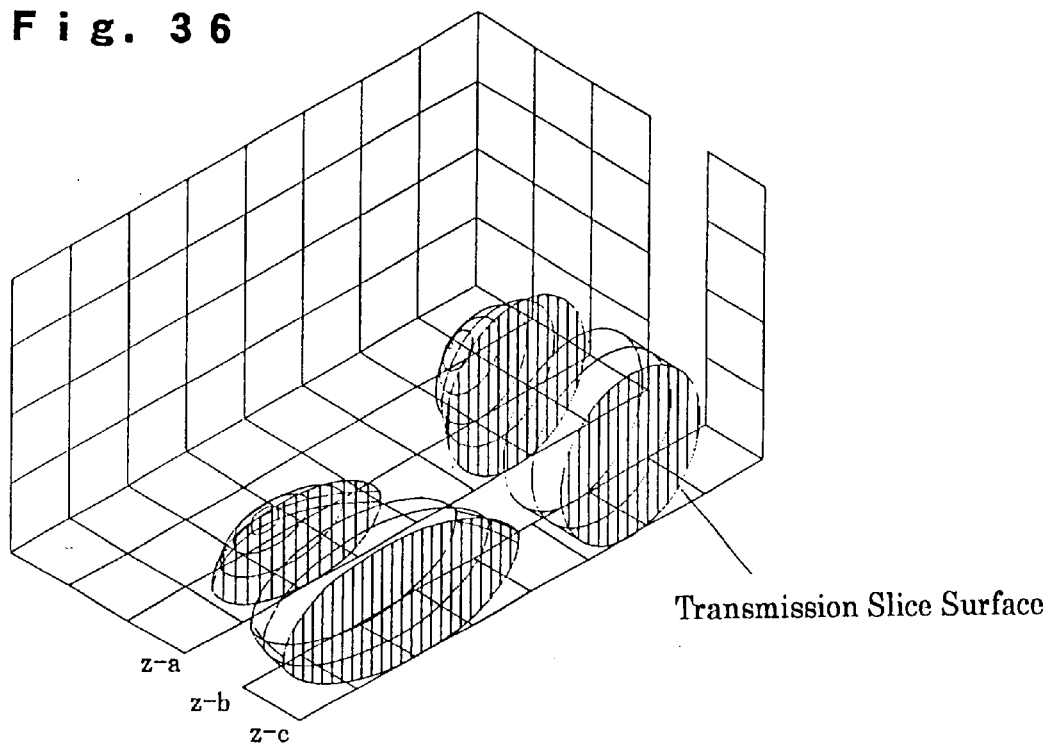
FIG. 36 is a graph showing three-dimensional image data.
Figure 36:
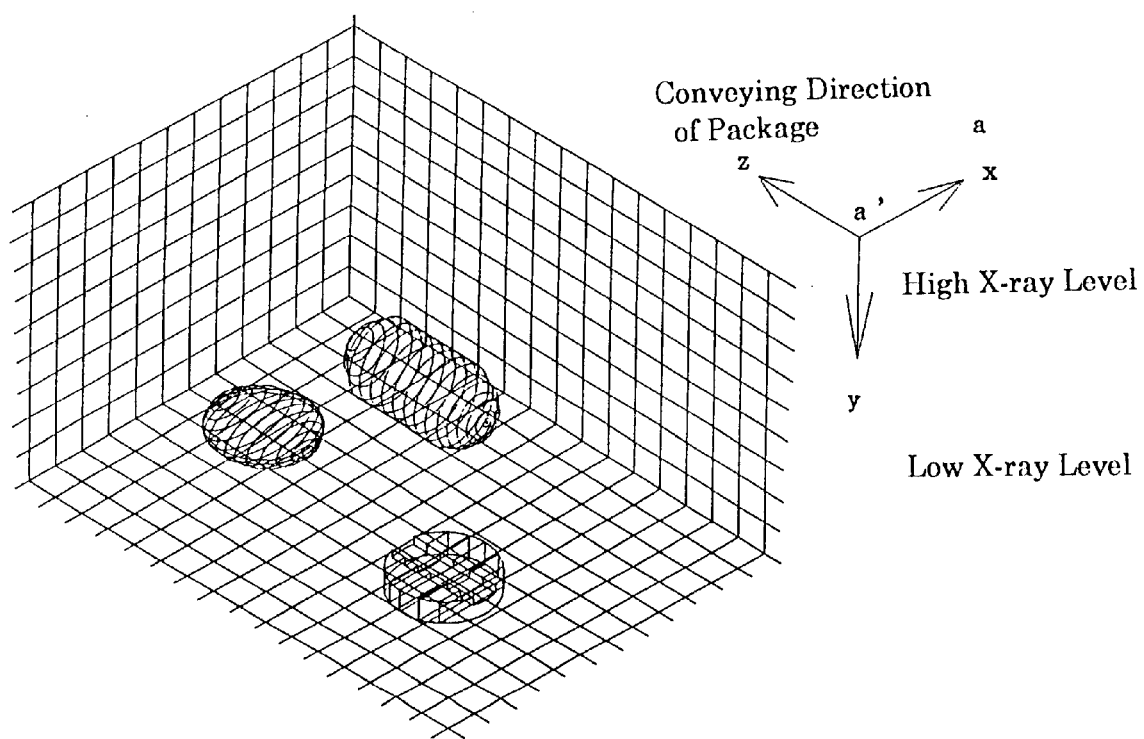

FIG. 34 shows the tablet inspection apparatus according to a third embodiment of the present invention. This tablet inspection apparatus includes, in addition to the X-ray tube 14 and the line sensor 16 arranged in the y-axis direction, an X-ray tube 14 and a line sensor 16 arranged in the x-axis direction so that X-rays are projected to the package 12a from two directions 90° apart from each other. According to this apparatus, overlapping tablets in a package can be recognized to a certain extent by using the X-ray transmission amount data in the x-axis and y-axis directions, as shown in FIGS. 35 (*a* and *b*). Furthermore using the two-directional data, it becomes possible to display the cross sectional images shown in FIG. 36 or the three-dimensional image shown in FIG. 24.

Figure 37:
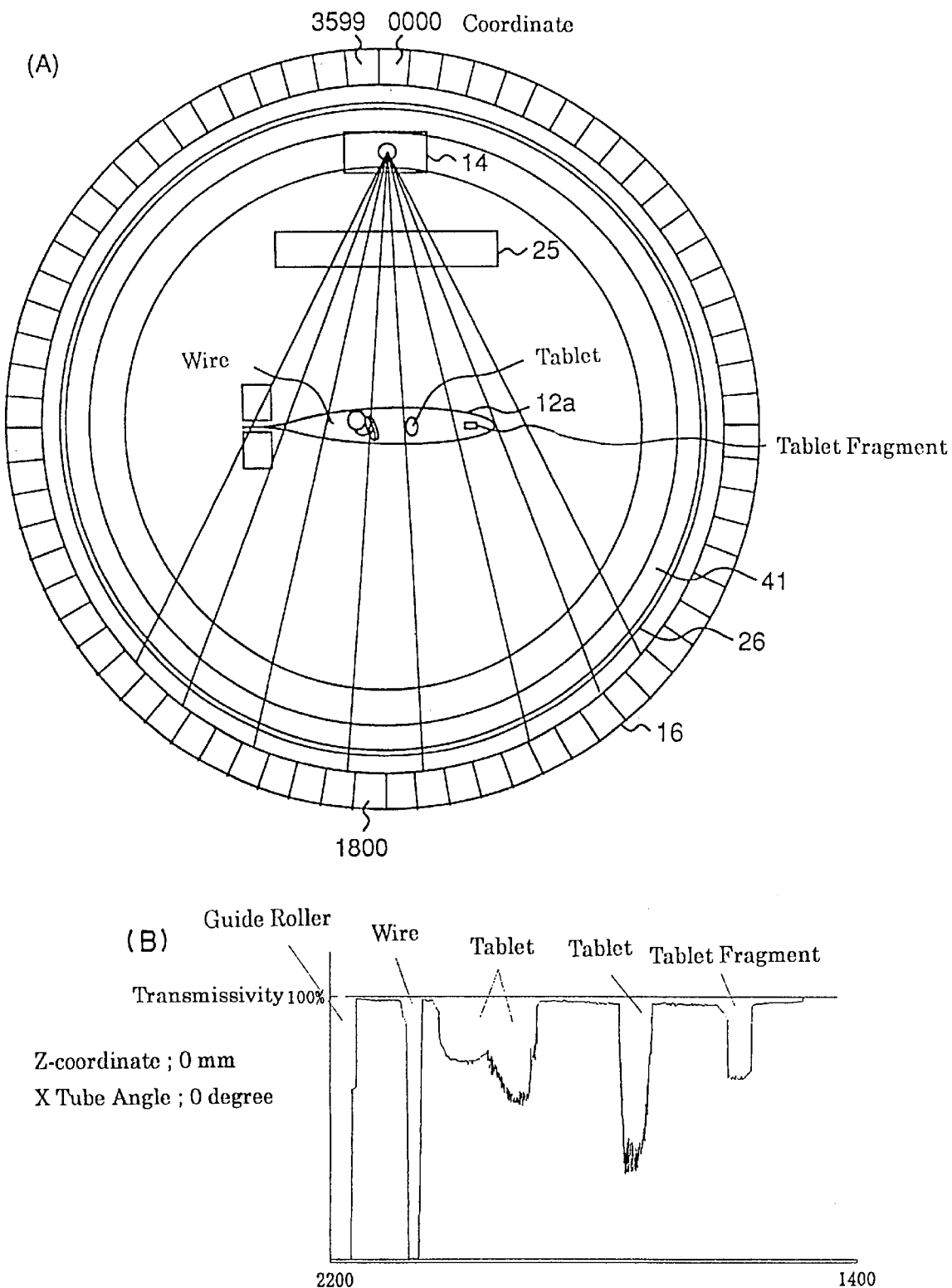
FIG. 37A is a side view of a tablet inspection apparatus according to a fourth embodiment of the present invention.
FIG. 37B shows X-ray transmission amount output by moving the X-ray tube.
Figure 38:
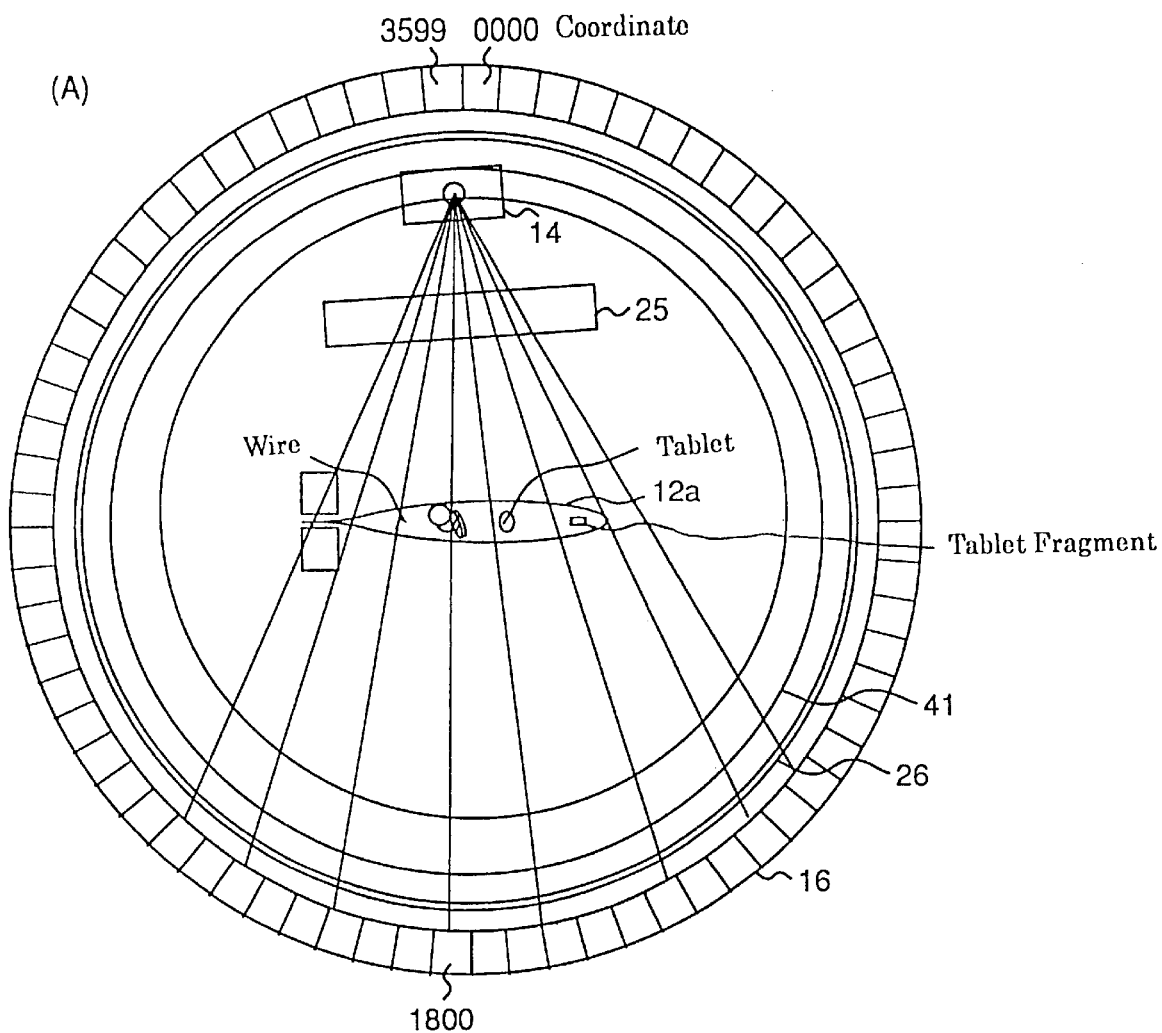
FIG. 38A is a side view of the tablet inspection apparatus when rotated 5°.
FIG. 38B shows X-ray transmission amount output by moving the X-ray tube 0.075 m.
Figure 38:
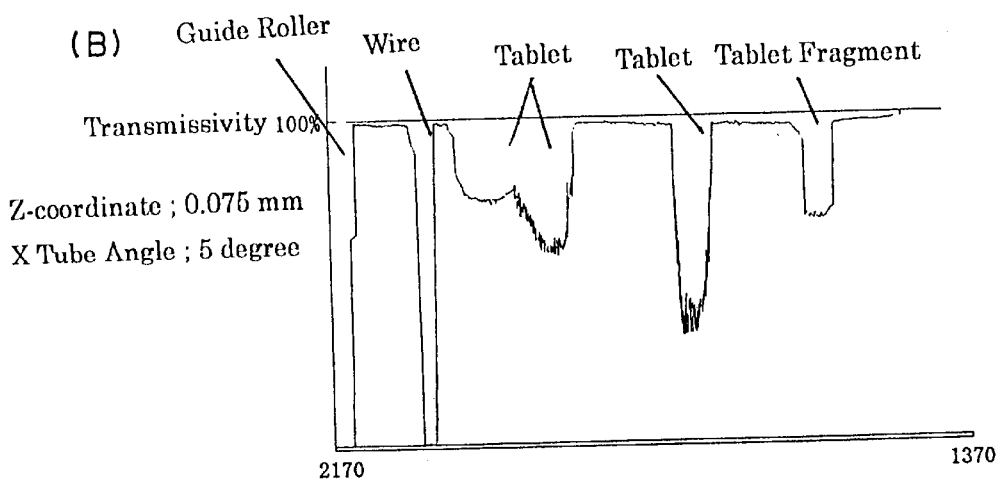
Figure 39:
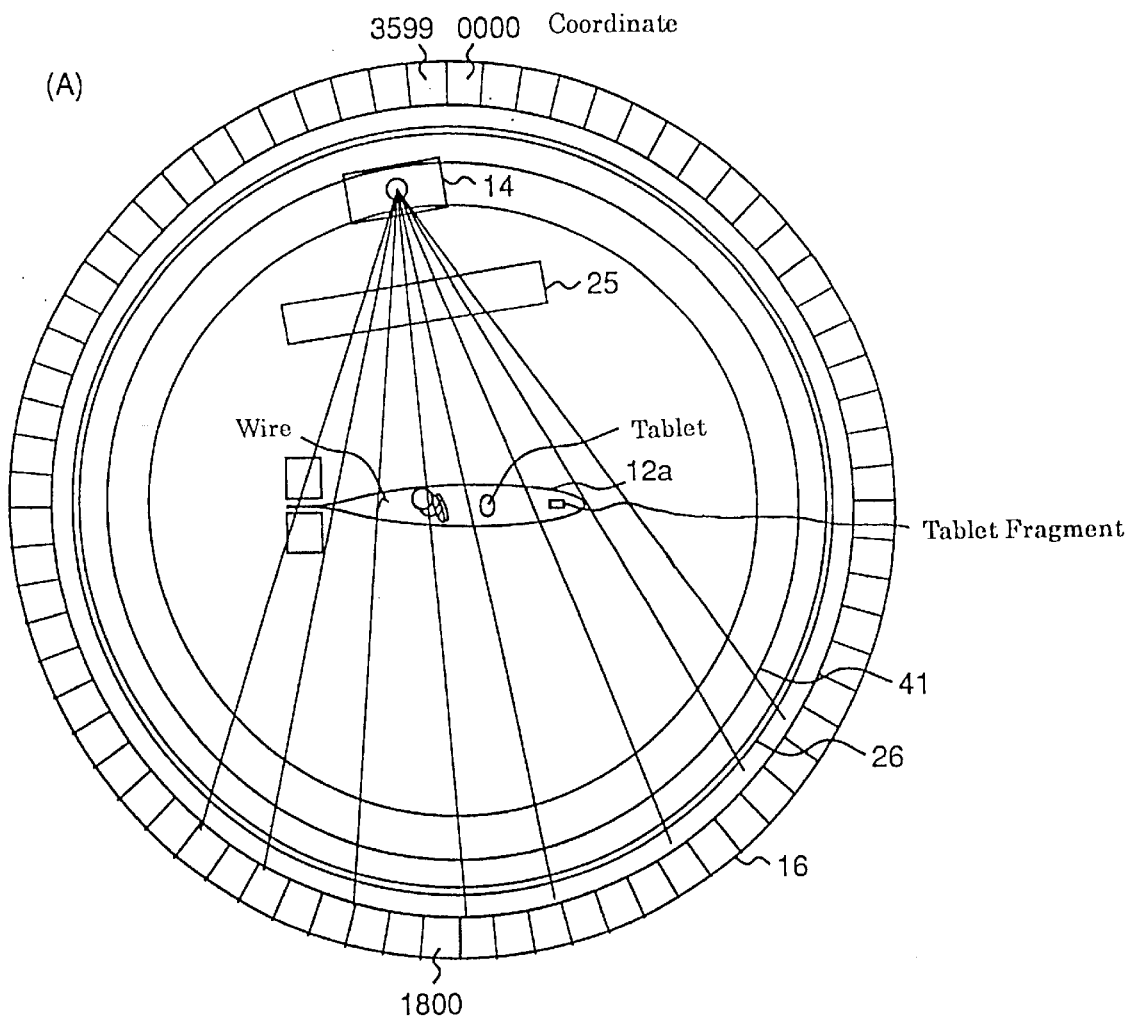
FIG. 39A is a side view of the tablet inspection apparatus when rotated 10 °.
FIG. 39B shows X-ray transmission amount output by moving the X-ray tube 0.15 m.
Figure 39:
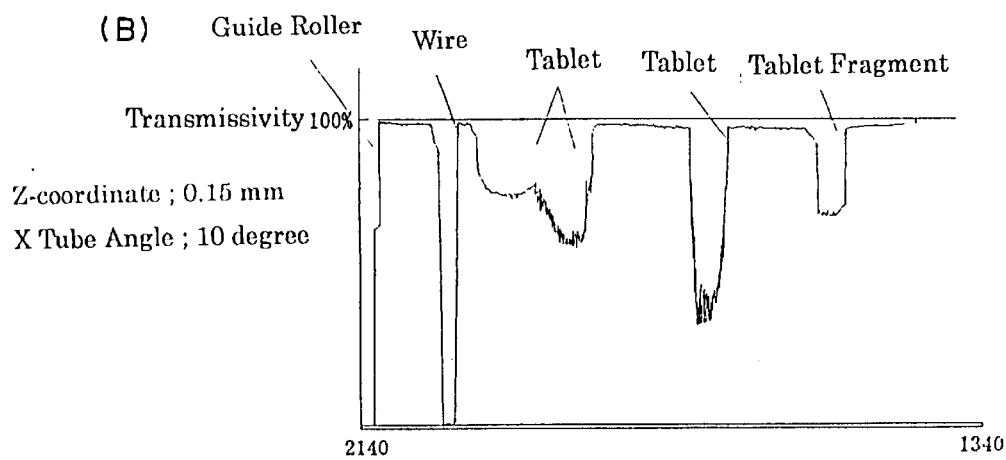
Figure 40:
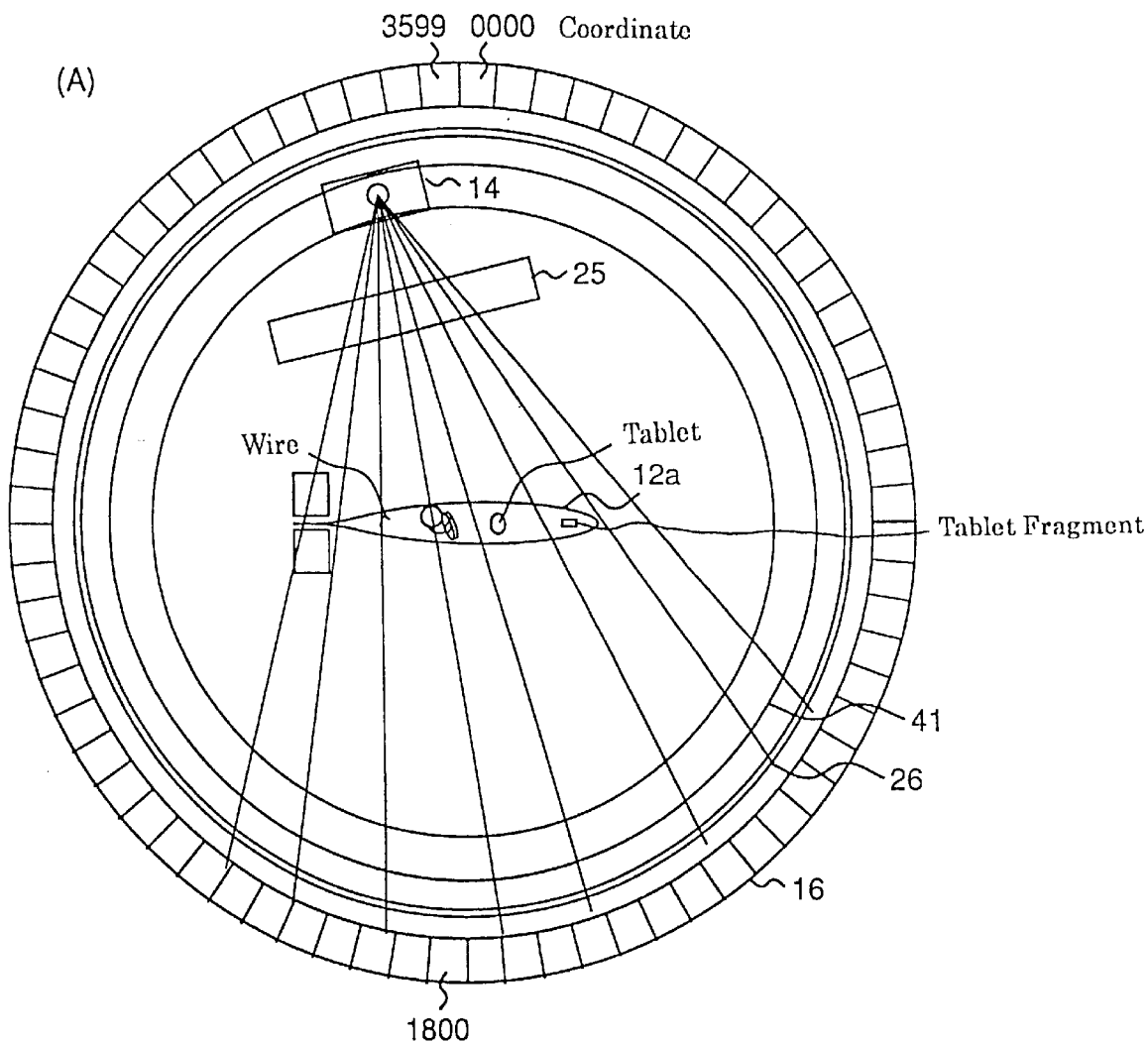
FIG. 40A is a side view of the tablet inspection apparatus when rotated 15°.
FIG. 40B shows X-ray transmission amount output by moving the X-ray tube
Figure 40:
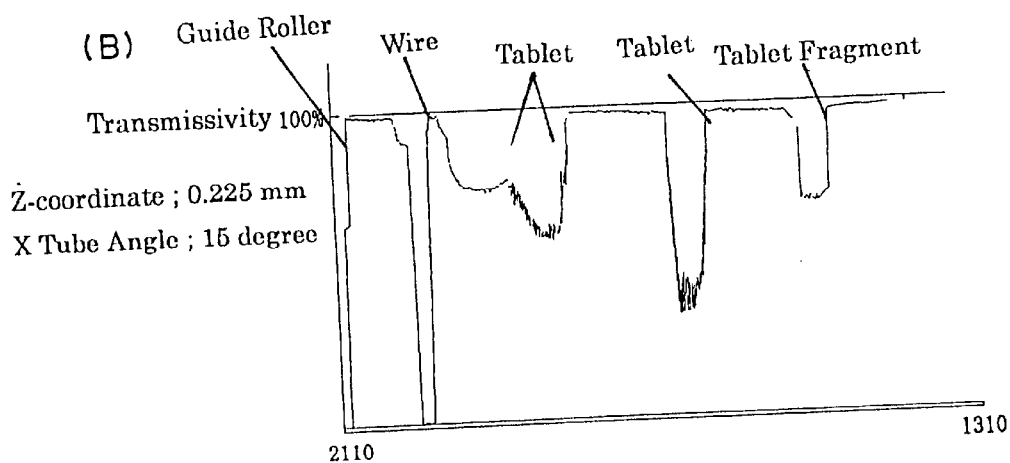

FIGS. 37 (*a* and *b*) show the tablet inspection apparatus according to a fourth embodiment of the present invention. This inspection apparatus comprises an annular raceway 41 surrounding the object to be inspected, an X-ray tube 14 mounted movably on the annular raceway 41, and an annular line sensor 16 mounted surrounding the outer circumference of the annular raceway 41. Between the annular raceway 41 and annular line sensor 16 is disposed a mask 26 having slits 27 formed therin. Further, an aluminum filter 25 movable together with the X-ray tube 14 around the object to be inspected is disposed between the X-ray tube 14 and the package 12a to be inspected.

Figure 41:
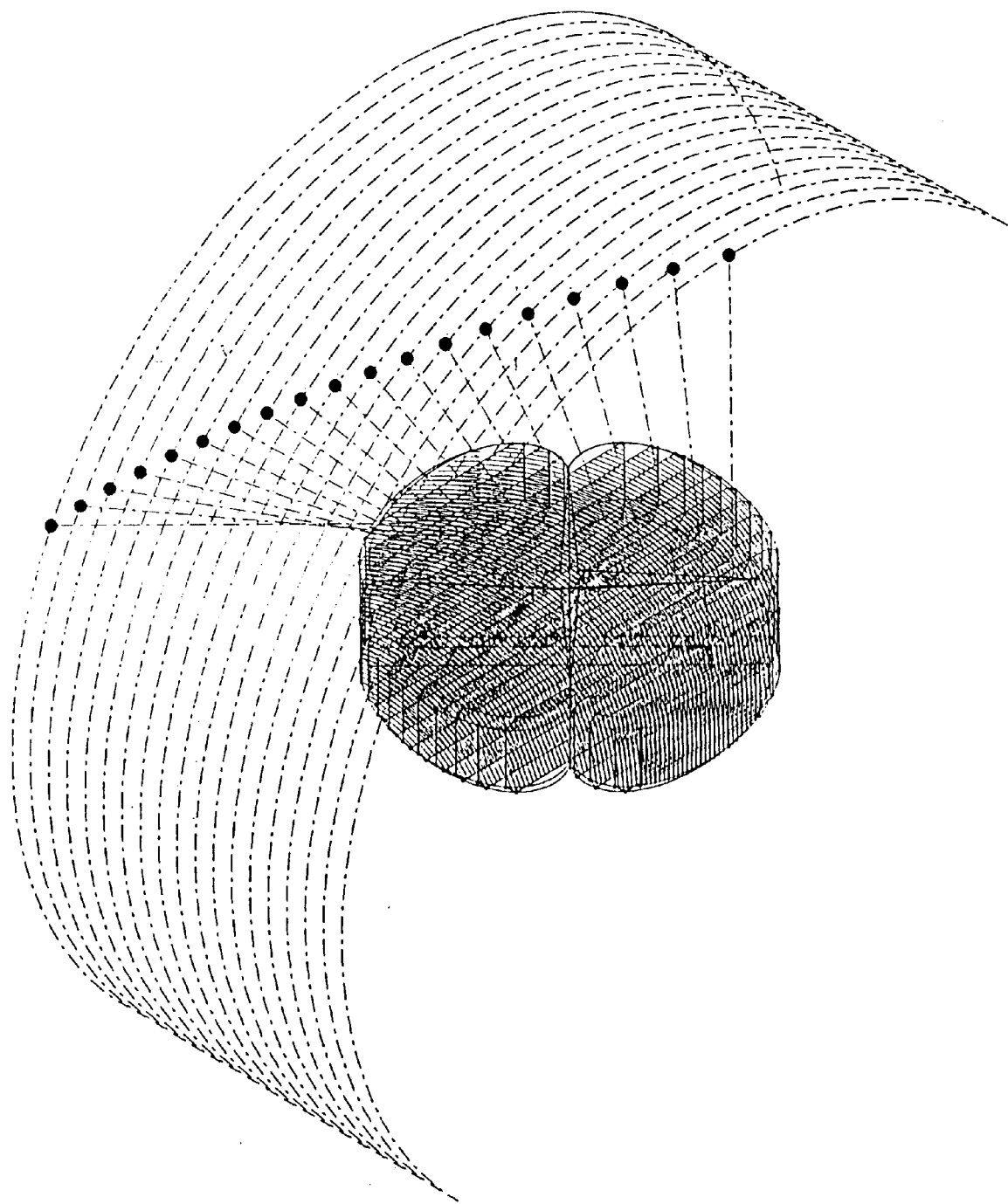
FIG. 41 is a diagram showing three-dimensional image data.

In the tablet inspection apparatus, as shown in FIGS. 37 (*a* and *b*) to 40 (*a* and *b*), X-ray transmission factor data is acquired by moving the X-ray tube 14 by predetermined degrees while feeding the package 12a in the z-axis direction. The amount of attenuation due to the presence of the package 12a is subtracted from the acquired data After processing for noise elimination, edge enhancement, and detection of attenuation amount center values is performed, the centers of the attenuation amounts are aligned and concatenated in spiraling fashion in correspondence with the detection angles. As a result, the image data shown in FIG. 41 is obtained.

Figure 42:
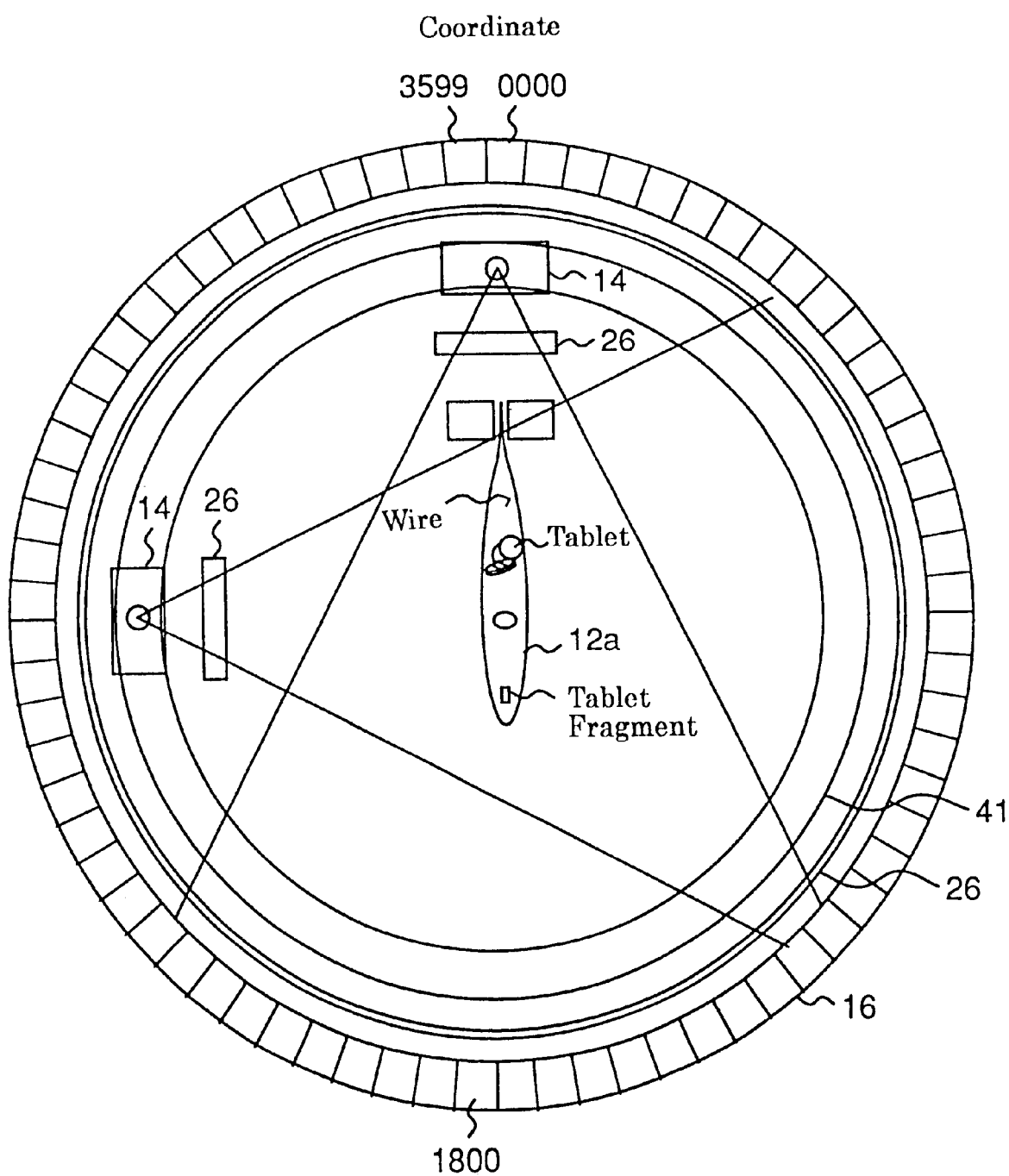
FIG. 42 is a side view of a tablet inspection apparatus according to a fifth embodiment of the present invention.

FIG. 42 shows the tablet inspection apparatus according to a fifth embodiment of the present invention. This inspection apparatus combines the construction in FIG. 34 with that in FIG. 37. More specifically, two X-ray tubes 14 are mounted spaced 90° apart from each other, and the annular raceway 41 for mounting the two X-ray tubes 14 thereon and the annular line sensor 16 are disposed surrounding the package 12a which is the object to be inspected. In this tablet inspection apparatus, the X-ray tubes 14 move around the package 12a, while maintaining the 90° apart positional relationship. Therefore, not only can the thickness data and X-ray transmission amount data of the object to be inspected be detected simultaneously, but the external shape of the object can be measured from multiple directions. Accordingly, if multiple tablets are packed in a package 12a with one tablet overlapping another in layers, the tablet type and tablet count can be determined correctly.

In the tablet inspection apparatus, the X-ray tubes 14 are rotated 360° while radiating X-rays at radiation exposure points disposed at intervals of 10°, and the package 12a is movable in the z-axis direction by a pitch of 0.76 mm for every 10° radiation exposure point. This configuration serves to shorten the inspection time.

Embodiment 6

Figure 43:
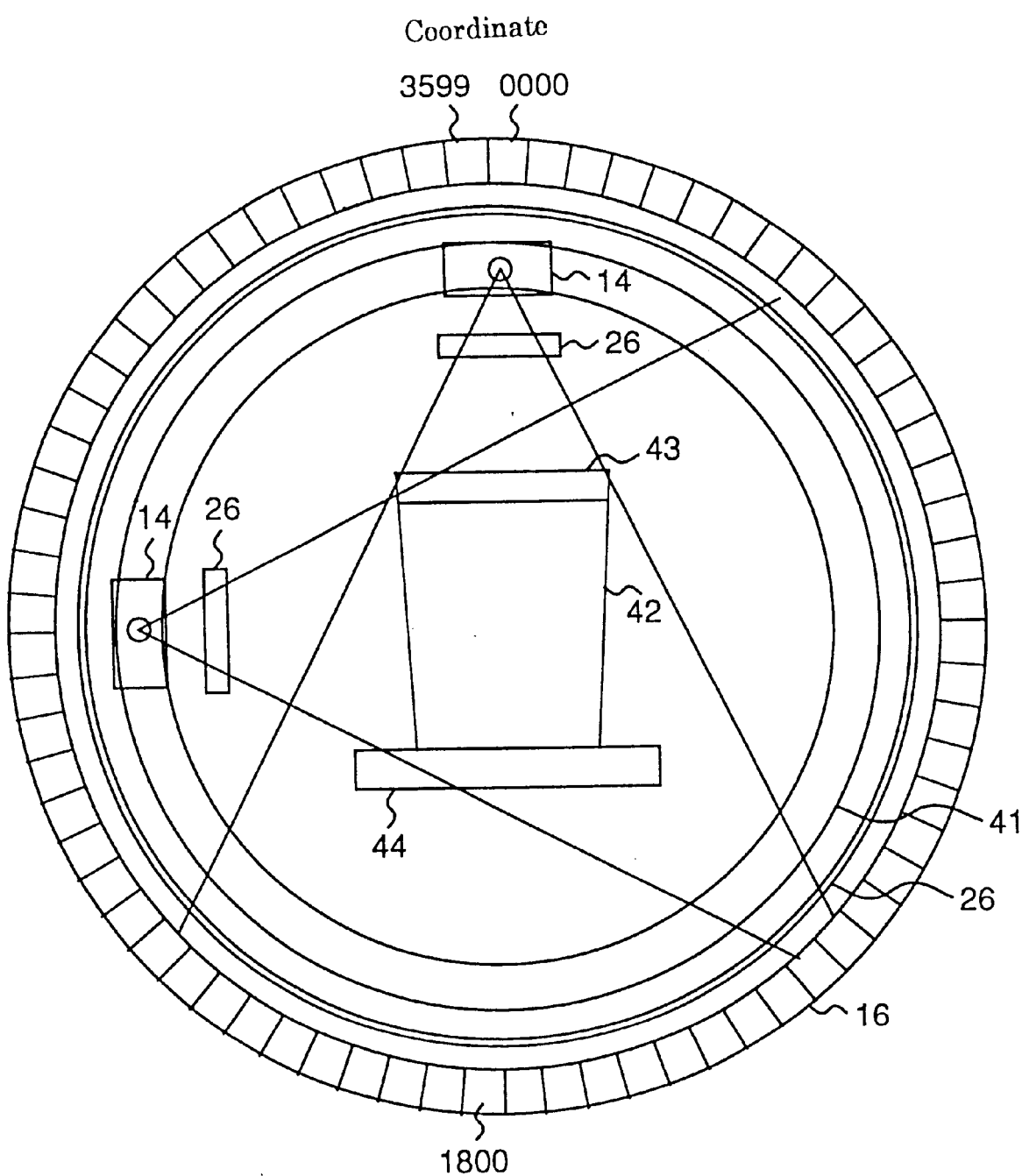
FIG. 43 is a side view of a tablet inspection apparatus according to a sixth embodiment of the present invention.
Figure 44:
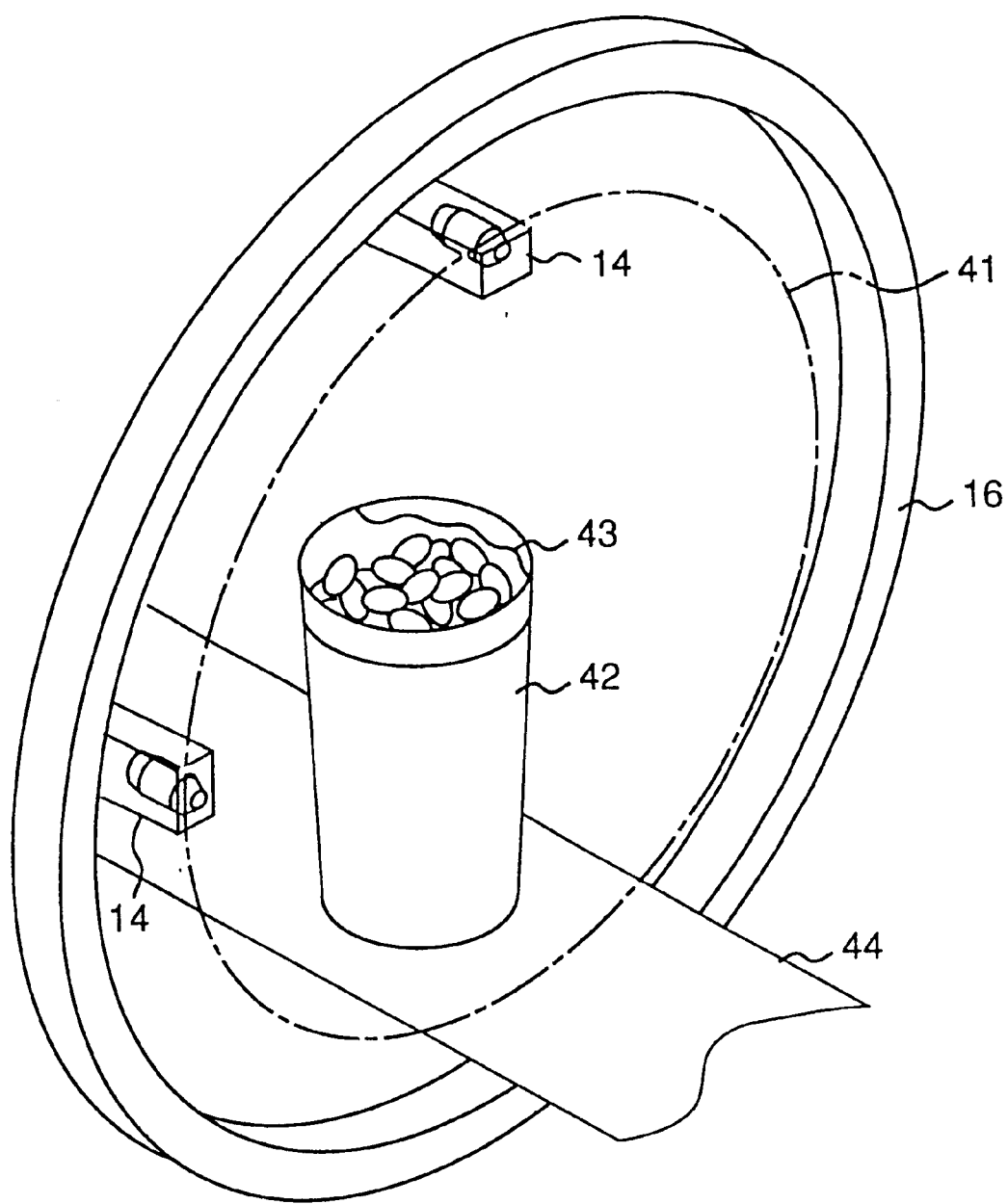
FIG. 44 is a perspective view of the tablet inspection apparatus of FIG. 43.

FIG. 43 shows the tablet inspection apparatus according to a sixth embodiment of the present invention. This inspection apparatus is the same as that of the fifth embodiment, except that the objects to be inspected are medicine filled in a vial bottle 42. The vial bottle 42, usually used in the U.S. and Europe, has a plastic cap 43 for preventing children from opening it, and is filled with one type of medicine for prescribed days. The vial bottle 42 is conveyed on a conveyer belt 44, as shown in FIG. 44. The vial bottle 42 contains many medicine one overlapping another in layers, and since the X-ray attenuation amount is larger than in the case of the package 12a used in the foregoing embodiments. Therefore, the number of measurements at each measuring point in the z-axis direction must be increased so that the tablet count and tablet type can be determined with higher accuracy.

<Measuring operation>

Figure 45:
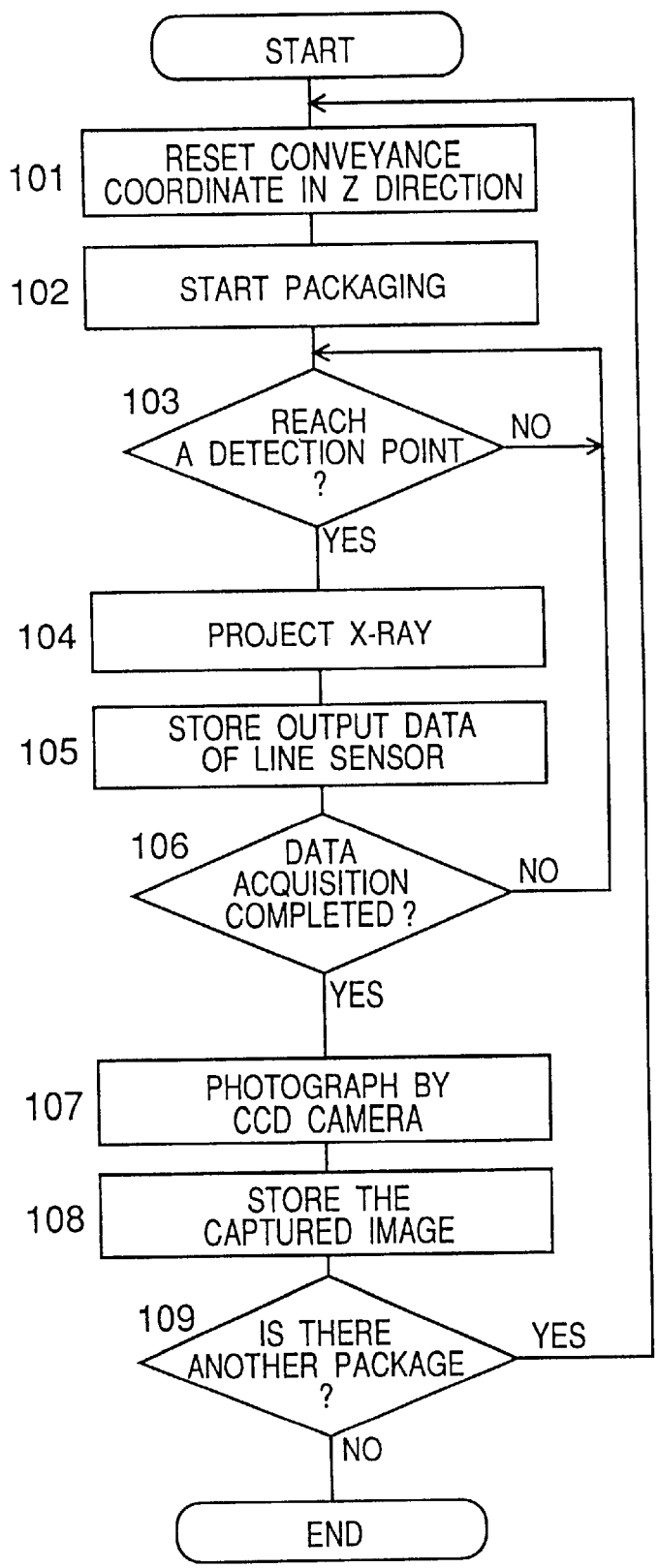
FIG. 45 is a flowchart illustrating a measuring operation.
Figure 46:
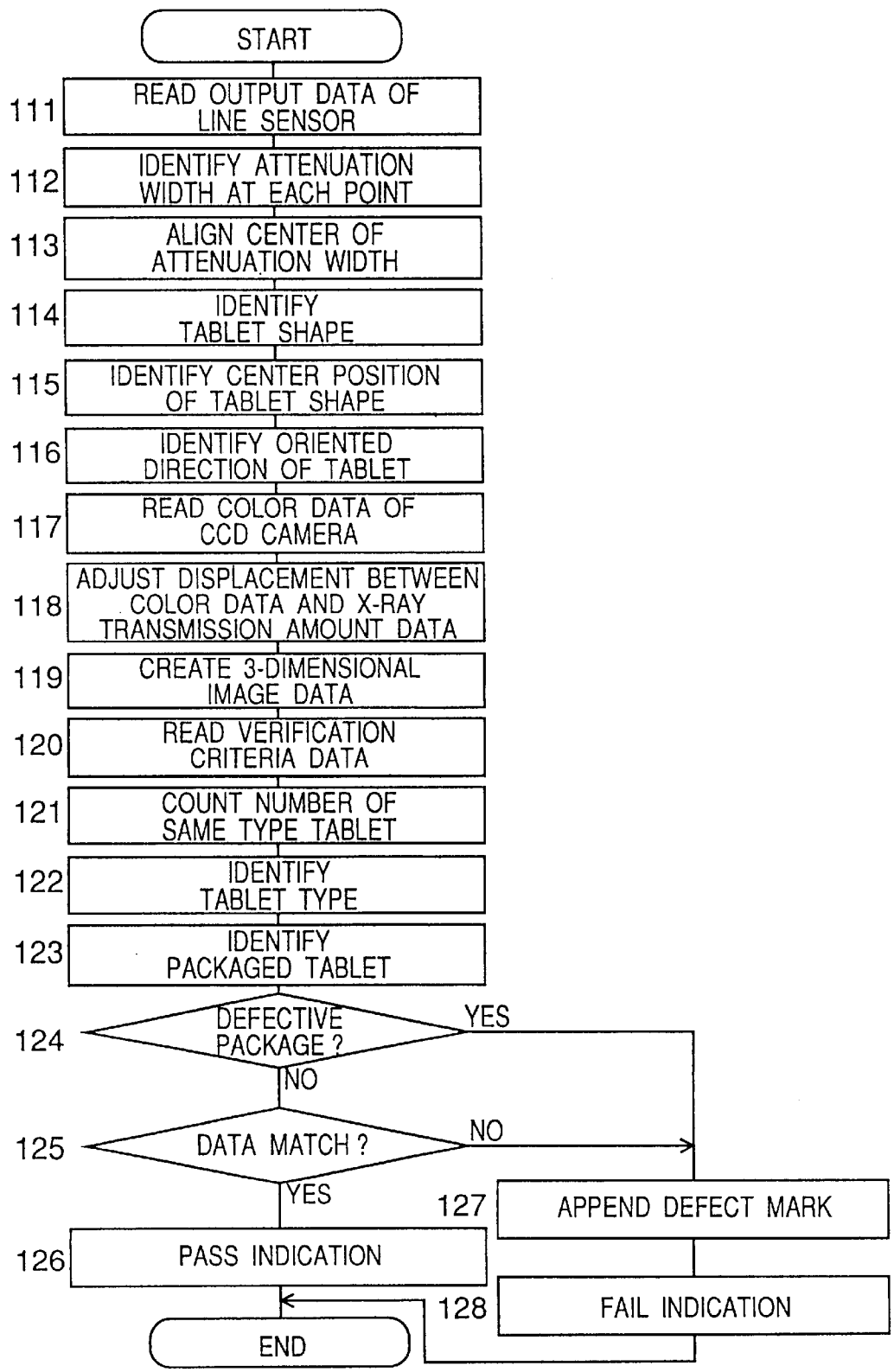
FIG. 46 is a flowchart illustrating a data processing operation.

Next, the measuring and data processing operations of the tablet inspection apparatus of the second embodiment shown in FIG. 32 will be described with reference to the flow charts of FIGS. 45 and 46. The operations are essentially the same for the other embodiments.

First, the measuring operation will be described. As shown in FIG. 45, the conveyance coordinate of the package 12a in the z-axis direction is reset in step 101. The packaging operation is started in step 102. In step 103, a decision is made as to whether the package 12a has reached a detection point. If the answer to the decision is YES, X-rays are projected in step 104, and output data of the line sensor 16 is stored in step 105. Next, in step 106, a decision is made as to whether data acquisition from all detection points covering the range of one dose has been completed or not. If not completed yet, the process loops back to step 103 to acquire data from the next detection point. If the data acquisition from all detection points covering the range of one dose has been completed, the range of one dose is photographed by the CCD camera 40 in step 107, and the captured color image is stored in step 108. Next, in step 109, a decision is made as to whether there is another package to be measured. If YES, the process loops back to step 101, and if NO, the process is terminated.

<Data processing operation>

Next, the operation for processing the data acquired by the above measuring operation will be described with reference to the flow chart of FIG. 46.

First, in step 111, the stored output data of the line sensor 16 is read out. In step 112, the attenuation width at each point in the output data is identified. In step 113, the center of the attenuation width is aligned in correspondence with the sensor coordinate and z-axis coordinate. In step 114, based on the prestored X-ray attenuation factor, the tablet shape is identified from the X-ray transmission amount which is the output data of the line sensor 16. Next, in step 115, the center position of the tablet shape is identified. This center position serves as a mark when matching against color data in a later step. In step 116, the oriented direction of the tablet is identified. Tablets are oriented in random directions when packed in the package 12a. However, by identifying the oriented direction of each tablet, the tablet can be quickly matched for identification.

In step 117, the color data acquired by the CCD camera 40 is read from a storage device. In step 118, the color data from the CCD camera 40 and the X-ray transmission amount data from the line sensor 16 are adjusted by matching the data against the center position of the tablet to correct any displacements. In step 119, three-dimensional image data is created from the color data created in step 118.

Next, in step 120, verification criteria data is read out. At this time, rather than reading out the verification criteria data for all tablets for matching, it is preferable to read out the verification criteria data only for the attention tablet supposed to have been packed in the package 12a. This is because, in the latter case, the verification processing can be performed much faster. In step 121, the number of tablet center positions in the three-dimensional image data is counted to determine the number of tablets of the same type. In step 122, the tablet type is identified by matching against the verification criteria data read out in step 120. Then, in step 123, the packaged tablets are verified.

In step 124, in order to check the package 12a for the presence of dust, foreign material, tablet fragments, etc., it is determined whether there is any detection data that does not match the verification criteria data. If there is such data, a defect mark is appended in step 127 and a fail indication is produced in step 128. If there is no such data, the process proceeds to step 125. In step 125, it is determined whether the identified tablet type and tablet count match the prescription data for the medicines supposed to have been packed. If they do not perfectly match, a defect mark is appended in step 127 and a fail indication is produced in step 128. If they match perfectly, a pass indication is produced in step 126. The above verification results are stored in correspondence with patient identification number.

<Data processing for defectives>

The package is rendered defective if any of the following defect items is detected.

1. Forward or backward displacement in the feed position of the package belt
2. Mixing of foreign material
3. Cracked medicine
4. Wrong count of medicines
5. Discrepancy between prescribed medicine type and packaged medicine type.

When the defective package is detected, the dispensing pharmacist must be notified accordingly and, depending on the situation, repackaging will become necessary. A monitor, indication lamp, buzzer, or the like may be used as the means of defect notification. However, in order to clarify the kind of defect and the location of the defect on the package sheet, it is preferable to append a defect identifying mark directly to the designated part of the package by using the mark appender 17.

Of the packaging defects listed above, data processing will be described first for the case of the defect that the feed position of the package belt is displaced forward or backward. For example, when a prescription is made to a patient for four days' medicine prescribing three tablets "A" per day, one after each meal, and two tablets "B" per day, one each after breakfast and supper, then "MORNING", "AFTERNOON", and "EVENING" are printed in sequence on the package. Two tablets should be packed in the package printed "MORNING", one tablet in the package printed "AFTERNOON", and two tablets in the package printed "EVENING". Here, if the feed position of the package is displaced forward or backward, one tablet will be packed in the package printed "MORNING" and two tablets in the package printed "AFTERNOON", each package thus containing an incorrect number of tablets.

In the prior art, if such a defect occurs, it has been necessary to separate the "MORNING" and "AFTERNOON" packages from the package and to repackage them by entering a prescription for the two packages through the terminal of the packaging machine. On the other hand, in the embodiment of the present invention, when the above defect is detected, prescription data for the "MORNING" and "AFTERNOON" packages is set as interrupt standby information in the packaging machine, thus saving the trouble of entering the information. The tablets for the defective two packages are automatically repackaged in accordance with the interrupt standby information after completing the packaging for the patient.

Figure 62:
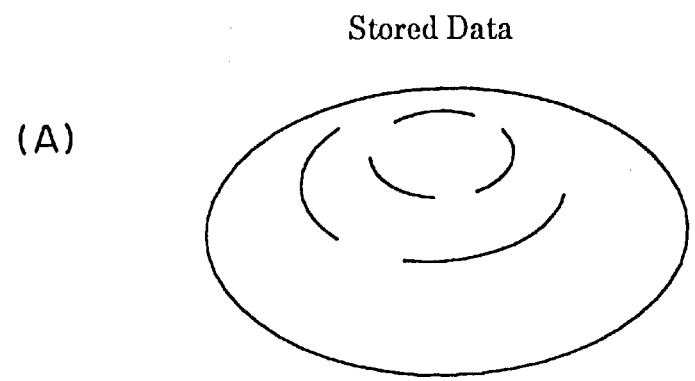
FIG. 62 is perspective views of (A) stored data of a tablet, (B) measured data of a tablet with a defect portion, and (C) measured data of a tablet smaller than the stored data thereof.
Figure 62:
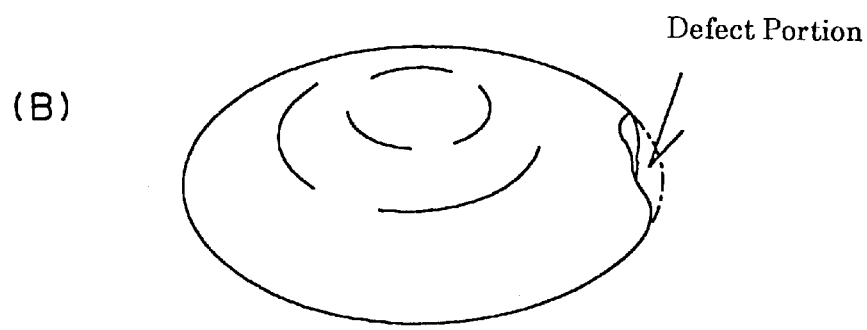
Figure 62:
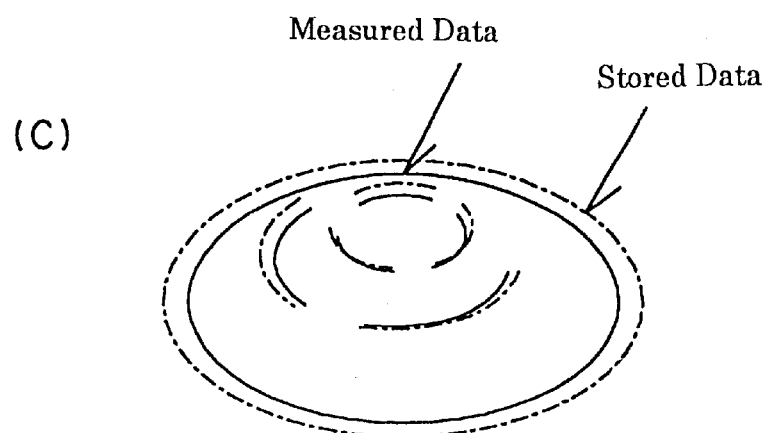

In the case of the defect of foreign material mixing, cracked medicine, or wrong count of medicines, since the number of defective package is one, the prescription data for the defective package is set as interrupt standby information in the packaging machine. Small objects, such as screws, wires, nuts, stone fragments, metal fragments, etc. that do not transmit X-rays, or that do not match the verification criteria data, are all judged as being foreign material. In the case that the measured data coincides only with 90% of the stored data because of the presence of the defect portion lower than 10% as shown in FIGS. 62(A) and (B), such package is decided as good package. If the measured data is recognized as smaller data than the stored data because of defect portion more than 10%, such data is decided as split tablet. In the case of inconsistency of the data because the measured data coincides in its shape with the stores data but the former is smaller or larger in its size than the later as shown in FIG. 62(C), if the measured data falls within the tolerance of the medicine stored beforehand in the storing means, then the medicine measured is decided as one conformable to the prescription. If the measured data is over the tolerance, then the medicine measured is treated as one to be packed in another package.

In the case of a discrepancy between the prescribed medicine type and the packaged medicine type, the same processing as described above is performed. However, if the same defect occurs successively, the cause may be an erroneous setting of a tablet cassette. Therefore, it is preferable to stop the packaging and produce an error indication, to reset the prescription data.

<Tablet verification criteria data>

Tablet verification criteria data will be described next. Comparison data that serve as criteria become necessary when verifying tablets. Preferably, this tablet verification criteria data is stored in the following three forms.

1. X-ray measured data with noise eliminated for each tablet is stored.
2. X-ray measured data corrected by transmissivity for each tablet is stored.
3. Data is stored as three-dimensional data size including the color information of each tablet.

In addition, equations for the volume, transmissivity, shape, size, etc. of each tablet can be stored.

Figure 47:
FIG. 47 is a diagram showing examples of verification criteria data.
Figure 47:
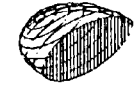
Figure 47:
Figure 47:
Figure 47:
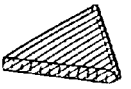
Figure 47:
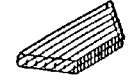
Figure 47:
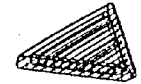
Figure 47:
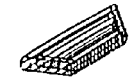
Figure 47:
Figure 47:
Figure 47:
Figure 47:
Figure 47:
Figure 47:
Figure 47:
Figure 47:
Figure 47:
Figure 47:
Figure 47:
Figure 47:
Figure 47:
Figure 47:
Figure 47:
Figure 47:

FIG. 47 shows medicine data converted to three-dimensional data for storing. Those corresponding to the apparatus of FIG. 10 and those corresponding to the apparatus of FIG. 37 are shown.

The data corresponding to the apparatus of FIG. 10 are actually stored in the forms shown in FIGS. 29 and 30, and the illustrated data represent the stored data as converted to three-dimensional images. Since the data corresponding to the apparatus of FIG. 10 are expressed only in terms of the X-ray transmission amount, it is not possible to identify the cross sectional structures of the tablets. However, since the transmission amount varies for each tablet due to its external shape and internal structure, the tablet can be identified from the transmission amount data (prestored as measured data).

On the other hand, the data corresponding to the apparatus of FIG. 37 are stored as three-dimensional image and exterior color data, so that the data can be used as the keys for identifying the cross sectional structure, the internal layer thickness, etc. This is because the X-ray tube in the construction of FIG. 37 is rotating to enable data to be acquired from all directions. The data can also be employed in the apparatus of FIG. 42 or 43.

<Display coloring>

The data after the above image processing is, in some cases, displayed on the monitor so that the packaging process can be checked for any problem by monitoring the condition of the packaged tablets as the tablet packaging operation progresses.

At this time, the data obtained by scanning with X-rays, etc. is sliced image data, and this data cannot be inspected directly. Therefore, when performing the inspection, it is desirable to reproduce a three-dimensional image of the external shape upon which pharmacists usually rely when performing inspection. It is also desirable to faithfully reproduce its color at the same time.

In view of this, of the tablet imaging data prestored in the tablet verification criteria data, the stored data that matches the result of the verification is read out of the tablet verification criteria data, and color information is appended to the data representing the external shape in three dimensions, thus making it possible to identify the external shape of the tablet.

In the case of white colored tablets of the same shape, since such tablets can be identified by comparing their internal structures, it is preferable to display the tablet cross sectional layer structure together with the above display. In this case, the displayed image is colored using a quasi-color, a grayscale conversion table, or the like to distinctly display layer differences. Here, since the direction of light rays is fixed, the image may be displayed in three-dimensional form by coloring with gradations from the direction of light rays. Moreover, pass-fail decision is not necessary to simultaneously conduct with respect to the shape data and the color data but may be conducted separately.

<Recognition of identification code>

Data reproduced as three-dimensional images can also be used to recognize medicine identification code unique to each tablet type. For example, the tablet shown in FIG. 30 or 41 is engraved with an identification code. Therefore, the engraved characters are reproduced as recesses.

In the case of the apparatus equipped with a CCD camera, one side of the tablet can also be captured as image data. In this case, the identification code can be recognized only when painted identification information other than engraved one is facing the front side. It should be noted that although many medicine have white color, the acquired data of such white medicine by the CCD camera are delicately different in their color. Therefore, in the case of acquiring the data with respect to the appearance image of the white medicine, the acquired data by the CCD camera can not be directly used as discriminating data without conducting white regulation or correction of the acquired image data of such white medicine. In addition, the acquired data of the CCD camera depend on hard error in the camera, brightness and direction of the light. Means for solving these problems is as follows.

1. The condition of the light such as brightness, direction and so on is fixed.
2. More than one kind of reference white colors is prepared. The imaging data of such reference white colors are stored as reference white color data.
3. The more than one kind of reference white color data stored in step 2 are compared with the more than one kind of reference white color data previously stored, and then correction of the reference white color data stored in step 2, change of the light condition, or regulation of the operating condition of the CCD camera is conducted.
4. The previous steps 2 and 3 are periodically repeated.

In steps 1 to 4, instead of the reference white color, reference medicine may be used. The means as described above enhance the reliability of the acquired data.

Once the medicine color data or the identification code is recognized with these means, the medicine type can be identified based on this information. When identifying the tablet type, it is first determined whether the medicine identification code can be recognized. If it cannot be recognized, then the tablet is identified based on its shape, dimensions, color, internal structure, etc. In this way, the accuracy of the identification and the speed of the recognition can be increased.

It is preferable to use OCR to recognize the medicine identification code.

Since the three-dimensional images and the images captured by the CCD camera correspond to image data, it is desirable that such images be first converted into font information.

In the case of the three-dimensional images, the problem is that the image cannot be read correctly as the font information if the front and back of characters and the rotation (top and bottom) of the characters cannot be recognized.

In the case of the CCD camera captured images also, the rotation (top and bottom) of the characters must be recognized.

In the case of the three-dimensional images, only engraved data can be recognized as characters, and more than 80% of the tablets engraved with the identification information have a line that serves as reference.

This line is, for example, a straight line forming part of the external shape, or a secant or the pharmaceutical manufacturer's trademark, or the like, and characters are engraved along this reference line.

It is, therefore, desirable to recognize the reference line first and then recognize the character direction pattern with respect to the reference line.

On the other hand, in the case of character information that does not have a reference plane, for example, in the case of a CALNIGEN tablet, characters "HIM" are engraved substantially centralized on one side of the columnar tablet in the diametric direction thereof, and there is no other part that serves as the reference line than the outer circumference of the tablet.

In the case of such tablets also, it is possible to recognize the rotation direction of the characters by reference to one side of the character. Such means can also be applied to the image data captured by a CCD camera. Further, since the medicine identification information consists of alphanumeric characters with a trademark partially appended thereto, the characters can be recognized using simple OCR software, and the recognition does not take much time.

However, since the character size and the font used are more or less different, different sizes and fonts must be supported.

Processing for the creation of three-dimensional image data, filtering, and image restoration will be described in detail below. <Creation of three-dimensional image data>

When radiating X-rays from two different directions onto the object to be detected and capturing images using two line sensors, as shown in FIGS. 34 and 42, the output data of the line sensors can be converted to three-dimensional image data representing the object by relating the output data to the feed speed in the z direction.

When an X-ray beam of $I_0$ passes through the object (tablet), the X-ray absorptance differs depending on the composition, constituents, density, etc. of each layer of the tablet.

When the composition of the tablet consisting of such layers is viewed by breaking it up into units, and the units are assumed to have attenuation coefficients of $u_1$, $u_2$, $u_3$, . . . , $u_n$, then the amount of X-rays transmitted therethrough is expressed by the following equation.

$$I = I_0 \cdot \exp(-u_1 \Delta) \cdot \exp(-u_2 \Delta) \cdots \exp(-u_n \Delta) \quad \text{[Equation 15]}$$
$$= I_0 \cdot \exp\{-(u_1 + u_2 + \cdots + u_n)\Delta\}$$

where $\Delta$ is the length of each unit. Transforming this equation, the following equation is obtained.

$$u_1 \Delta + u_2 \Delta + \cdots + u_n \Delta = l_n \frac{I_0}{I} \quad \text{[Equation 16]}$$

Here, the left-hand side of the equation is obtained by logarithmically transforming the output of the X-ray detector (line sensor), and this is treated as the X-ray detection density.

In the equation 16, regarding $u_i \Delta$ as the density of each unit, their sum is the projection density. Therefore, by using data from several projection directions, the internal density can be obtained by calculation.

Figure 48:
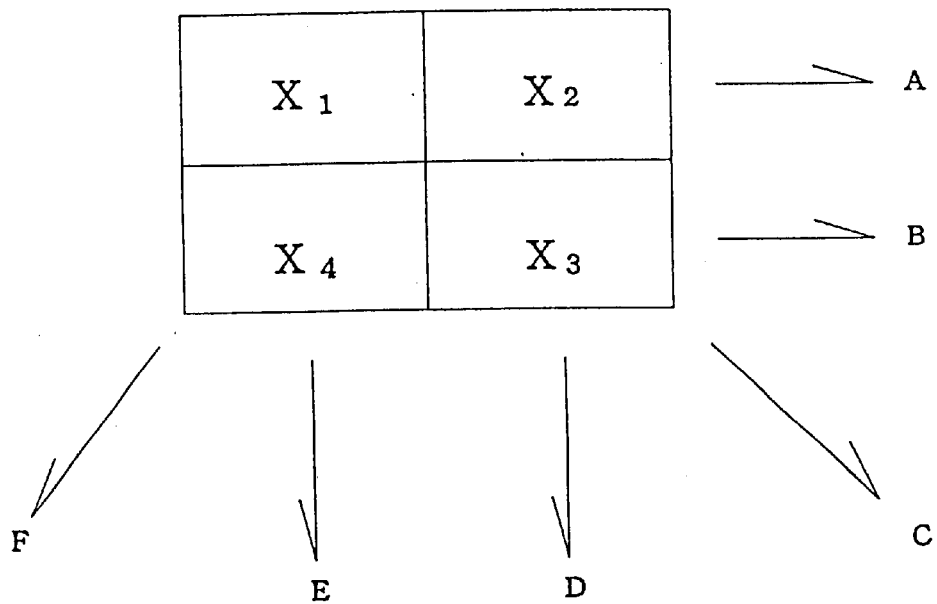
FIG. 48 is a diagram showing X-ray absorption coefficients of four constituent parts of a structure.

As shown in FIG. 48, when the absorption coefficients of four constituent parts of a structure are $X_1$, $X_2$, $X_3$, and $X_4$, respectively, and their true values are $X_1=1$, $X_2=3$, $X_3=2$, and $X_4=4$, the relations between the projection data in six different directions A to F and the unknown absorption coefficients are as follows.

Projection

A: $X_1+X_2=4$

B: $X_3+X_4=6$

C: $X_1+X_3=3$

D: $X_2+X_4=7$

E: $X_1+X_4=5$

F: $X_2+X_3=5$

Here, since the number of the unknowns is four, these can be solved using four equations appropriately selected from the equations A to F.

However, in a practical implementation of this method, the number of unknown elements is very large, and the number of simultaneous equations becomes enormous. Further, if noise is introduced, the values cannot be found correctly.

In view of the above problems, rather than finding the solutions of the equations simultaneously, the solutions can be found using an iterative method.

Figure 49:
FIGS. 49(a–c) are diagrams for explaining an iterative method.

First, the overall average value is taken as the initial estimated value of each element, and changes are sequentially applied so that the value for each projection direction based on the estimated value matches the corresponding data. As shown in FIG. 49(a), correction terms −1 and 1 obtained by comparing the data for directions A and B are equally divided between two rows and added to the respective estimated values. After that, a comparison is made with directions C and D, and corrections are applied in the same manner as above. The results are as shown in FIGS. 49(b) and 49(c), and the reconstruction is thus completed.

Another method of solution is Fourier transform. The Fourier transform of f(x, y) is given by the following equation.

$$F(\mu,\nu)=\int\int f(x,y)\exp\{-j2\pi(\mu x+\nu y)\}dxdy \quad \text{[Equation 17]}$$

When $\mu=0$, the following equation is given.

$$F(0, \nu)=\int(\int f(x,y)dx)\exp(-j2\pi\nu y)dy \quad \text{[Equation 18]}$$

Here, if $g(y)=\int f(x, y)dx$, then $g(y)$ is the integral (projection) of f(x, y) in the y-axis direction, and equation 18 is its one-dimensional Fourier transform.

That is, the one-dimensional Fourier transform of the projection data in the y-axis direction is $F(0, \nu)$. Therefore, this also holds for the projection data in the y-axis direction.

Figure 50:
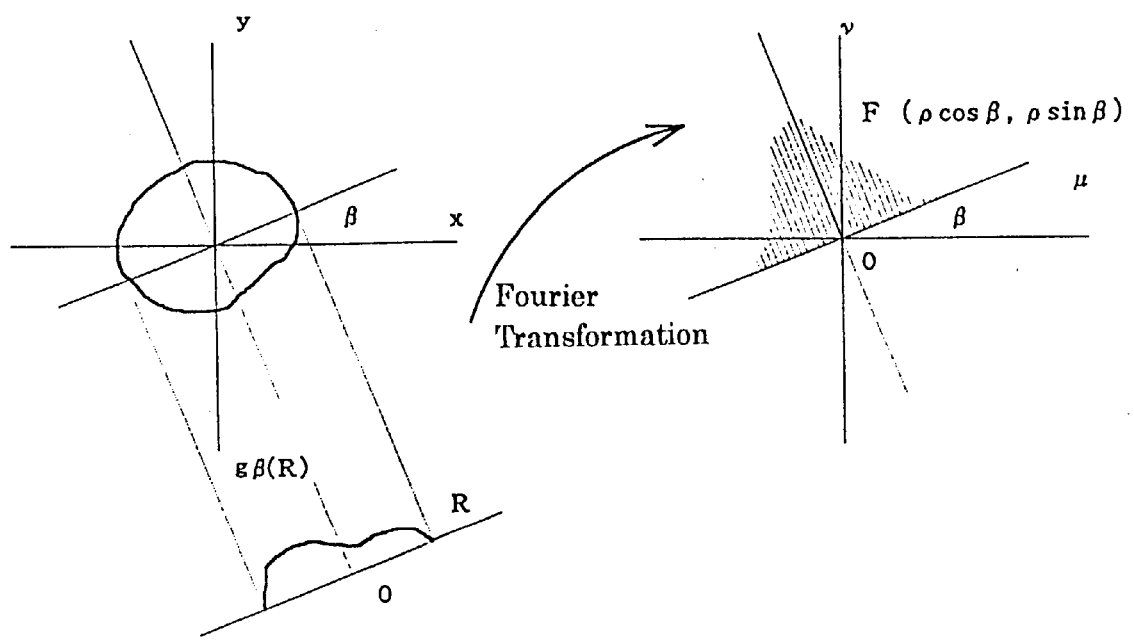
FIG. 50 is a diagram for explaining a Fourier transform method.

In the case of the apparatus corresponding to FIG. 42, when projection data in θ direction is considered, as shown in FIG. 50, the data can be expressed by the following equation.

$$G_\theta(R)=\int\int f(x,y)\delta(x\cos\theta+y\sin\theta-R)dxdy \quad \text{[Equation 19]}$$

Where, $\delta(\cdot)$ is the delta function, and $x\cos\theta+y\sin\theta=R$ represents a straight line inclined in the same direction as the projection direction and having a distance R from the center (origin), while $G_\theta(R)$ is an integral of data on that line.

The Fourier transform equation 17, when converted to polar coordinates (ρ,β), is expressed by the following equation.

$$F(\rho, \beta) = \int\int f(x, y) \exp\{-j2\pi\rho(x\cos\beta + y\sin\beta)\}dxdy \quad \text{[Equation 20]}$$

$$= \int\int\int f(x, y)\delta(x\cos\beta + y\sin\beta - R)$$
$$\exp(-j2\pi\rho R)dxdydR$$

$$= \int G_\beta(R)\exp(-j2\pi\rho R)dR$$

That is, the Fourier transform on a straight line in β direction (one passing through the origin) is equal to the one-dimensional Fourier transform of the projection data of the straight line in that direction in x, y space. Accordingly, by one-dimensionally Fourier transforming the projection data and then inverse transforming the data in the Fourier space, data in real space can be obtained as shown below.

$$f(x, y) = \int\int F(\mu, \nu) \exp\{j2\pi(\mu x + \nu y)\}d\mu d\nu \quad \text{[Equation 21]}$$

$$= \int_0^{2\pi} d\theta \int_0^\infty F(\rho, \theta)$$
$$\exp\{j2\pi\rho(x\cos\theta + y\sin\theta - R)\}dR$$

In the apparatus shown in FIG. 42, the inverse projection of the projection data in θ direction, $b_\theta(x, y)$, is expressed by the following equation.

$$b_\theta(x,y) = \int G_\theta(R)\delta(x\cos\theta + y\sin\theta - R)dR \quad \text{[Equation 22]}$$

Summing the data in the θ direction, the inverse projection image is expressed by the following equation.

$$f_b(x, y) = \int_0^\pi b_\theta(x, y)d\theta \quad \text{[Equation 23]}$$

$$= \int_0^\pi d\theta \int_0^\infty G_\theta(R)\delta(x\cos\theta + y\sin\theta - R)dR$$

Assuming that θ is fixed, $g_\theta(R)$ is a function with R as the variable, and it is given by an inverse transform of its Fourier transform F(ρ, θ), that is, $$\int_{-\infty}^\infty F(\rho, \theta)\exp(j2\pi\rho R)d\rho \quad \text{[Equation 24]}$$

Hence, the equation 23 is expressed by the following equation.

$$f_b(x, y) = \int_0^\pi d\theta \int_{-\infty}^\infty F(\rho, \theta)\exp\{j2\pi\rho(x\cos\theta + y\sin\theta)\}d\rho \quad \text{[Equation 25]}$$

A comparison between the equations 25 and 20 shows that ρ in the integrand of the equation 20 is missing in the equation 25. It is therefore seen that to obtain the data of the equation 20, |ρ|F(ρ, θ) should be used in place of F(ρ, θ).

Multiplication in the Fourier space corresponds to a convolution in the real space. Supposing the real space is sampled at intervals of w (=line sensor pitch), in the Fourier space the bandwidth is limited by R=1/2w according to sampling theorem.

Therefore, fining the inverse transform of the Fourier function (taking the real part), the following equation is obtained.

$$g(r) = \int_{-R}^R |\rho|\cos 2\pi R\rho d\rho \quad \text{[Equation 26]}$$

$$= \frac{R}{\pi r}\sin 2\pi Rr - \frac{1}{2(\pi r)^2}(1 - \cos 2\pi Rr)$$

Here, when r=nw where n=0, ±1, ±2, . . . , then the following equation is obtained.

$$g(kw) = \begin{cases} 1/4w^2 & k = 0 \\ -1/(\pi kw)^2 & k\text{:odd number} \\ 0 & k\text{:even number}(\neq 0) \end{cases} \quad \text{[Equation 27]}$$

Figure 51:
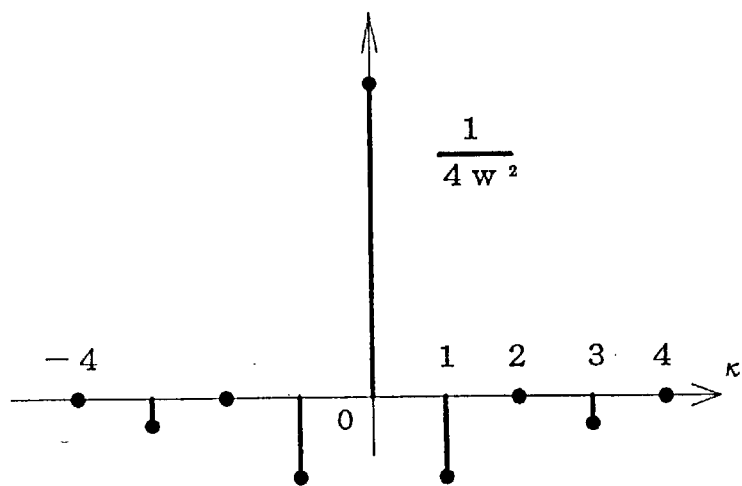
FIG. 51 is a diagram showing a function g(k, w)
Figure 52:
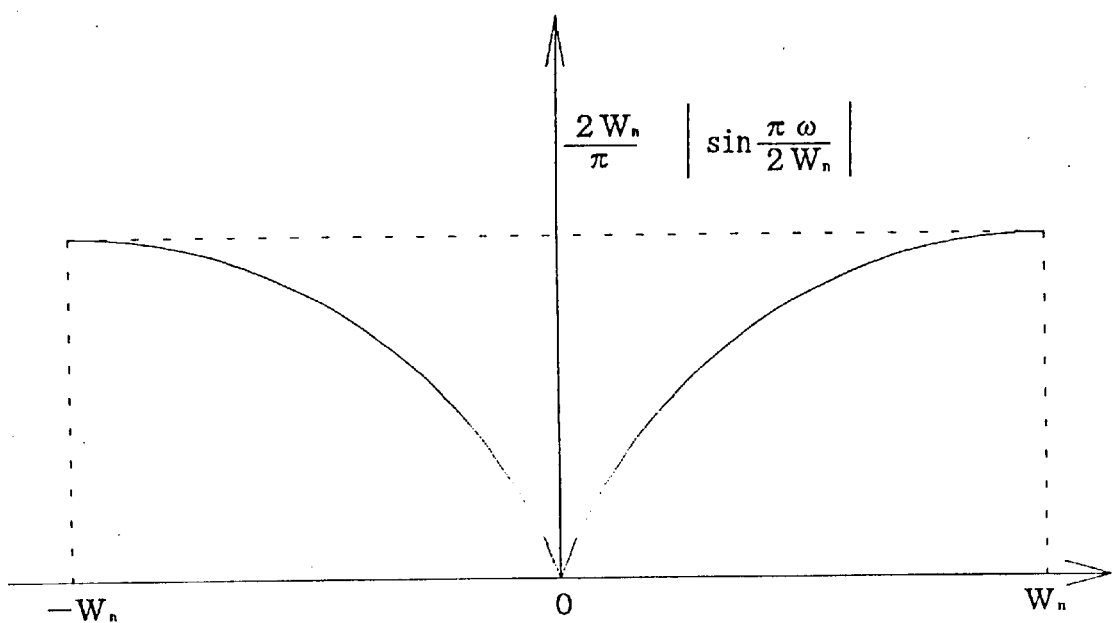
FIG. 52 is a diagram showing an improved version of the function of FIG. 51.

This gives the function such as shown in FIG. 51. It is also possible to use an improved version of the function of FIG. 51, as shown in FIG. 52.

<Filtering>

Tablet inspection data is subjected to noise elimination, enhancement, and other filtering operations to enable comparison with the verification criteria data.

Usually, since the data detected by the X-ray detection means contains noise, the data seldom perfectly matches the verification criteria data when comparing the data with the verification criteria data. Therefore, the acquired data is converted to three-dimensional form, representing an external contour, an internal structural pattern, or the like, for comparison and verification.

The external contour of a sugar-coated tablet or the like is of a layered structure comprising 80% of center portion of medicine and a protective sugar shell coating the center portion, or further comprising a protective material provided under the sugar shell to ensure that the medicine will reach the intestines.

In many cases, capsules or the like contain a granulated or powdered medicine, whose X-ray transmissivity differs distinctly depending on the powdered shape, etc. However, when it comes to comparison with the verification criteria data, the difference level becomes large.

Medicine characterized in their external contour shape can be easily identified from their external contour shapes alone.

The detection data obtained by the apparatus involves the following problem when identifying the external contour.

FIG. 33 shows the state in which X-rays are projected onto the tablet. Radiation beam lines from the upper and lower portions of the target of the X-ray tube intersect because of the tilting of the target. One of the two beam lines is blocked by the contour of the object to be detected, but the other beam line does not hit the contour and is detected directly by the X-ray detector. This results in the formation of an umbra, the area where both beam lines are completely blocked, and a penumbra, the area where one of the two beam lines is blocked. This penumbra is detected as blurring of the outer contour of the object.

The blurring varies with the position of the object located between the X-ray tube and the detector. That is, as the object is located nearer to the X-ray tube, the area of the penumbra increases, increasing resolution magnification and hence achieving improved accuracy in detecting the dimension of the outer diameter of the object.

Conversely, when the object is located closer to the line sensor, the area of the penumbra decreases. Though this makes it possible to reproduce sharper image data, the resolution magnification becomes close to unity, making it difficult to identify the exact size of the object. To compensate for this shortcoming, the resolution of the line sensor must be increased (by reducing the sensor pitch).

The difference between a medical X-ray CT scanner and the present invention is that in the present invention the object to be detected is much smaller and the object identification accuracy needs to be increased. The reason is that, in the case of tablets, particularly sugar-coated tablets, and capsules, it is not easy to identify medicine type from their external appearance (externally, they resemble in size, shape, and color). Therefore, the resolution must be high enough to be able to measure the outer dimensions with an accuracy below a decimal point and to identify the object from its internal structure, layer structure, and thickness.

Accordingly, a high resolution and the ability to identify the object by comparing sharp external data with stored data (stored object verification data) are required in the present invention.

To satisfy these requirements, the object is placed close to the X-ray tube and the penumbra portion is subjected to data processing to obtain sharp image data.

The penumbra portion varies depending on the thickness and transmissivity of the object, and the amount of attenuation decreases with increasing distance from the umbra portion. The attenuation amount varies with the thickness, transmissivity, and shape of the object, does not have a simple 1/2 characteristic, and cannot be defined as being directly proportional or inversely proportional.

Image data correction and restoration involves eliminating noise and correcting distortion, blurring, etc. occurring in image generation or input process, and thereby restoring an image with high accuracy. On the other hand, image enhancement is performed to better elicit the information characteristics of the image (the information amount that the viewer desires to acquire).

For example, correction involving density conversion can be applied to the penumbra portion. In this penumbra portion, the transmission amount of X-rays is about one half. If the image is displayed without correction, the edge of the object will be blurred. Therefore, correction is applied to increase or decrease the density of this portion, to enhance contour definition.

When increasing the density, the boundary between the umbra and penumbra must be discriminated, which is accomplished by detecting a density level difference.

When decreasing the density of the penumbra portion, it is also difficult to discriminate the umbra/penumbra boundary. However, this can be accomplished by defining an area lying within a certain distance from the umbra/penumbra boundary as being the penumbra portion. Note, here, that when the tablet shape is cylindrical, the penumbra area increases, while in the case of a tablet of a rugby ball-like shape, the penumbra area decreases.

The above density conversion processing is usually performed using a conversion table.

Figure 53:
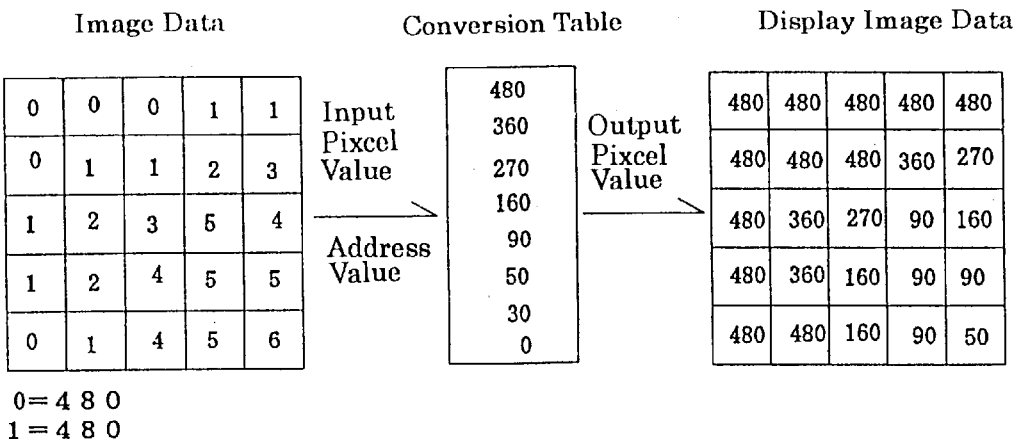
FIG. 53 is a diagram showing a density conversion process.

FIG. 53 shows a simplified diagram of a data table. By using the data table, a correction is applied when adjusting the density of the penumbra portion.

Using the numeric values in the conversion table, the image data whose values are distributed as illustrated is converted to respective image data values, and the image data values are reordered to produce display image data. When the image data value X is smaller than 1, the value in the conversion table is 480, and the image data value 1 corresponds to the penumbra portion. By processing the measured image values in this way, the captured image can be displayed with a crisp contour definition clearer than the actual image data can present.

Figure 54:
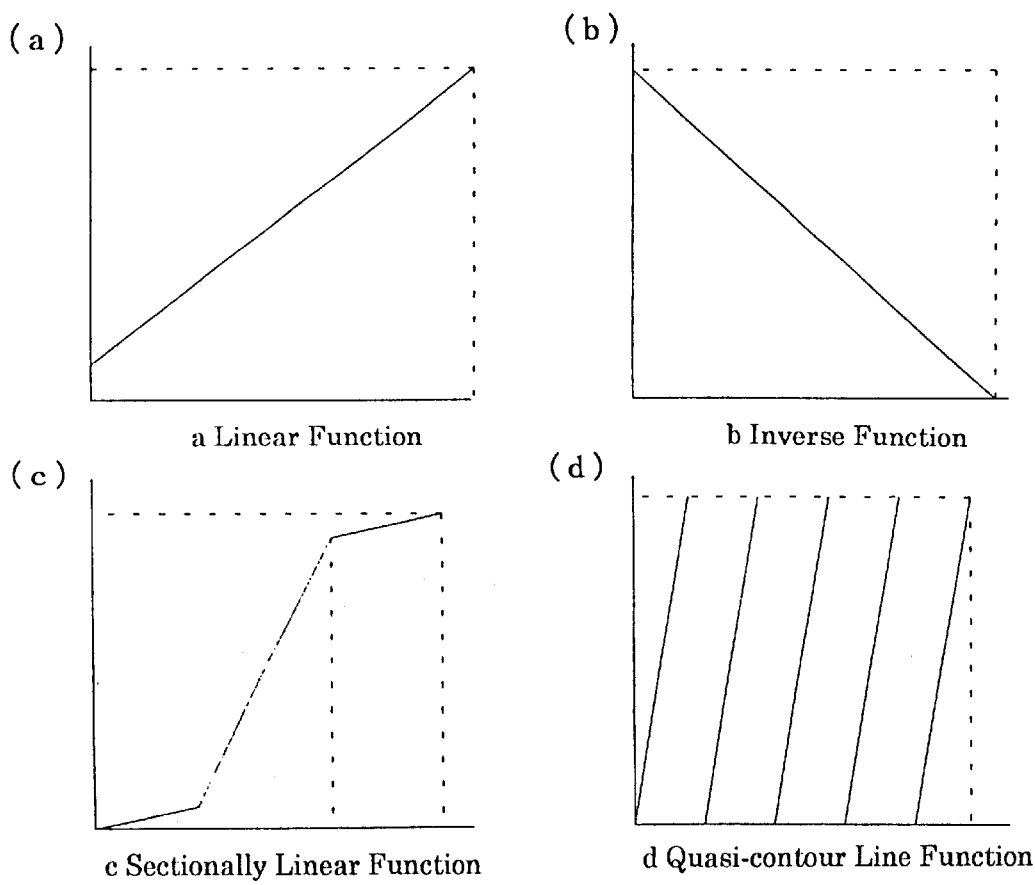
FIGS. 54(a–d) are diagrams showing various function tables.
Figure 55:
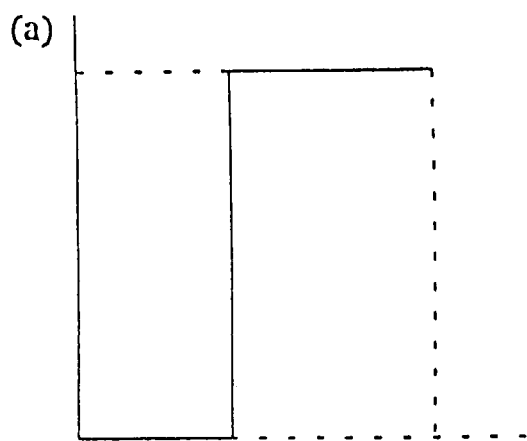
FIGS. 55(a–c) are diagrams showing various function tables as a continuation of FIG. 54.
Figure 55:
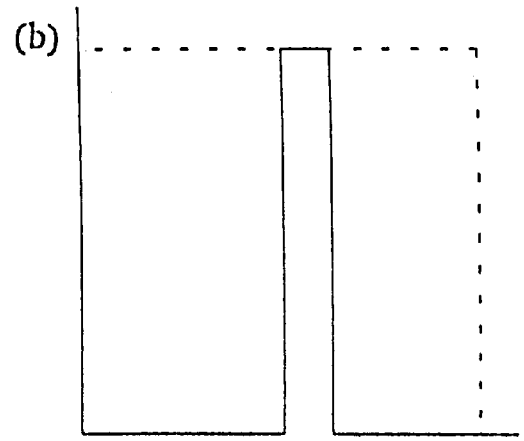
Figure 55:
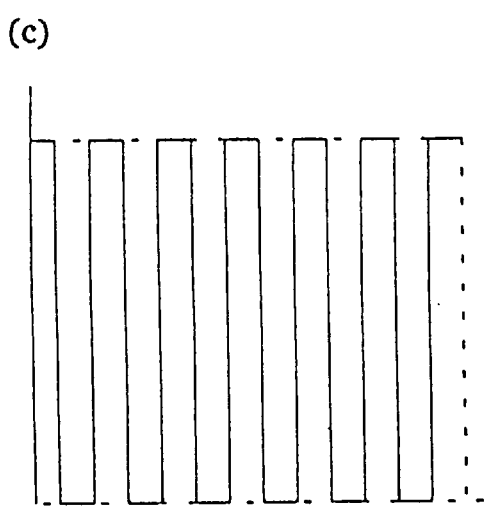

The conversion table can be applied in accordance with a preset intensity function selected as appropriate from among those shown in FIGS. 54(a–d) to 55(a–c). Processing using the linear function table of FIG. 54(a) results in an image with emphasized lightness and darkness. In the case of data with no appreciable X-ray transmission level difference, the lightness/darkness difference is corrected using this function. When the inverse function of FIG. 54(b) is used, the light and dark portions are reversed. That is, white portions are replaced by black portions, and black is displayed as white When the sectionally linear function table of FIG. 54(c) is used, the contour definition of the tablet can be enhanced by excluding the penumbra portion as a real image, as previously described. This is effective in eliminating predictable image blurring or noise. When the quasi-contour line function of FIG. 54(d) or the contour line representation of FIG. 55(c) is used, image density differences can be expressed by a series of gradations. The thresholding of FIG. 55(a) is used to enhance the contour definition, while the banding of FIG. 55(b) is used to express the depth of a three-dimensional object or enhance the contour definition by emphasizing a specified light portion of image color.

Figure 56:
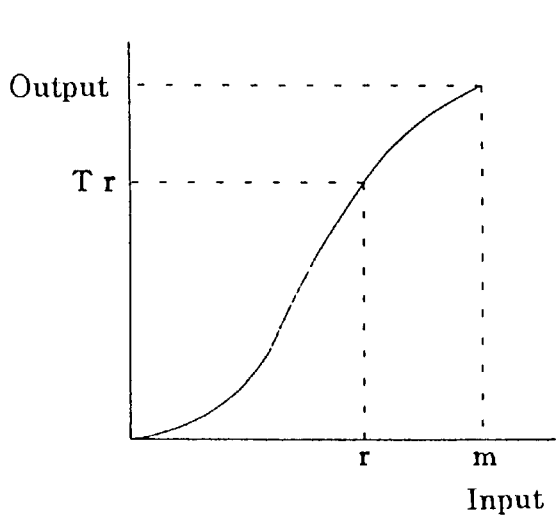
FIG. 56 is a diagram showing input/output relations.

FIG. 56 shows input/output relations corresponding to these function tables. The diagram shows that X-ray measured data of r level is converted to an output Tr in accordance with the curve in the function table shown. Using this function table, the output is produced by reducing the output of the darker and lighter portions and performing no processing on the intermediate contrast portion.

As for the output detected by the X-ray detector, i.e., the line sensor, the level detected at its measuring terminals is not uniform, but the detection level decreases with decreasing distance from the ends of the line sensor. Accordingly, it is also possible to correct the detection level difference by using the above function table.

Further, the output detected by the line sensor contains noise. This noise maybe detected by being partially emphasized due to diffusion, refraction, etc. of the X-rays, or may not be detected. As a result, the detection result may be widely different from the detection level of an adjacent sensor. If it is directly converted into image data, the result does not match the actual shape.

It is therefore necessary to correlate the actual shape and the detection data by performing noise processing. The following methods are used as means of noise processing.

A first method is simple smoothing. If noise is introduced under conditions of fine output span, a curved shape becomes coarse. If the output span is coarse, a curved shape appears smooth even when a certain degree of noise is contained. When noise and signal components are compared, generally the latter has the effect of attenuating the component. A linear filter is given in the form of a convolution operation and is expressed by the following equation.

$$g(i) = \sum_{k=-\infty}^{\infty} f(k)h(i-k) \qquad \text{[Equation 28]}$$

Generally, in a smoothing filter, the value of h(x) is made large at the center (x=0), the value decreasing with increasing distance from the center. Therefore, in many cases, the value is set to Outside certain limits (±W). In this case, the following equation is given.

$$g(i) = \sum_{k=i-w}^{i+w} f(k)h(i-k) \quad \text{[Equation 29]}$$

When simply averaging pixels, h(i, j), when expressed in the form of a 5×5 matrix, is given by the following equation.

$$[h] = \begin{pmatrix} 1/9 & 1/9 & 1/9 & 1/9 & 1/9 \\ 1/9 & 1/9 & 1/9 & 1/9 & 1/9 \\ 1/9 & 1/9 & 1/9 & 1/9 & 1/9 \\ 1/9 & 1/9 & 1/9 & 1/9 & 1/9 \\ 1/9 & 1/9 & 1/9 & 1/9 & 1/9 \end{pmatrix} \quad \text{[Equation 30]}$$

$$[h] = \begin{pmatrix} 1/5 & 0 & 1/5 & 0 & 1/5 \\ 0 & 1/5 & 0 & 1/5 & 0 \\ 1/5 & 0 & 1/5 & 0 & 1/5 \\ 0 & 1/5 & 0 & 1/5 & 0 \\ 1/5 & 0 & 1/5 & 0 & 1/5 \end{pmatrix}$$

When taking a weighted average, the following equation is given.

$$[h] = \begin{bmatrix} 1/8 & 1/16 & 1/8 & 1/16 & 1/8 \\ 1/16 & 1/8 & 1/16 & 1/8 & 1/16 \\ 1/8 & 1/16 & 1/8 & 1/16 & 1/8 \\ 1/16 & 1/8 & 1/16 & 1/8 & 1/16 \\ 1/8 & 1/16 & 1/8 & 1/16 & 1/8 \end{bmatrix} \quad \text{[Equation 31]}$$

$$[h] = \begin{bmatrix} 0 & 1/6 & 0 & 1/6 & 0 \\ 1/6 & 1/3 & 1/6 & 1/3 & 1/6 \\ 0 & 1/6 & 0 & 1/6 & 0 \\ 1/6 & 1/3 & 1/6 & 1/3 & 1/6 \\ 0 & 1/6 & 0 & 1/6 & 0 \end{bmatrix}$$

Besides these filters, a mode filter is used. The mode filter takes a density histogram over a filter section, and outputs its mode value (the most frequent value within the size of the filter).

There is also a median filter which arranges the density values of the pixels within the filter section in a prescribed order and outputs its median. The median filter is particularly effective when eliminating dot-type noise. Instead of using the median, the median filter may use other values such as a maximum value or a minimum value.

In the case of images containing a large amount of noise component, it is difficult to process the noise using the above-described filters alone. In that case, using a dispersion filter, noise can be eliminated without blurring edges.

The principle of such filtering can be accomplished by performing smoothing without averaging an edge portion across both sides thereof. To achieve this, edges must be detected. Sampling variance values of image density in a local region are effective as means for detecting the presence of an edge.

Figure 57:
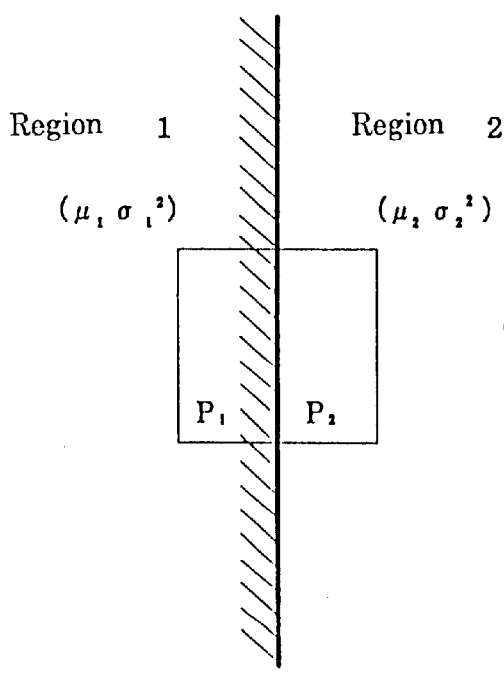
FIGS. 57(a and b) are diagrams showing two adjacent subregions in an image and their density variance values.
Figure 57:
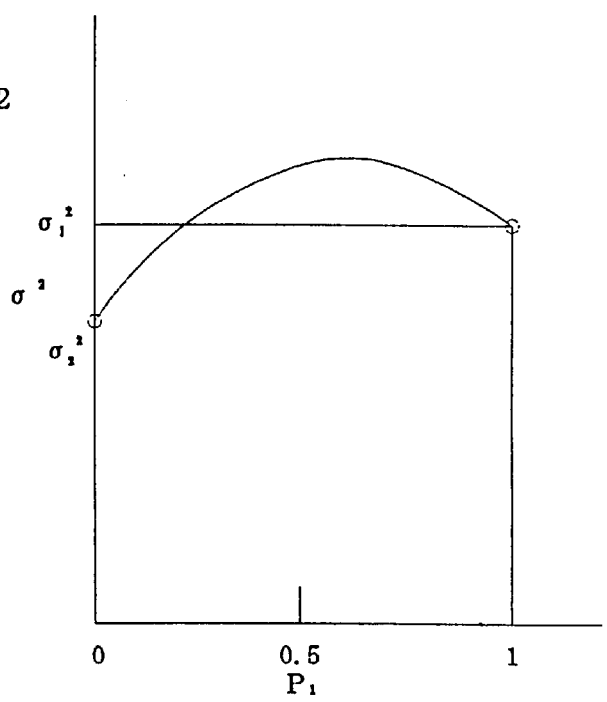

In FIG. 57, consider two adjacent regions, region 1 and region 2, having different density distributions in an image. It is assumed that the density distribution in the region 1 conforms to a probability density function $f_1(x)$ with a mean $\mu_1$ and variance or $\sigma_1^2$, and the density distribution in the region 2 conforms to a probability density function $f_2(x)$ with a mean $\mu_2$ and variance $\sigma_2^2$.

Take a local subregion within the image, and assume that the ratio of region 1 to region 2 in the subregion is $P_1/P_2$ (where $0 \leq P_1, P_2 \leq 1$, $P_1 + P_2 = 1$); then, the density distribution in the subregion obeys the following equation.

$$f(x) = P_1 f_1(x) + P_2 f_2(x) \quad \text{[Equation 32]}$$

The mean $\mu$ and variance $\sigma^2$ of f(x) are respectively expressed by the following equations.

$$\mu = \int x f(x) dx = P_1 \mu_1 + P_2 \mu_2 \quad \text{[Equation 33]}$$

$$\sigma^2 = \int (x-\mu)^2 f(x) dx = P_1 \sigma_1^2 + P_2 \sigma_2^2 + P_1 P_2 (\mu_1 - \mu_2)^2 \quad \text{[Equation 34]}$$

When $\mu_1 \neq \mu_2$, the following equation is obtained by transforming the equation 34 using $P_1 + P_2 = 1$.

$$\sigma^2 = -(\mu_1-\mu_2)^2 \left[ P_1 - \frac{1}{2}\left\{1 + \frac{\sigma_1^2 - \sigma_2^2}{(\mu_1-\mu_2)^2}\right\}\right] + \frac{1}{4}(\mu_1-\mu_2)^2\left\{1 + \frac{\sigma_1^2 - \sigma_2^2}{(\mu_1-\mu_2)^2}\right\}^2 + \sigma_2^2 \quad \text{[Equation 35]}$$

Therefore, as $P_1$, changes from 0 toward 1, that is, as the relative positional relationship between the edge and the subregion changes, $\sigma^2$ changes as shown in FIG. 57(b).

If the condition $$0 < \frac{1}{2}\left\{1 + \frac{\sigma_1^2 - \sigma_2^2}{(\mu_1-\mu_2)^2}\right\} < 1 \quad \text{[Equation 36]}$$

that is $$(\mu_1-\mu_2)^2 > |\sigma_1^2 - \sigma_2^2| \quad \text{[Equation 37]}$$

is satisfied, a maximum point of $\sigma^2$ is located within the interval of $0 < P_1 < 1$. Therefore, when the subregion is lying across the edge, the variance value is large, from which the presence of the edge can be detected.

Next, consider the smoothing filter of the following form in which k×k neighboring subregions A, B, C, and D (denoted $R_1$ to $R_4$ in the following equations) are taken around each attention point (i, j), as shown in FIG. 57, and the output value is determined in accordance with the mean value $\mu_1$ and variance value $\sigma_1^2$ of the density of each subregion without blurring the edge.

Denoting input image by [a] and output image by [b]

$$b^{**} = \sum_{j=1}^{4} \mu_j W_j \quad \text{[Equation 38]}$$

Hence, the mean and variance of each neighboring subregion are expressed by the following equations.

$$\mu_j = \frac{1}{k^2} \sum_{(i'j') \in R_j} a_{i'j'} \quad \text{[Equation 39]}$$

$$\sigma_j = \frac{1}{k^2} \sum_{(i'j') \in R_j} (a_{i'j'} - \mu_j) \quad \text{[Equation 40]}$$

Here, $W_1$ is a weight determined by the value of the variance $\sigma_1^2$ in $R_1$, and the sum is 1.

A number of filters can be considered depending on how $W_1$ is selected. In the simplest method, the mean value of the subregion with the smallest variance is taken as the filter output, and the mean value of the subregion with the smallest variance is output from the filter. That is, the selection is such that Wk=1; sk2≦sm2, all m∈ (1, 2, 3, 4), and 0; k other than the above.

Since at least one of the four subregions can be considered as not containing any edges of the image region, the subregion with the smallest variance is selected, as described above, and the mean value of that subregion is determined as the filter output at the attention point. Since the selected subregion is switched distinctly between both sides of an edge, an extremely sharp edge output can be obtained. On the other hand, even a slight change in the variance can cause subregion switching, and spike-like noise is likely to occur near the edge. It is therefore desirable to use the above filter in combination with a median filter.

The contour and edges of an imaged object can be sharpened by emphasizing high frequency components. For this purpose, a derivative operator is used which shows a local change in image density value and is given by the following equation.

$$\frac{\partial^n}{\partial x^k \partial y^{n-k}} \quad \text{[Equation 41]}$$

This operator is a local derivative operator.

Usually used ones are only when n is 1 or 2. When n=1, $(\partial/\partial x)$ and $(\partial/\partial y)$ are used. The derivative Δ combining these two and its direction θ are respectively expressed by the following equations.

$$\Delta = \left\{ \left(\frac{\partial f}{\partial x}\right)^2 + \left(\frac{\partial f}{\partial y}\right)^2 \right\}^{1/2} \quad \text{[Equation 42]}$$

$$\theta = \tan^{-1}\left(\frac{\partial f}{\partial y} \bigg/ \frac{\partial f}{\partial x}\right) \quad \text{[Equation 43]}$$

In the case of a digital image, these derivative calculations are performed using differences. The first derivatives of x and y are respectively expressed by the following equations.

$$\Delta x(i, j) = f(i, j) - f(i-1, j) \quad \text{[Equation 44]}$$

$$\Delta y(i, j) = f(i, j) - f(i, j-1) \quad \text{[Equation 45]}$$

Here, Δ is expressed by the following equation.

$$\Delta = \{(\Delta x)^2 + (\Delta y)^2\}^{1/2} \; \theta = \tan^{31}(\Delta y/66 \; x) \quad \text{[Equation 46]}$$

The second derivatives in the x and y directions are respectively defined by the following equations.

$$\Delta^2 x(i, j) = \Delta x(i+1, j) - \Delta x(i, j) \quad \text{[Equation 47]}$$
$$= f(i+1, j) + f(i-1, j) - 2f(i, j)$$

$$\Delta^2 y(i,j) = f(i,j+1) + f(i,j-1) - 2f(i,j) \quad \text{[Equation 48]}$$

The following definitions can also be used.

$$\Delta x(i,j) = f(i+1,j) - f(i-1,j) \quad \text{[Equation 49]}$$

$$\Delta y(i,j) = f(i,j+1) - f(i,j-1) \quad \text{[Equation 50]}$$

$$\Delta^2 x(i,j) = \Delta x(i,j) - \Delta x(i-1,j) \quad \text{[Equation 51]}$$

Further, for the first derivative Δ, the following equations can be used instead of the equation 46.

$$|\Delta x| + |\Delta y| \quad \text{[Equation 52]}$$

$$\max(|\Delta x|, |\Delta y|) \quad \text{[Equation 53]}$$

$$(\Delta x)^2 + (\Delta y)^2 \quad \text{[Equation 54]}$$

The Laplacian is defined as $$\nabla^2 f = \frac{\partial^2 f}{\partial x^2} + \frac{\partial^2 f}{\partial y^2} \quad \text{[Equation 55]}$$

In the case of a digital image, the Laplacian is defined as $$\nabla^2(i, j) = \Delta^2 x(i, j) + \Delta^2 y(i, j) \quad \text{[Equation 56]}$$
$$= f(i+1, j) + f(i-1, j) + f(i, j+1) +$$
$$f(i, j-1) - 4 \cdot f(i, j)$$

Transforming this equation, we obtain $$\nabla^2(i, j) = -5\left[f(i, j) - \left(\frac{1}{5}\right)\left\{\begin{array}{l} f(i+1, j) + \\ f(i-1, j) + f(i, j+1) + \\ f(i, j-1) + f(j, i) \end{array}\right\}\right] \quad \text{[Equation 57]}$$
$$= 5[\{\text{neighborhood mean value of } f(i, j)\} - f(i, j)]$$

which thus expresses the difference between the mean value of the neighborhood region and its pixel value.

Since these derivative calculations are used to detect the amount of change of density, high frequency noise is also emphasized. Therefore, in order to reduce the high frequency noise in collaboration with the smoothing filter and to detect the change in the density value of the signal component, the following calculations using 3×3 neighboring pixels are employed.

$$\begin{pmatrix} A & B & C \\ D & E & F \\ G & H & I \end{pmatrix} \quad \text{[Equation 58]}$$

1.

$$\Delta = \{(A+B+C-G-H-I)^2 + (A+D+G-F-I)^2\}^{1/2} \quad \text{[Equation 59]}$$

2.

$$\Delta = |A+B+C-G-H-I| + |A+D+G-C-F-I| \quad \text{[Equation 60]}$$

3.

$$\Delta = E - \min\{A,B,C,D,E,F,G,H,I\} : \text{greatest gradient} \quad \text{[Equation 61]}$$

4.

$$\Delta = |B-H| + |D-F| + |A-I| + |C-G| \quad \text{[Equation 62]}$$

The following operations 5 and 6 are performed to obtain the differentiated image in two directions, i.e., x and y directions.

5.

$$\Delta x = \begin{pmatrix} -1 & 0 & 1 \\ -2 & 0 & 2 \\ -1 & 0 & 1 \end{pmatrix} \quad \Delta y = \begin{pmatrix} -1 & -2 & -1 \\ 0 & 0 & 0 \\ 1 & 2 & 1 \end{pmatrix}$$ [Equation 63]

6.

$$\Delta x = \begin{pmatrix} -1 & 0 & 1 \\ -1 & 0 & 1 \\ -1 & 0 & 1 \end{pmatrix} \quad \Delta y = \begin{pmatrix} -1 & -1 & -1 \\ 0 & 0 & 0 \\ 1 & 1 & 1 \end{pmatrix}$$ [Equation 64]

When the above filtering operations 5 and 6 are performed, negative pixel values often occur. Therefore, it is preferable to take absolute values or add suitable bias values when producing the display.

Also, an image obtained by adding the absolute values in x and y directions can be used as the differentiated image.

Examples of the Laplacian corresponding to the second derivative include $$\nabla_4 = \begin{pmatrix} 0 & 1 & 0 \\ 1 & -4 & 1 \\ 0 & 1 & 0 \end{pmatrix} \quad \nabla_8 = \begin{pmatrix} 1 & 1 & 1 \\ 1 & -8 & 1 \\ 1 & 1 & 1 \end{pmatrix}$$ [Equation 65]

In this case also, absolute values can be taken or suitable bias values added when displaying the processed image.

Since the Laplacian emphasizes high frequency components, the image can be sharpened by subtracting the Laplacian image from the original image; this also has the effect of restoring blurring.

As examples of filters implementing this, the followings are used.

$$\nabla_{4E} = \begin{pmatrix} 0 & -1 & 0 \\ -1 & 5 & -1 \\ 0 & -1 & 0 \end{pmatrix} \quad \nabla_{8E} = \begin{pmatrix} -1 & -1 & -1 \\ -1 & 9 & -1 \\ -1 & -1 & -1 \end{pmatrix}$$ [Equation 66]

Besides these filters, a low-pass filter or a high-pass filter can be used. The terms "low-pass" and "high-pass" used here respectively mean as follows. For example, in a white and black original image, the "low-pas" represents a portion where the intensity of white is high, and the "high-pass" represents a portion where the intensity of black is high.

The low-pass filter is set so as to reduce high frequency components H(u, v) representing black components, and includes a rectangular filter and a Butterworth filter such as described below.

The rectangular filter has a cut-off frequency distinctly separating the pass band and the attenuation band. Denoting the cut-off frequency as $R_0$, and the filter characteristics is given by the following equation.

$$H(\mu, v) = \begin{cases} 1; R(\mu, v) \le R_0 \\ 0; R(\mu, v) > R_0 \end{cases}$$ [Equation 67]

Figure 58:
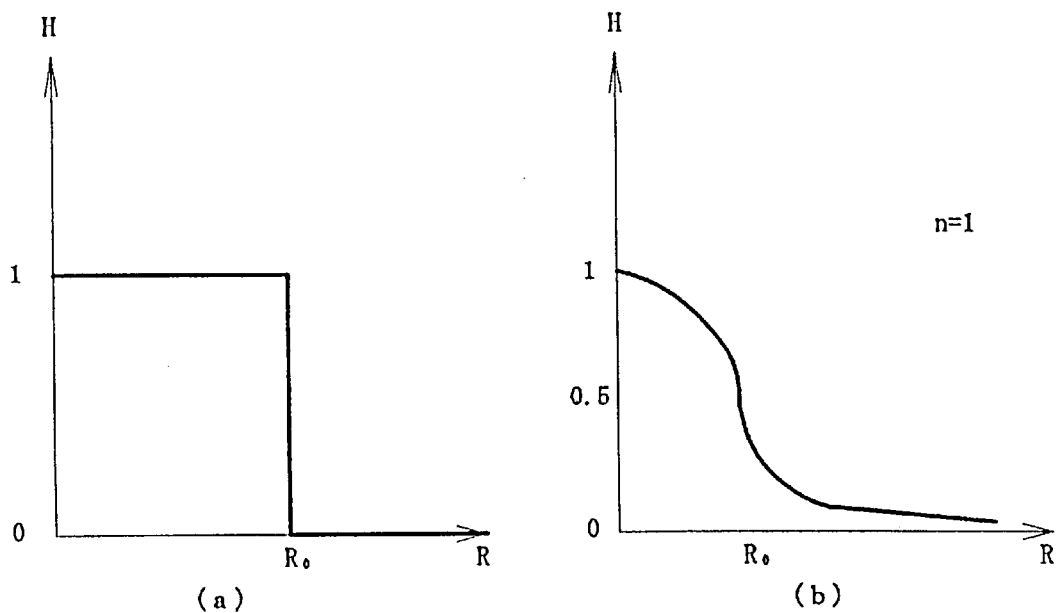
FIGS. 58(a and b) are diagrams showing filter functions.

The form of the filter function is shown in FIG. 58(a) is obtained.

The Butterworth filter does not have the sharp cut-off characteristic of the rectangular filter, but has a gradually decreasing pass band. The filter characteristic is given by the following equation.

$$H(\mu, v) = \left[1 + \left\{\frac{R(\mu, v)}{R_0}\right\}^{2n}\right]^{-1}$$ [Equation 68]

The form of the filter function when n=1 is shown in FIG. 58(b).

The high-pass filter will be described below. H(u, v) is set so as to reduce the low frequency components. Examples of this filter also include a rectangular filter and a Butterworth filter.

The rectangular filter is expressed by the following equation.

$$H(\mu, v) = \begin{cases} 0; R(\mu, v) \le R_0 \\ 1; R(\mu, v) > R_0 \end{cases}$$ [Equation 69]

The Butterworth filter is expressed by the following equation.

$$H(\mu, v) = \left[1 + \left\{\frac{R_0}{R(\mu, v)}\right\}^{2n}\right]^{-1}$$ [Equation 70]

Figure 59:
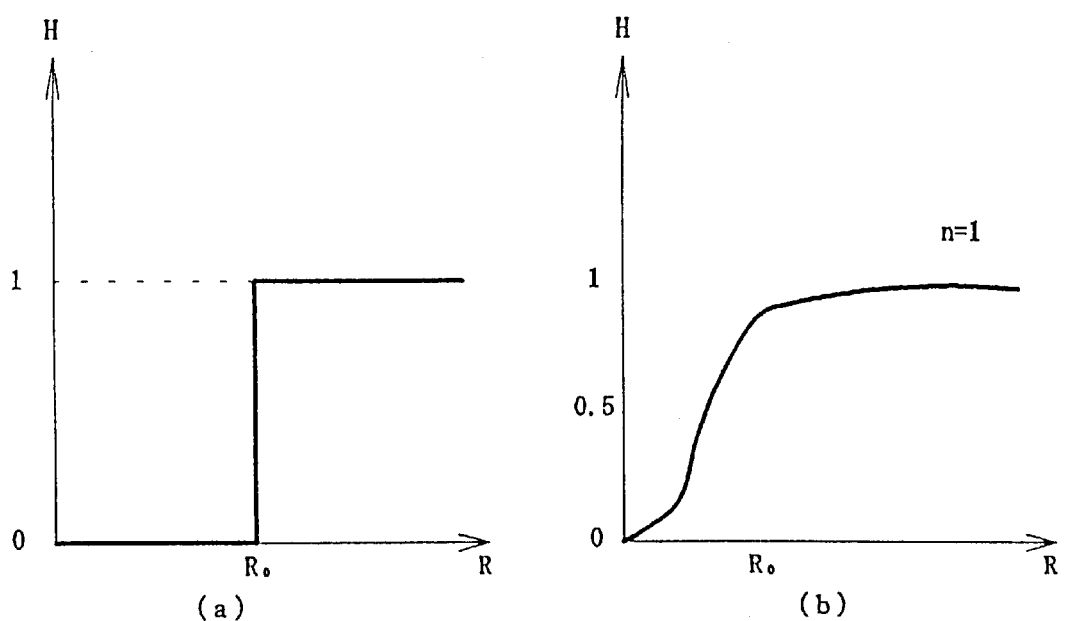
FIGS. 59(a and b) are diagrams showing other filter functions.

These filter functions are shown in FIGS. 59(a) and 59(b), respectively. Part (b) showing the Butterworth filter is for the case of n=1.

When a certain amount of radiation emitted from the X-ray tube is detected by the sensor, the image screen may become too dark or too bright depending on the thickness, shape, and absorptance of the detected object, making it difficult to identify the medicine type. In such cases, using the above-described low-pass or high-pass filter, the image captured with a contrast outside a prescribed contrast range can be corrected to a state where the medicine type can be identified.

<Image restoration>

Since the X-ray imaging data corrected by the above filtering is output as data for the monitor or printer, a blurred image is not desirable for tablet type identification.

Figure 60:
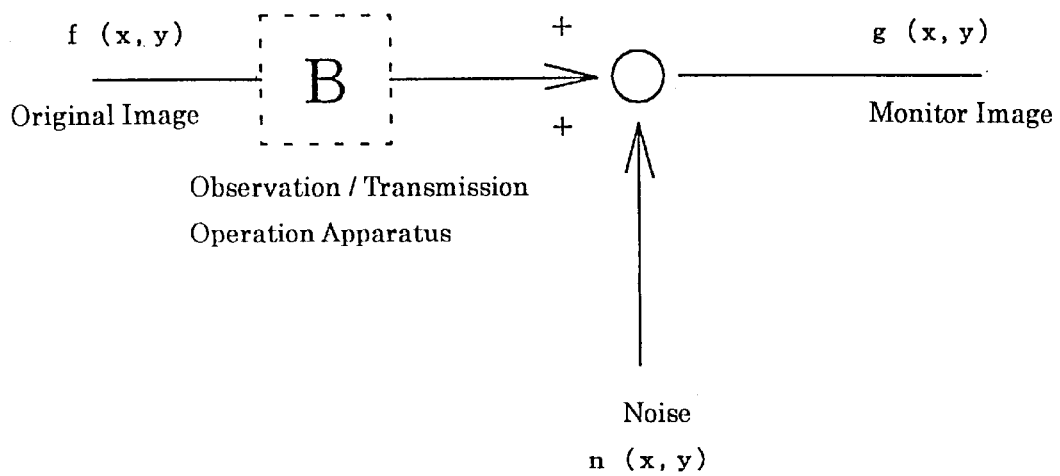
FIG. 60 is a diagram showing a path for monitoring an image.

The path for monitoring the image is shown in FIG. 60. Usually, blurring occurs on the monitor, or noise is superimposed. Accordingly, using the above-described filters, the image must be corrected to a level that allows monitoring.

In the case of additive noise, when the original image is denoted by f(x, y), noise by n(x, y), and observation/transmission operation apparatus by B, the monitor image can be obtained by the following equation of the form $$g(x,y)=B\cdot f(x,y)+n(x,y)$$ [Equation 71]

When B is linear, the image can be expressed as $$g(x,y)=\int_{-\infty}^{\infty} f(\alpha,\beta(x,\alpha,y,\beta)d\alpha d\beta+n(x,y)$$ [Equation 72]

Where, b (x, α, y, β) is the point spread function representing the impulse response at point (α, β). When the position (α, β) of this function is irrelevant, the image can be expressed as $$g(x,y)=\int_{-\infty}^{\infty} f(\alpha,\beta)b(x-\alpha,y-\beta)d\alpha d\beta+n(x,y)$$ [Equation 73]

Since the restoration problem is to estimate the original image f from the monitor image g, the equation 63 is Fourier transformed as $$G(\mu,v)=B(\mu,v)F(\mu,v)+N(\mu,v)$$ [Equation 74]

To estimate F(u, v) from G(u, v), it becomes necessary to determine M(u, v) in the following equation.

$$\hat{F}(\mu,v)=M(\mu,v)\cdot G(\mu,v) \quad \text{[Equation 75]}$$

If the object is moving, the monitor image data in the absence of noise is $$g(x, y) = \int_{-T/2}^{T/2} f\{x - \alpha(t), y - \beta(t)\} dt$$

Where, $\alpha(t)$ and $\beta(t)$ are x- and y-direction components of the displacement and T is the exposure time.

The Fourier transform of the above equation is $$G(\mu, v) = F(\mu, v) \int_{-T/2}^{T/2} \exp[-j2\pi\{\mu\alpha(t) + v\beta(t)\}] dt \quad \text{[Equation 77]}$$

and the image transform function $B(\mu,v)$ is obtained by the following equation.

$$B(\mu, v) = \int_{-T/2}^{T/2} \exp[-j2\pi\{\mu\alpha(t) + v\beta(t)\}] dt \quad \text{[Equation 78]}$$

When the object is moving in x direction at a constant speed a, that is, when $\alpha(t)=at$ and $\beta(t)=0$, then $$B(\mu, v) = \frac{1}{\pi a \mu} \sin \pi a \mu t \quad \text{[Equation 79]}$$

If B(u, v) is known and noise is not present, then the estimated value of F(u, v) should be given by $$\hat{F}(\mu, v) = \frac{G(\mu, v)}{B(\mu, v)} \quad \text{[Equation 80]}$$

However, when the value of B(u, v) is 0 or close to 0, if a division is made by that value, difficulties often arise. The problem becomes serious particularly in the presence of noise. That is $$\hat{F}(\mu, v) = F(\mu, v) + \frac{N(\mu, v)}{B(\mu, v)} \quad \text{[Equation 81]}$$

Generally, as (u, v) moves away from the origin, B(u, v) drops off rapidly compared with N(u, v) and becomes close to 0 (in high frequency regions). On the other hand, since noise is relatively independent of frequency, if B (u, v) becomes close to 0, the value of N(u, v)/B(u, v) becomes relatively large, producing an undesirable result. Accordingly, in the high frequency regions, provisions are made not to divide N(u, v) by B(u, v) but to use its value as is (by setting B(u, v) to 1) to avoid producing an undesirable result.

That is, as the inverse filter function, it is preferable to use a filter function that is set to inverse of B(u, v) for frequencies within a frequency range of a radius $R_0$, and set to 1 for higher frequencies.

$$M(\mu, v) = \begin{cases} 1/B(\mu, v) & \mu^2 + v^2 \leq R_0^2 \\ 1 & \mu^2 + v^2 > R_0^2 \end{cases} \quad \text{[Equation 82]}$$

Further, if provisions are made to use a linear restoration function in the presence of noise and one that minimizes the mean square error as a measure of optimum estimated restoration, then the optimum filter function is given by the following equation.

$$M(\mu, v) = \frac{1}{B(\mu, v)} \cdot \frac{|B(\mu, v)^2|}{|B(\mu, v)^2| + S_{nn}(\mu, v)/S_{ff}(\mu, v)} \quad \text{[Equation 83]}$$

where $S_{nn}(u, v)$ is the Fourier spectrum of the noise and $S_{ff}(u, v)$ the Fourier spectrum of the signal.

In the absence of noise, that is, when $S_{nn}=0$, then $$M(\mu, v) = \frac{1}{B(\mu, v)} \quad \text{[Equation 84]}$$

which matches the inverse filter.

This means that in the presence of noise, a correction is applied to 1/B(u, v) to perform optimum restoration in the mean square error sense.

Further, correction of the nonuniformity of the recording/observation system and correction of geometric distortion (at the center and both sides of the line sensor) are not difficult if their associated information can be measured.

If there is nonuniformity due to the position of the measuring system, denoted by i(x, y), degraded image data $$g(x,y)=i(x,y)\cdot f(x,y) \quad \text{[Equation 85]}$$

will be acquire due to the nonuniformity, instead of the image f(x, y) supposed to be acquired.

To correct this nonuniformity, an image f(x, y)=c (constant) with a constant white density value, for example, is captured. Supposing that $g_c(x, y)$ is obtained as the result, the input image g(x, y) should be corrected as $$f(x, y) = \frac{cg(x, y)}{g_c(x, y)} \quad \text{[Equation 86]}$$

Correction of geometric linear distortion can be accomplished by establishing a correspondence between the measured pixel point and the correct position free from distortion. Therefore, if point $(x, y)=(r_j, s_j)$ is the correct coordinate point $(x', y')=(u_j, v_j)$, the distortion can be corrected by substituting these values in $$x' = ax + by + c$$
$$y' = dx + ey + f \quad \text{[Equation 87]}$$

and by obtaining the respective coefficients.

Figure 61:
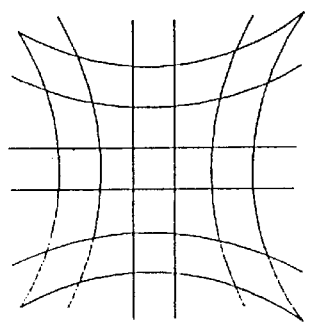
FIG. 61 is a diagram showing examples of distortion.
Figure 61:
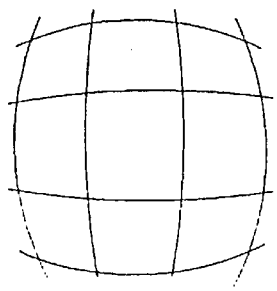
Figure 61:
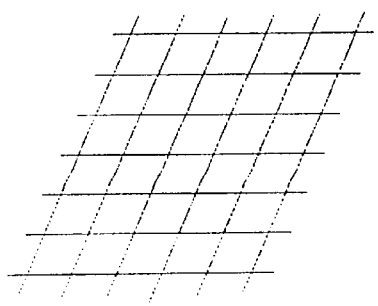
Figure 61:
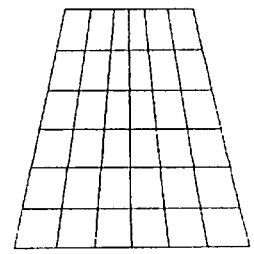

In the case of a digital image, however, since every point is located at a digital position on a lattice, often the corresponding point may not be located on a lattice point. In this case, adjustments become necessary, for example, by making a correction based on the density value of the lattice point or by using an approximate value. Typical forms of distortion are shown in FIG. 61.

Embodiment Using Infrared as Penetrating Radiation

Although, in the above described embodiment, X-ray is used as penetrating radiation, infrared can be also used. The penetrating characteristics of the infrared is very low as compared with the X-ray and is affected with material of the object to be penetrated. For example, the penetration limit of the infrared to the paper is a thickness of 20 mm. The infrared is possible to penetrate into the package belt in which tablets are packed by the tablet packing machine. By measuring light quantity of the X-ray which penetrates into the packed tablet and is attenuated, it is possible to identify the number, the shape and so on of the packed tablets.

As the infrared generation unit, it is possible to use a near-infrared irradiating stroboscopic lamp, an infrared lamp for radiating the light from a halogen lamp through a filter transmitting only infrared component, a near-infrared emitting LED array and so on.

Figure 63:
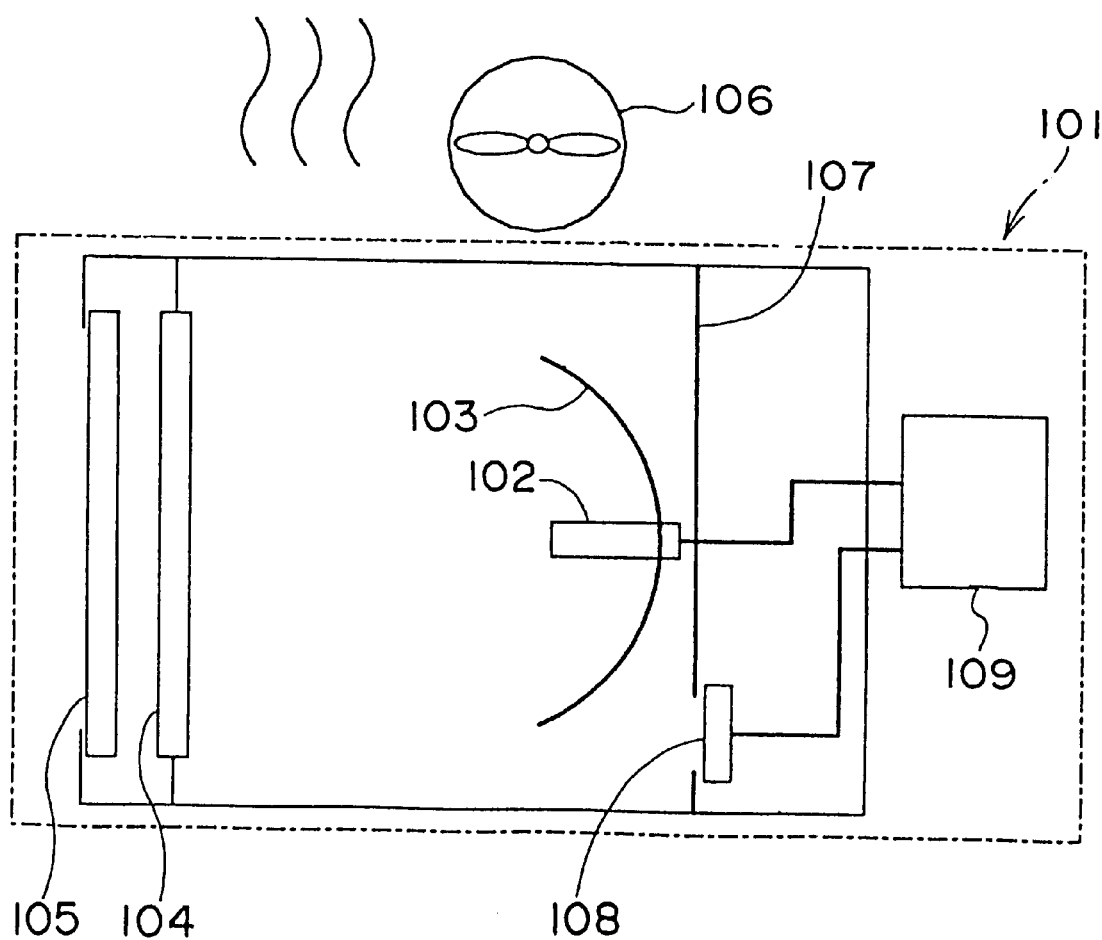
FIG. 63 is a sectional view of an infrared generating unit of an apparatus according to an embodiment utilizing infrared as the penetrating radiation.

FIG. 63 shows an infrared generating unit 101 comprising an infrared lamp. In FIG. 63, numeral 102 denotes a halogen lamp. The halogen lamp 102 is provided with a reflection plate 103. in a radiation direction of the halogen lamp 102 is disposed a near-infrared transmission filter 104 and a slit plate 105. The near-infrared transmission filter 104 is made of such material that is transparent in infrared region, for example, Si, GaAs, InP, GaP, ZnSe, ZnS or so. The slit plate 105 is an aluminum plate with slits. The infrared generating unit 101 is provided with a fan 106 for cooling the unit in order to diffuse the heat generated from the halogen lamp 102 so that the internal temperature does not abnormally rise. At the back of the halogen lamp 102 is disposed an insulating reflection plate 107, behind which are provided a light emitting diode 108 and a controller 109 for maintaining the light quantity of halogen lamp 102 in constant.

Figure 64:
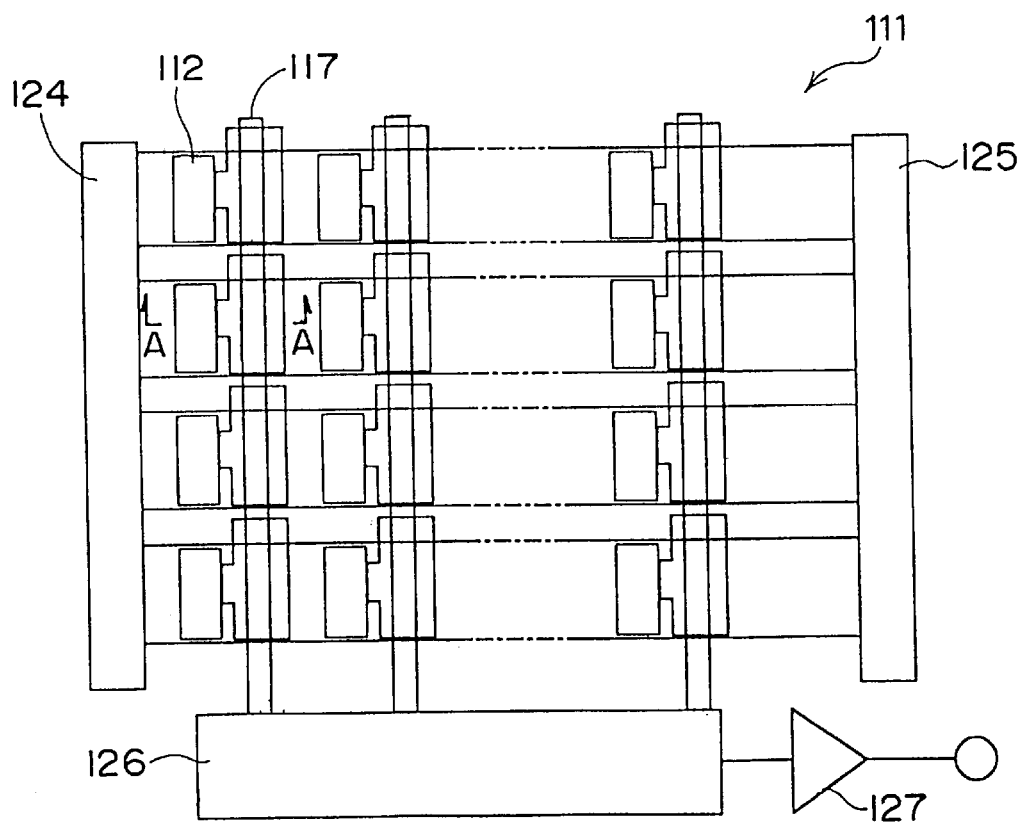
FIG. 64 is a plane view of an infrared detecting unit of the apparatus according to the embodiment utilizing the infrared as the penetrating radiation.
Figure 65:
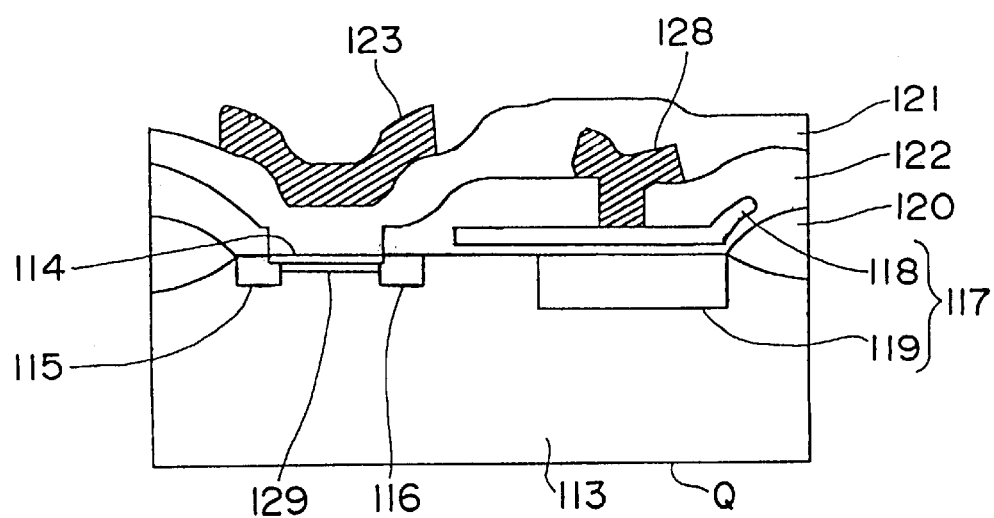
FIG. 65 is a sectional view of the infrared detecting unit along line A—A of FIG. 64.

FIGS. 64 and 65 show an infrared detecting unit 111 for detecting the infrared which is radiated from the infrared generating unit 101 and transmitted the tablets. The infrared detecting unit 111 is provided with a plurality of sensor elements 112 which are disposed in a predetermined layout. Each of the sensor elements 112 comprises a P type silicon semiconductor substrate 113 and a photoelectric conversion layer 114 formed on the substrate 113 by Schottky junction. As the photoelectric conversion layer 114, metal such as platinum, palladium, iridium and so on, or silicide thereof may be used. On the periphery of the photoelectric conversion layer 114 is formed a guard ring 115 by $n^+$ type region for loosening concentration of electric field and preventing dark current. Numeral 116 denotes a transfer gate of $n^+$ type region for transferring signal charge to a vertical shift resister 117 from the photoelectric conversion layer 114. A gate electrode 118 and an n type buried channel 119 constitute the vertical shift resister 117 of CSD (charge sweep device). Numeral 120 is a field insulating film made of silicon oxide film for separation and insulation between elements. Numerals 121, 122 denote interlayer insulation films, which are made of insulator such as oxide film. Behind the photoelectric conversion layer 114 is formed an aluminum reflection film 123 for reflecting the infrared light, which permeates the photoelectric conversion layer 114 without being absorbed therein, in order to enhance light-receiving sensitivity.

The gate electrode 118 of each sensor element 112 on a horizontal line is connected to a transfer gate scanner 124 and also connected to a CSD scanner 125. Thus, the gate electrode 118 serves an electrode of the transfer gate 116 as well as a transfer electrode of CSD. The gate electrode 118 of each sensor element 112 on a vertical line is connected to the vertical shift resister 117. Each of the vertical shift resister 117 is connected to a horizontal shift resister 126 which is in turn connected to an output portion 127.

operation of the infrared detecting unit having above described construction will be described hereinafter. Incident light to the surface Q of the P type silicon semiconductor substrate 113 reaches the photoelectric conversion layer 114 and is subjected to photoelectric conversion. Light signal charge generated in the photoelectric conversion layer 114 is accumulated in the Schottky junction portion. One of scanning lines 128 is selected by the transfer gate scanner 124. To the gate electrode 118 in the horizontal line connected to the selected scanning line 128 is applied a read pulse from the transfer gate scanner 124. Thereby, the light signal charge accumulated in the Schottky junction portion is transmitted to the n type buried channel 119. Simultaneously, the photoelectric conversion layer 114 is reset so that new light signal charge is accumulated until the next read pulse is applied. When a vertical transmitting pulse is applied to the gate electrode 118 from the CSD scanner 125, the light signal charge is transferred in a vertical direction and inputted to the horizontal shift-resister 126. In the horizontal shift resister 126, the light signal charge is transferred in a horizontal direction and outputted from the output portion 127 as a video signal in one horizontal line. Subsequently, the horizontal lines selected by the transfer gate scanner 124 are shifted one by one and the read pulse is applied. Thus, same operation is repeated so that a desired video output can be obtained.

In the case that the gate electrode 118 serves the electrode of the transfer gate 116 for reading the signal charge as well as the transfer electrode of CSD for transferring the signal charge as described above, in order to prevent the transfer gate 116 from being opened when the vertical transferring pulse is applied to the gate electrode 118, a threshold voltage to the transfer gate 116 is set to more than a high level voltage of the vertical transferring pulse.

The photoelectric conversion layer 114 comprising the Schottky junction is possible to detect a light component having an energy more than a height of Schottky barrier. For example, in the case of Schottky junction of platinsilicid (PtSi) and p type silicon, it is possible to detect a light component having a wave length of about 5.6 $\mu$m.

In order to prevent the output from being saturated with respect to the conversion efficiency of the photoelectric conversion layer 114 and the incident light, it is preferable to provide an n type impurity introducing region 129 in the Schottky junction portion between the photoelectric conversion layer 114 and the P type silicon semiconductor substrate 113. Even in the case that the object which need a large amount of infrared radiation is detected, the light sensitivity is decreased by simply reducing the voltage of signal read pulse, preventing the saturation of output and enabling the imaging the object. As a result, it is easily adjust the light sensitivity of the infrared detecting unit so that the output is not saturated with the incident amount of light. as the n type impurity, phosphorous (P), arsenic (As) or the like can be used.

Figure 66:
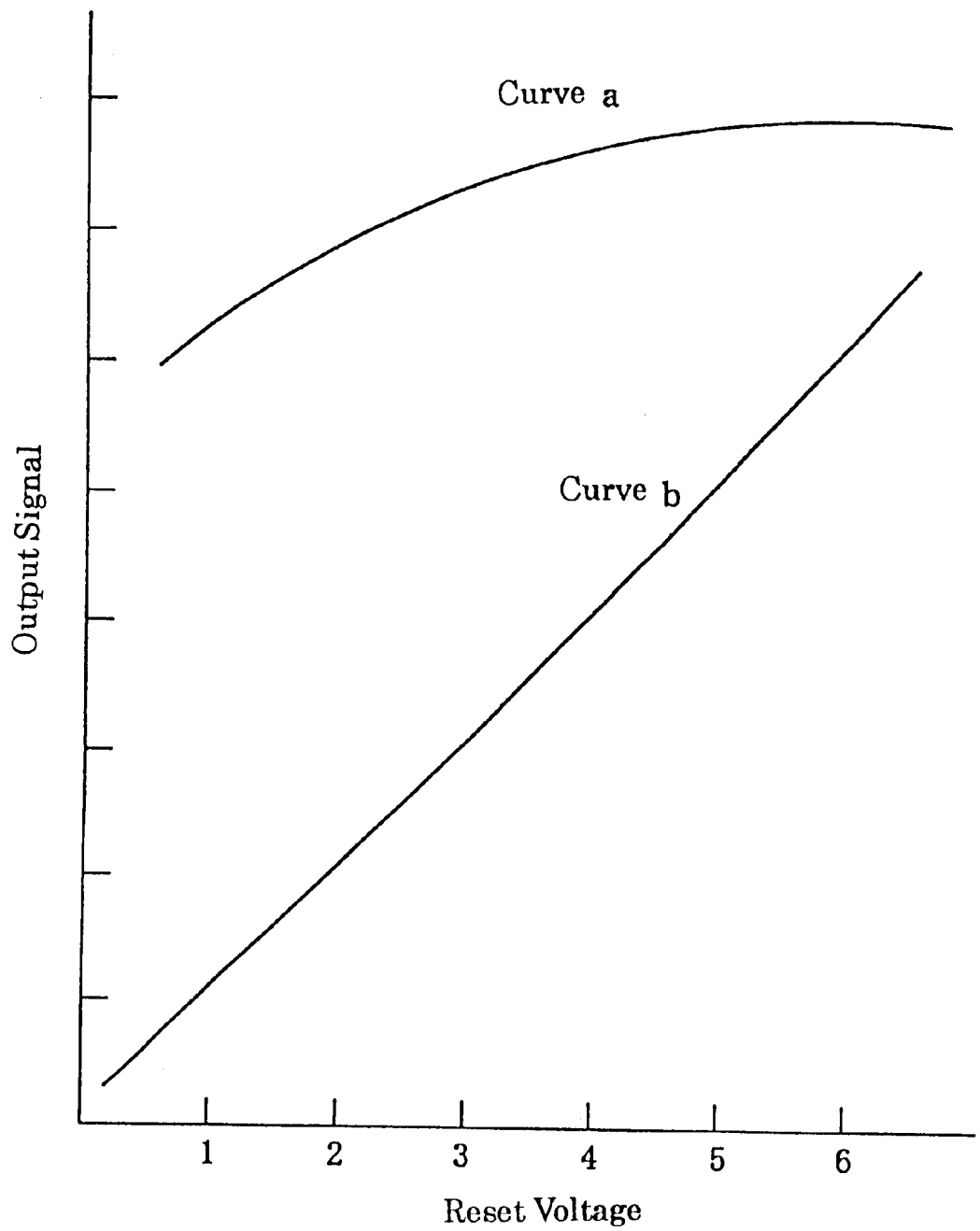
FIG. 66 is a graph showing a relation between reset voltage and output signal in Schottky junction with an n type impurity introducing area (a) or without it (b).

FIG. 66 shows a relation between reset voltage and output signal in Schottky junction portion between the photoelectric conversion layer 114 and the P type silicon semiconductor substrate 113 with the n type impurity introducing area 129 or without it. In the figure, the curve "a" shows the relation in the case with the n type impurity introducing area 129, while the curve "b" shows the relation in the case without it.

In the case of capturing the quantity of infrared permeating the packaged tablet, the higher the sensitivity in the photoelectric conversion layer 114 is, the more advantageous the depth and visibility of the shot image becomes.

Moreover, since the infrared light has low permeability, if the packaged tablets are overlapped, the image is blurred, making it difficult to identify the tablets. Therefore, it is preferable to conduct the imaging after separating the overlapped tablets in the package.

As is apparent from the above description, according to the invention as the first to the third means, the procedures for inspecting packaged tablets to be delivered to the patient by matching the contents of the tablet package against the prescription data and medicine information can be simplified and can be performed at higher speed, while at the same time achieving improved reliability. The inspection labor of pharmacists can also be alleviated. Further, according to the invention as the fourth means, the provision of means for creating video data of packaged tablets makes visual inspection easier than when the tablets are inspected directly by the human eye. Furthermore, the accuracy of the inspection can be enhanced.

What is claimed is:

1. A tablet inspection apparatus for inspecting tablets packaged in a tablet package based on prescription data, comprising:

penetrating radiation generating means for generating penetrating radiation and projecting the same onto said tablet package;

penetrating radiation detecting means for detecting the penetrating radiation generated by said penetrating radiation generating means;

tablet count determining means for determining the number of tablets packaged in said tablet package, based on a detection result supplied from said penetrating radiation detecting means; and comparing and verifying means for verifying whether said tablets are packaged as directed by said prescription data, by extracting from said prescription data tablet count data associated with the tablets supposed to be packaged in said tablet package and by comparing said tablet count data with the number of tablets determined by said tablet count determining means.

2. The tablet inspection apparatus as set forth in claim 1, wherein said tablet count determining means renders said tablet package defective if the data detected by said penetrating radiation detecting means contains data not countable as a tablet.

3. The tablet inspection apparatus as set forth in claim 2, further comprising marking means for appending a mark to said tablet package when said tablet package is judged to be defective.

4. The tablet inspection apparatus as set forth in claim 1, wherein said penetrating radiation detecting means detects the amount of penetrating radiation transmitted through said tablet package.

5. The tablet inspection apparatus as set forth in claim 1, wherein said penetrating radiation detecting means detects a table shadow.

6. The tablet inspection apparatus as set forth in claim 1, wherein a plurality of said penetrating radiation generating means and a plurality of said penetrating radiation detecting means are located in different radiation directions, and wherein the apparatus further comprises reproducing means for reproducing the detection data from said plurality of penetrating radiation detecting means in three-dimensional perspective.

7. A tablet inspection apparatus as set forth in claim 1, wherein said penetrating radiation generating means is mounted rotatably around said tablet package so as to enable the direction of radiation to be changed, and wherein the apparatus further comprises reproducing means for reproducing the detection data from said penetrating radiation detecting means in three-dimensional perspective.

8. A tablet inspection apparatus for inspecting tablets packaged in a tablet package based on prescription data, comprising:

penetrating radiation generating means for generating penetrating radiation and projecting the same onto said tablet package;

penetrating radiation detecting means for detecting the penetrating radiation generated by said penetrating radiation generating means;

tablet shape identifying means for identifying the shape of each of the tablets packaged in said tablet package, based on a detection result supplied from said penetrating radiation detecting means;

storage means for storing tablet shape data for each tablet type; and comparing and verifying means for verifying whether said tablets are packaged as directed by said prescription data, by extracting from said prescription data the tablet type of the tablets supposed to be packaged in said tablet package, by retrieving the tablet shape data corresponding to said tablet type from said storage means, and by comparing said tablet shape data with the tablet shape identified by said tablet shape identifying means.

9. The tablet inspection apparatus as set forth in claim 8, wherein said tablet count determining means renders said tablet package defective if the data detected by said penetrating radiation detecting means contains data from which the shape is not recognizable.

10. The tablet inspection apparatus as set forth in claim 9, further comprising marking means for appending a mark to said tablet package when said tablet package is judged to be defective.

11. The tablet inspection apparatus as set forth in claim 8, wherein said penetrating radiation detecting means detects the amount of penetrating radiation transmitted through said tablet package.

12. The tablet inspection apparatus as set forth in claim 8, wherein said penetrating radiation detecting means detects a tablet shadow.

13. The tablet inspection apparatus as set forth in claim 8, wherein a plurality of said penetrating radiation generating means and a plurality of said penetrating radiation detecting means are located in different radiation directions, and wherein the apparatus further comprises reproducing means for reproducing the detection data from said plurality of penetrating radiation detecting means in three-dimensional perspective.

14. A tablet inspection apparatus as set forth in claim 8, wherein said penetrating radiation generating means is mounted rotatably around said tablet package so as to enable the direction of radiation to be changed, and wherein the apparatus further comprises reproducing means for reproducing the detection data from said penetrating radiation detecting means in three-dimensional perspective.

15. A tablet inspection apparatus for inspecting tablets packaged in a tablet package based on prescription data, comprising:

penetrating radiation generating means for generating penetrating radiation and projecting the same onto said tablet package;

penetrating radiation detecting means for detecting the penetrating radiation generated by said penetrating radiation generating means;

tablet shape identifying means for identifying the shape of each of the tablets packaged in said tablet package, based on a detection result supplied from said penetrating radiation detecting means;

storage means for storing tablet shape data for each tablet type;

tablet count determining means for determining the number of tablets packaged in said tablet package, by extracting from said prescription data the tablet type of the tablets supposed to be packaged in said tablet package, by retrieving the tablet shape data corresponding to said tablet type from said storage means, and by matching said tablet shape data against the tablet shape identified by said tablet shape identifying means; and comparing and verifying means for verifying whether said tablets are packaged as directed by said prescription data, by extracting from said prescription data the tablet type and tablet count data associated with the tablets supposed to be packaged in said tablet package and by comparing said tablet count data with the number of tablets determined by said tablet count determining means.

16. The tablet inspection apparatus as set forth in claim 15, wherein said tablet count determining means renders said tablet package defective if the data detected by said penetrating radiation detecting means contains data not countable as a tablet.

17. The tablet inspection apparatus as set forth in claim 15, wherein said tablet count determining means renders said tablet package defective if the data detected by said penetrating radiation detecting means contains data from which the shape is not recognizable.

18. The tablet inspection apparatus as set forth in claim 15, wherein said penetrating radiation detecting means detects the amount of penetrating radiation transmitted through said tablet package.

19. The tablet inspection apparatus as set forth in claim 15, wherein said penetrating radiation detecting means detects a tablet shadow.

20. The tablet inspection apparatus as set forth in claim 15, wherein a plurality of said penetrating radiation generating means and a plurality of said penetrating radiation detecting means are located in different radiation directions, and wherein the apparatus further comprises reproducing means for reproducing the detection data from said plurality of penetrating radiation detecting means in three-dimensional perspective.

21. A tablet inspection apparatus as set forth in claim 15, wherein said penetrating radiation generating means is mounted rotatably around said tablet package so as to enable the direction of radiation to be changed, and wherein the apparatus further comprises reproducing means for reproducing the detection data from said penetrating radiation detecting means in three-dimensional perspective.

22. A tablet inspection apparatus for inspecting tablets packaged in a tablet package based on prescription data, comprising:

penetrating radiation generating means for generating penetrating radiation and projecting the same onto said tablet package;

penetrating radiation detecting means for detecting the penetrating radiation generated by said penetrating radiation generating means;

storage means for storing tablet image data for each tablet type;

tablet identifying means for identifying the tablet type of each of the tablets packaged in said tablet package by capturing the tablet shape thereof from a detection result supplied from said penetrating radiation detecting means; and video data creating means for creating video data by retrieving the tablet image data corresponding to said tablet type from said storage means and by superimposing said image data on the data detected by said penetrating radiation detecting means.

23. The tablet inspection apparatus as set forth in claim 22, further comprising display means for displaying said video data.

24. The tablet inspection apparatus as set forth in claim 22, further comprising storage means for storing said video image by associating the same with prescription data.

25. The tablet inspection apparatus as set forth in claim 22, wherein a plurality of said penetrating radiation generating means and a plurality of said penetrating radiation detecting means are located in different radiation directions, and wherein the apparatus further comprises reproducing means for reproducing the detection data from said plurality of penetrating radiation detecting means in three-dimensional perspective.

26. A tablet inspection apparatus as set forth in claim 22, wherein said penetrating radiation generating means is mounted rotatably around said tablet package so as to enable the direction of radiation to be changed, and wherein the apparatus further comprises reproducing means for reproducing the detection data from said penetrating radiation detecting means in three-dimensional perspective.

* * * * *